United States Patent
Carson et al.

(10) Patent No.: US 11,266,711 B2
(45) Date of Patent: Mar. 8, 2022

(54) OXYTOCIN COMPOSITIONS AND METHODS OF USE

(71) Applicant: Elgan Pharma Ltd, Nazareth (IL)

(72) Inventors: Dean S. Carson, Palo Alto, CA (US); Marc Pentopoulos, Palo Alto, CA (US)

(73) Assignee: Elgan Pharma Ltd, Nazareth (IL)

( * ) Notice: Subject to any disclaimer, the term of this patent is extended or adjusted under 35 U.S.C. 154(b) by 0 days.

(21) Appl. No.: 16/378,521

(22) Filed: Apr. 8, 2019

(65) Prior Publication Data

US 2020/0316162 A1   Oct. 8, 2020

Related U.S. Application Data

(60) Provisional application No. 62/654,776, filed on Apr. 9, 2018, provisional application No. 62/741,422, filed on Oct. 4, 2018, provisional application No. 62/767,268, filed on Nov. 14, 2018, provisional application No. 62/769,732, filed on Nov. 20, 2018.

(51) Int. Cl.
*A61K 38/095* (2019.01)
*A61P 25/30* (2006.01)
*A61K 9/00* (2006.01)

(52) U.S. Cl.
CPC .......... *A61K 38/095* (2019.01); *A61K 9/0043* (2013.01); *A61P 25/30* (2018.01)

(58) Field of Classification Search
None
See application file for complete search history.

(56) References Cited

U.S. PATENT DOCUMENTS

| | | | |
|---|---|---|---|
| 8,853,158 B2 | 10/2014 | Muscatelli et al. | |
| 9,101,569 B2 | 8/2015 | Rohner-Jeanrenaud et al. | |
| 9,125,862 B2 | 9/2015 | Muscatelli et al. | |
| 2006/0205636 A1* | 9/2006 | Gutkowska | A61K 38/095 514/11.6 |
| 2013/0085106 A1* | 4/2013 | Pedersen | A61P 25/34 514/11.6 |

FOREIGN PATENT DOCUMENTS

| EP | 2571511 B1 | 10/2014 |
|---|---|---|
| EP | 2575853 B1 | 8/2016 |

OTHER PUBLICATIONS

Wachman et al. Neonatal Abstinence Syndrome. Advances in Diagnosis and Treatment. JAMA. 2018;319(13):1362-1374. doi: 10.1001/jama.2018.2640.*
McGregor et al. Breaking the loop: Oxytocin as a potential treatment for drug addiction. Hormones and Behavior. vol. 61, Issue 3, Mar. 2012, pp. 331-339.*
Frazier et al. Emerging therapies for the treatment of neonatal abstinence syndrome. J. Matern. Fetal Neonatal Med. Mar. 9, 2020;1-9. https://pubmed.ncbi.nlm.nih.gov/32146833/.*
Sharapova et al., Effects of prenatal marijuana exposure on neuropsychological outcomes in children aged 1-11 years, Paediatr Perinat Epidemiol., pp. 1-21 (2018); U.S., Wiley.
Fried et al., Differential, effects on cognitive functioning in 13-16-year-olds prenatally exposed to cigarettes and marihuana, Neurotox. and Teratol., 25:427-436 (2003).
Zanos et al., The Oxytocin Analog Carbetocin Prevents Emotional Impairment and Stress-induced Reinstatement of Opioid-Seeking in Morphine-Abstinent Mice, Neuropsychopharmacology, 39:855-865 (2014); United Kingdom.
Woolley et al., The effects of intranasal oxytocin in opioid-dependent individuals and healthy control subjects: a pilot study, Psychopharmacology, 10 pgs (2016), Springer Pub.
Ordean et al., Clinical presentation and management of neonatal abstinence syndrome: an update., Dovepress, vol. 4:75-86 (2014), Canada.
Zoltan et al., Role of Oxytocin in the Neuroadaptation to Drugs of Abuse, Psychoneuroendocrinology, vol. 19(1):85-117 (1994), U.S., Pergamon Press.
McGregor et al., Breaking the loop: Oxytocin as a potential treatment for drug addiction, Horm. Behav., pp. 9, (2011), Elsevier Press, Australia.
McGuire, William, Perinatal asphyxia, Clinical Evidence, 11:320 (2007), BMJ Publishing, Australia.
Hudak et al., Neonatal Drug Withdrawal, Pediatrics, 129;e54 (2012), American Academy of Pediatrics.

* cited by examiner

*Primary Examiner* — Maury A Audet

(57) ABSTRACT

Disclosed are oxytocin compositions having a therapeutically effective amount of oxytocin, an analog or derivative of oxytocin, or an oxytocin receptor agonist for the treatment of neonatal abstinence syndrome ("NAS") in a subject. Also disclosed are methods for the treatment of NAS by administering a therapeutically effective amount of oxytocin, an analog or derivative of oxytocin, or an oxytocin receptor agonist to a subject.

9 Claims, 32 Drawing Sheets

Specification includes a Sequence Listing.

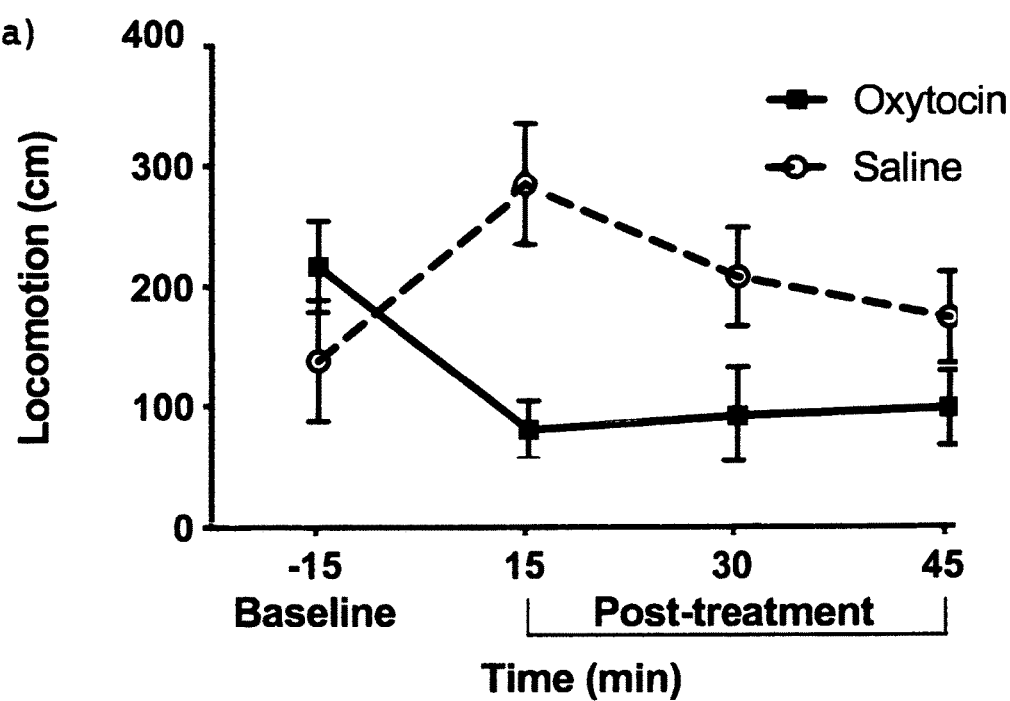

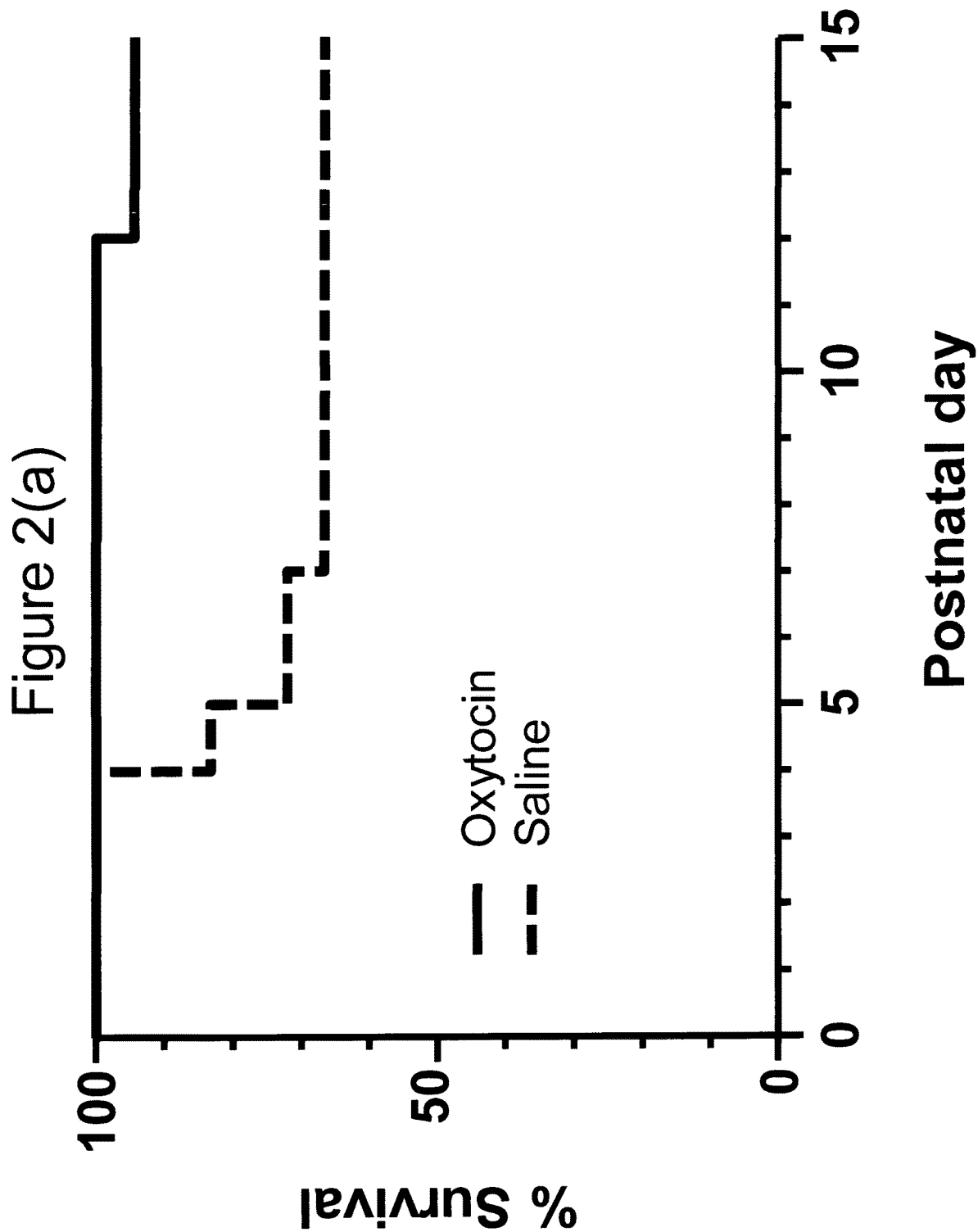

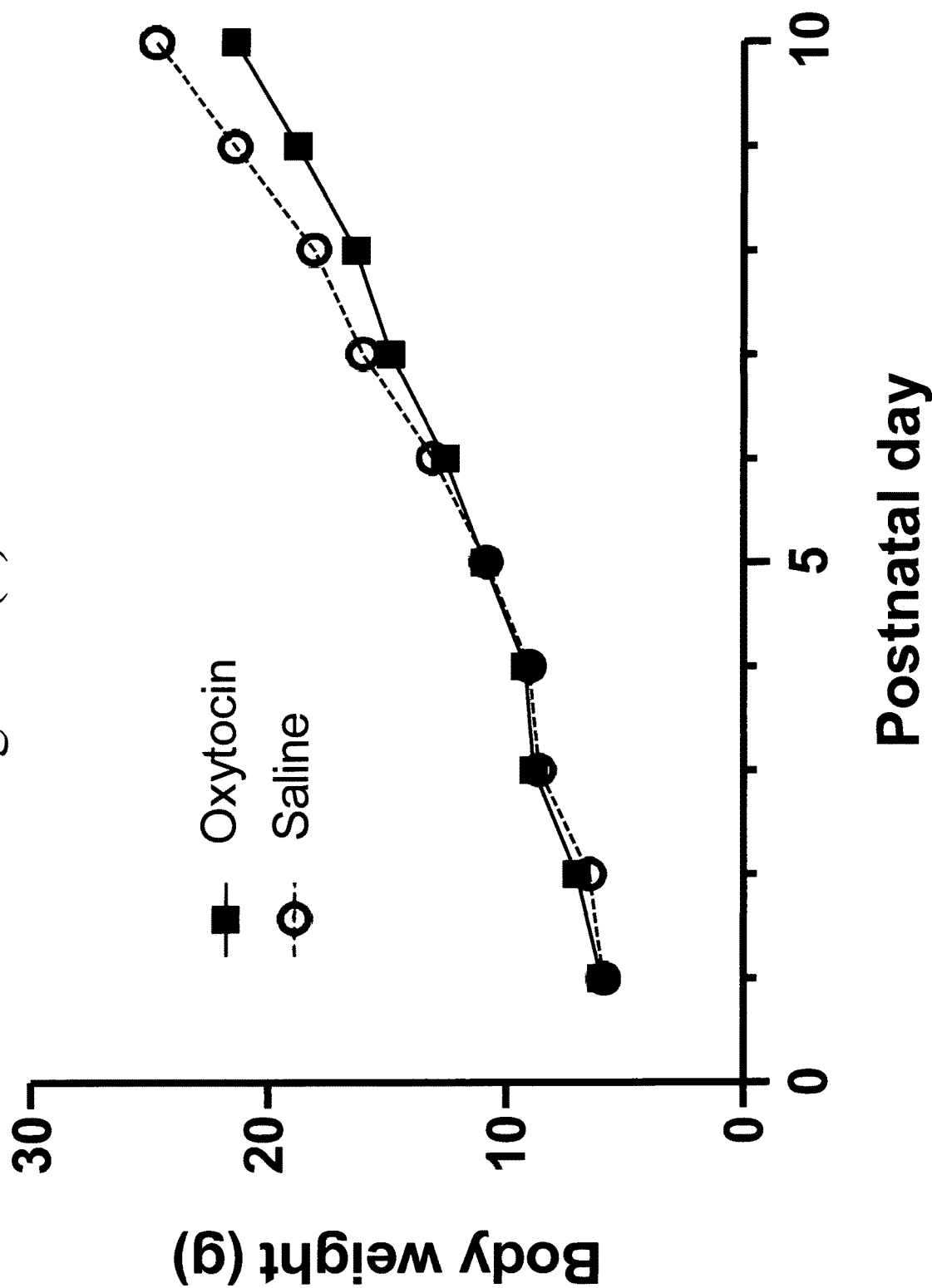

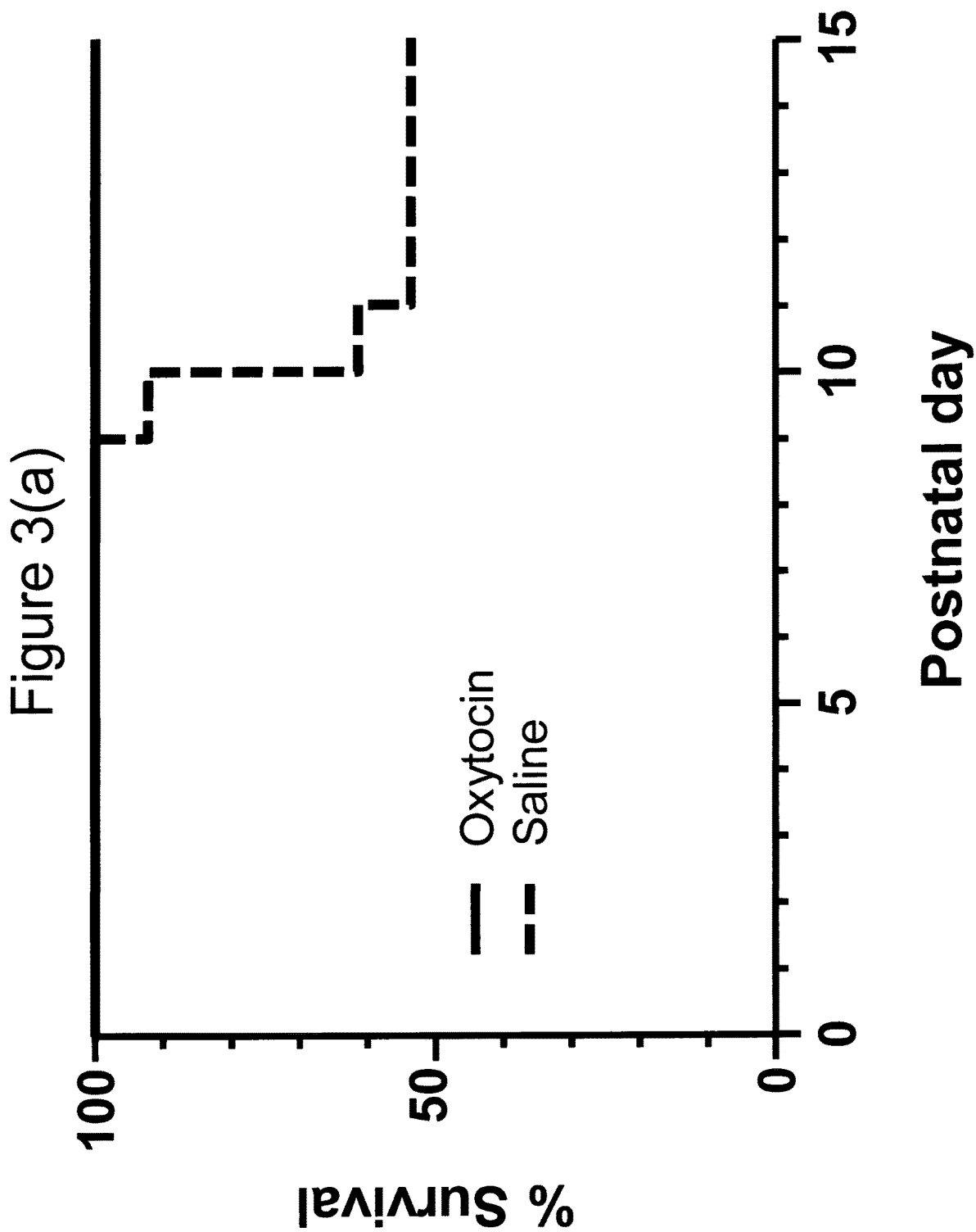

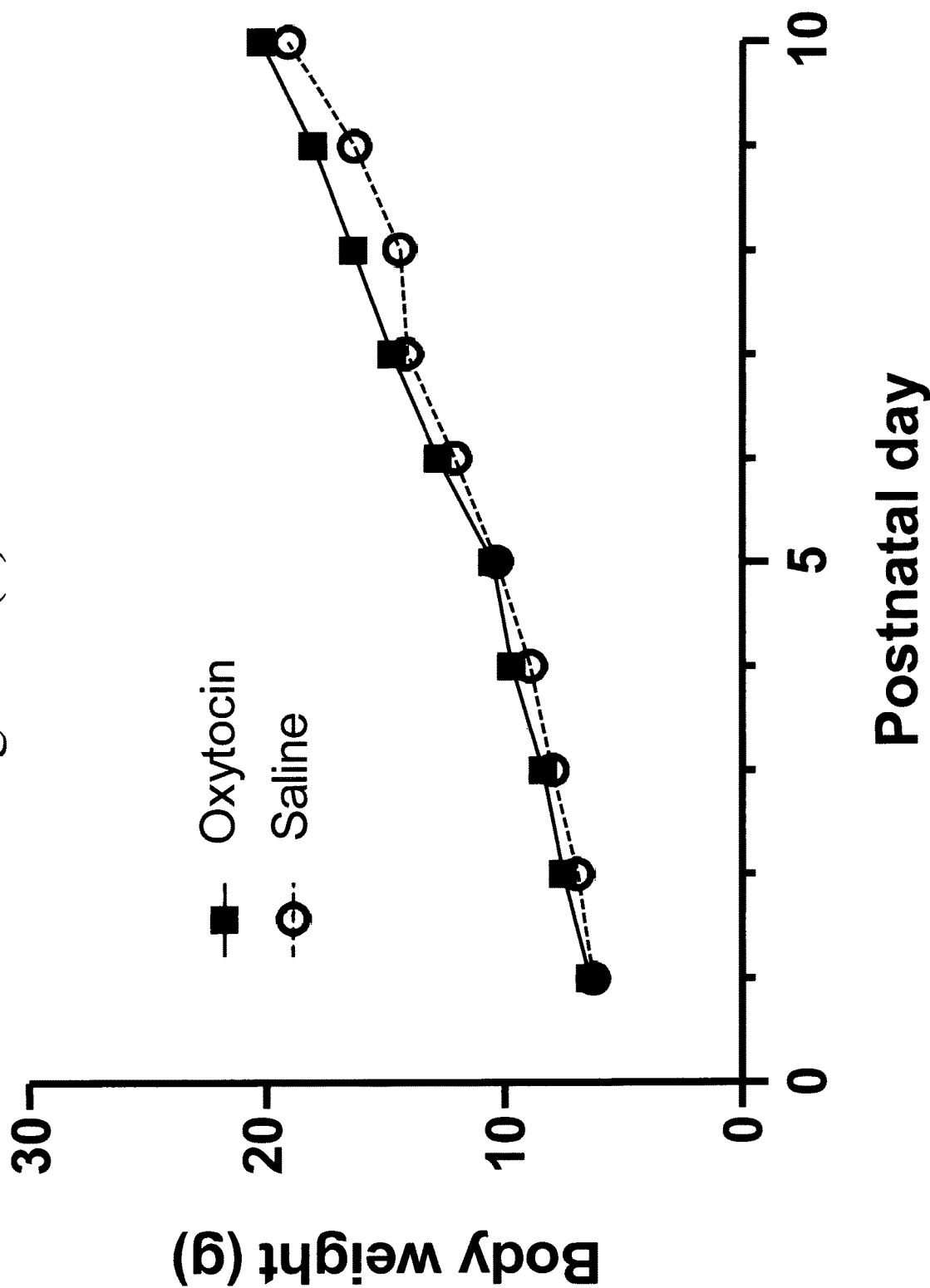

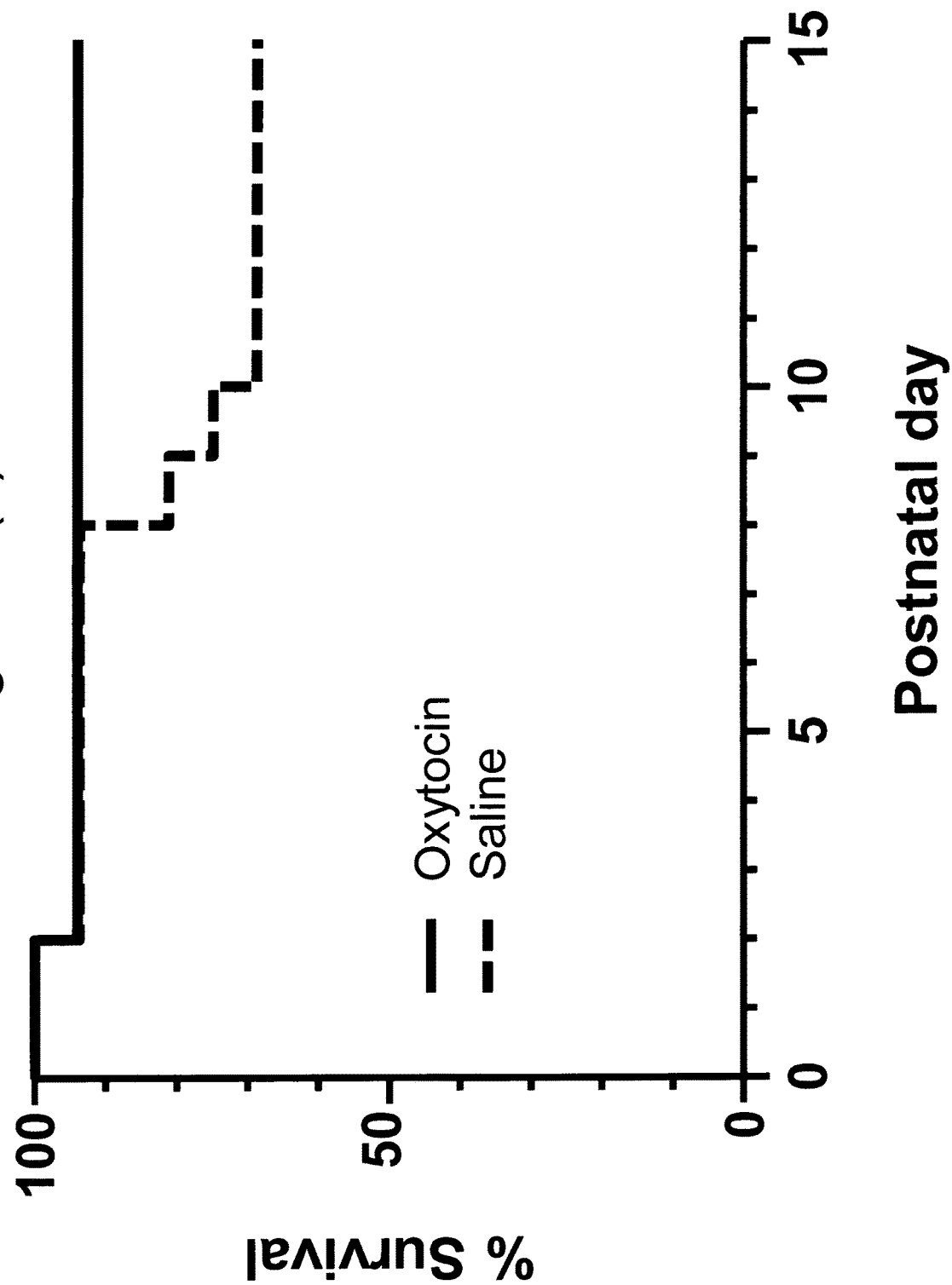

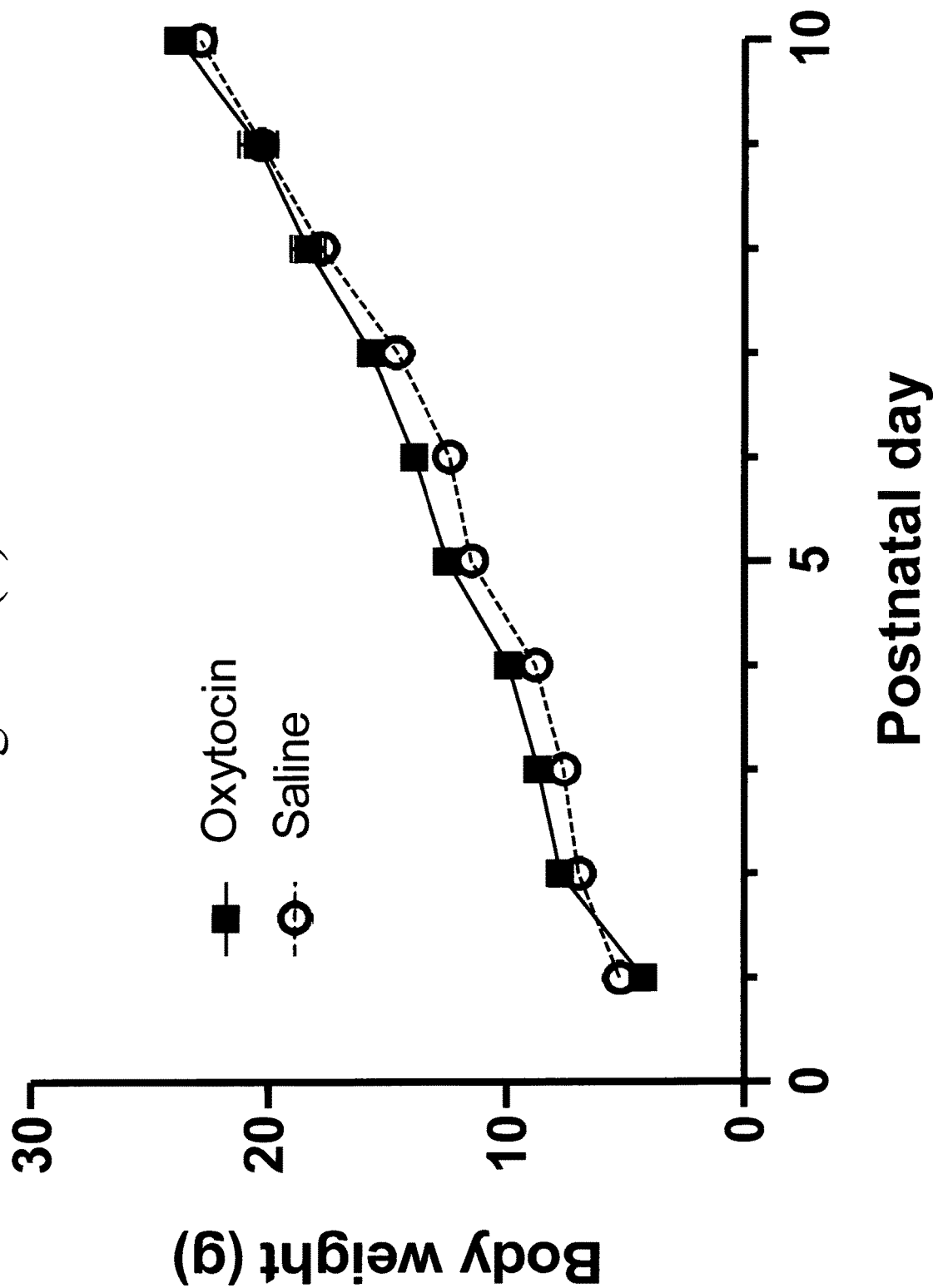

SEQUENCE LISTING

```
<160> NUMBER OF SEQ ID NOS: 4

<210> SEQ ID NO 1
<211> LENGTH: 9
<212> TYPE: PRT
<213> ORGANISM: Artificial
<220> FEATURE:
<223> OTHER INFORMATION: Synthetic

<400> SEQUENCE: 1

Cys Tyr Ile Gln Asn Cys Pro Leu Gly
1               5

<210> SEQ ID NO 2
<211> LENGTH: 8
<212> TYPE: PRT
<213> ORGANISM: Artificial
<220> FEATURE:
<223> OTHER INFORMATION: Synthetic

<400> SEQUENCE: 2
```

```
Cys Tyr Ile Gln Asn Cys Pro Leu
1               5

<210> SEQ ID NO 3
<211> LENGTH: 7
<212> TYPE: PRT
<213> ORGANISM: Artificial
<220> FEATURE:
<223> OTHER INFORMATION: Synthetic

<400> SEQUENCE: 3

Cys Tyr Ile Gln Asn Cys Pro
1               5

<210> SEQ ID NO 4
<211> LENGTH: 6
<212> TYPE: PRT
<213> ORGANISM: Artificial
<220> FEATURE:
<223> OTHER INFORMATION: Synthetic

<400> SEQUENCE: 4

Cys Tyr Ile Gln Asn Cys
1               5
```

OXYTOCIN COMPOSITIONS AND METHODS OF USE

CROSS-REFERENCE TO RELATED APPLICATIONS

This application claims the benefit of U.S. Provisional Application Ser. No. 62/654,776, filed Apr. 9, 2018; U.S. Provisional Application Ser. No. 62/741,422, filed Oct. 4, 2018; U.S. Provisional Application Ser. No. 62/767,268, filed Nov. 14, 2018; and U.S. Provisional Application Ser. No. 62/769,732, filed Nov. 20, 2018.

REFERENCE TO SEQUENCE LISTING, TABLE OR COMPUTER PROGRAM

The official copy of the Sequence Listing is submitted concurrently with the specification as an ASCII formatted text file via EFS-Web, with a file name of "SequenceListing," a creation date of Apr. 9, 2018, and a size of 848 bytes. The Sequence Listing filed via EFS-Web is part of the specification and is incorporated in its entirety by reference herein.

FIELD OF THE INVENTION

The present invention relates to compositions and methods employing oxytocin, an analog, a fragment or derivative of oxytocin, or an oxytocin receptor agonist for the management and/or treatment of neonatal abstinence syndrome ("NAS").

BACKGROUND OF THE INVENTION

The term "neonatal abstinence syndrome" ("NAS") was first described in the literature during the 1970s by Dr. Loretta Finnegan (LP Finnegan et al., *Addict Dis.*, 2:141-158 (1975)). Although NAS has been recognized for more than five decades, there have been substantial changes in the past 10 years, including a dramatic increase in prevalence and changes in both the exposure substance and clinical management (SW Patrick et al., *J. Perinatal*, 34:867-872 (2014) and FIG. 15). Notably, however, there has been little, if any, medical advancement associated with clinical management and treatment for those having been diagnosed with, determined to be suffering from or demonstrating symptoms and/or conditions evaluated as NAS. Although there has been scientific research on NAS, extensive treatment gaps exist, including a lack of clarity and consistency in how the syndrome is defined, measured, and managed. In addition, much of the research has focused on the infant in isolation from the mother, and many hospitals lack protocols to guide treatment. Subjects with NAS are known, inter alia, to have an increased incidence of agitation and irritability, respiratory symptoms, gastrointestinal distress, feeding difficulties, low birthweight, and seizures and death.

NAS has been recognized by the United States ("U.S.") government as a public health crisis and a growing body of governmental and foundation groups are committed to supporting the development of new treatments for this vulnerable patient population. Many US states are motivated to help find additional solutions to this issue given that state Medicaid programs cover approximately 80% of the treatment costs. Between 2004 and 2014, hospital costs totaled $2.5 billion for infants with NAS who were covered by Medicaid (Winkelman et al., *Pediatrics*, 141(4) (2018)). NICU admissions due to NAS have increased from 7 cases/1,000 admissions in 2004 to 27 cases/1,000 admissions in 2013 with an increase in the median length of hospital stay for infants with NAS from 13 to 19 days. The proportion of infants who received pharmacotherapy also increased, 74% in 2004-2005 to 87% in 2012-2013, resulting in a 35% increase in hospital costs. The current hospital costs associated with treating an infant withdrawing from drugs is estimated to be between $60,000 to $90,000, which is considerably more expensive than a hospital stay for a healthy newborn baby. Furthermore, the long-term costs associated with treating NAS may be in excess of $1,000,000 over an individual's life-time.

Between 2004 and 2014, NAS incidence rose over five-fold among infants covered by Medicaid. By 2014, NAS impacted 14.4 infants per 1000 births and totaled $462 million in hospital costs among Medicaid financed births. It is now estimated that a baby is born with NAS every 15 minutes and the current incidence rate is in excessive of 50,000 cases per year. This is consistent with the increased prevalence of NAS in other locations, including England, Canada and Western Australia, and reflects an increasing global problem. The increase in cases of NAS corresponds with the reported rise in drug use during pregnancy (RA Epstein et al., *Ann Epidemiol*, 23:498-503 (2013)), which is attributed to the more liberal use of prescribed drug agents and recreational use and abuse of illicit drug agents. For example, illicit use of opioids, such as oxycodone and heroin, and a dramatic increase in opioid-substitution programs for the treatment of opioid addiction. The pattern of opioid use has also shifted from an inner-city, low-income population to a more socioeconomically and demographically diverse population that includes pregnant women (NA Jumah, *Subst. Abuse*, 10:35-41 (2016)). The causes of NAS are similarly diverse, including, for example, in utero or prenatal exposure, to a variety of prescribed and illicit drugs as well as postnatal treatment of neonates with analgesic and sedative medications following surgical procedures.

At present, infants diagnosed with NAS that are in need of a pharmacological treatment are managed in a neonatal intensive care unit (NICU). Each year in the US, approximately 50,000 neonates receive inpatient pharmacotherapy for the treatment of NAS. Morphine and methadone have been the drugs of choice to treat infants where prenatal opioid exposure is the cause of the withdrawal syndrome. Morphine is given orally, typically every 3-4 h and the dose can be increased to obtain the desired effect. Morphine can be weaned every 24-48 hours. Methadone is also given orally every 4-12 hours and then weaned over time. However, the use of methadone is controversial due to its long half-life and prolonged excretion rate that could require longer hospitalization. Among infants with NAS, treatment with sublingual buprenorphine resulted in a shorter duration of treatment and shorter length of hospital stay than treatment with oral morphine, with similar rates of adverse events. It has been estimated that reducing the length of hospital stay by 2 days nationwide would result in a savings of an estimated $170 million in hospital charges (Gomez & Finnegan, *Front. Pediatr.*, 333(6) (2018)).

Clonidine eases the signs of NAS and does not include the narcotic effects of opioids. Phenobarbital, a γ-amino butyric acid agonist with sedative and anticonvulsant properties, has been used for years for the treatment of NAS. However, phenobarbital is most commonly used as an adjuvant therapy and not as a single-drug medication A review of the literature and current clinical treatment protocols for infants, and, in particular, neonates suffering from withdrawal resulting from prenatal or postnatal drug exposure, reveals there is a significant unmet need in the art for effective and efficient treatments for these neonates that does not involve a slow withdrawal process with an opioid or sedative agent or simply leaving these patients with no treatment options at all. The increased incidence of NAS and soaring increases in associated health care costs warrant a consistent and comprehensive approach to mitigating the negative outcomes for affected infants, their mothers, and the health care system.

Identification of novel pharmacotherapeutic strategies for NAS are urgently needed. In some recent literature, for example, Meguro et al., *J Pharmacol Sci,* 137:67-75 (2018)) suggest that oxytocin may function as a positive allosteric modulator that regulates the efficacy of the μ-opioid receptor ("MOR") signaling, and thus oxytocin might represent a previously unrecognized candidate analgesic agent. It has surprisingly been discovered herein, that compositions formulated with and methods set forth containing at least one oxytocin and/or oxytocin peptide, are able to provide effective and efficient treatment for neonatal abstinence syndrome, without the use of a slow weaning process using for example opioids or sedative drug agents. Additional analogues and derivatives of oxytocin may be found, for example, in Breton et al., *J. Biol. Chem.,* 276:26931-26941 (2001)).

Thus, there exists a dramatic unmet need in the art for treatment of NAS, which properties include, for example, the ability to reduce, minimize, ameliorate and/or eliminate the plethora of symptoms and/or conditions associated with NAS due to prenatal drug agent exposure and postnatal drug agent exposure.

SUMMARY OF THE INVENTION

In one aspect, the invention provides novel methods and compositions containing a therapeutically effective amount of oxytocin, such as (SEQ ID NO: 1 (Cys-Tyr-Ile-Gln-Asn-Cys-Pro-Leu-Gly)), an analogue or derivative of oxytocin, for example, carbetocin, an oxytocin receptor agonist or a fragment of oxytocin, identified herein as SEQ ID NO: 2, SEQ ID NO: 3 or SEQ ID NO:4, for treating subjects diagnosed with and/or suspected of having NAS, or suffering from symptoms and conditions associated with NAS.

In another aspect, prophylactic administration of the described compositions and methods is also envisioned; particularly in instances where medical staff are uncertain if symptoms of NAS, which may not be readily identifiable or present post-birth but suspect the neonate could be at risk of developing symptoms of NAS.

In some embodiments, the composition of the invention is adapted for intranasal administration, which includes any device capable of dispensing multiple or single/individual doses of the oxytocin composition to the nasal mucosa of a subject. Such devices are known, for example, in the disclosures of U.S. Pat. Nos. 9,579,280, 9,238,072, 9,186,320, 8,877,230, 8,874,882, 8,784,869 and US2011/0033544A1.

In other embodiments, the composition is adapted for intranasal administration, which may further contain a device for intranasal administration, such as a nasal pump apparatus, e.g., a nasal pump apparatus comprising a reservoir bottle attached to an aerosolizer. In some embodiments, the nasal pump apparatus comprises one of more of the following: (i) a filter for preventing back flow, (ii) a metal-free fluid path, and (iii) a plastic material stable to gamma-radiation. In some embodiments, the nasal pump apparatus provides a metered dose (e.g., about 0.01 μg to about 500 μg per spray). However, in another embodiment, the device is a single-use device providing a single-metered dose of oxytocin.

It should be appreciated that the invention further provides a plurality of administration methods for the compositions described herein. Administration and/or delivery routes include, but are not limited to intranasal; buccal, for example, U.S. Pat. No. 6,969,508, such as a buccal aerosol spray; oral, such as sublingual, see for example, U.S. Pat. No. 5,132,114; subcutaneous; topical; intramuscular; suppository, see for example, U.S. Pat. No. 6,740,333, and intravenous delivery. Optionally, the methods and compositions of the invention may be formulated with an alkaline earth metal, such as beryllium, magnesium, calcium, strontium, barium or radium or a salt thereof.

In one aspect, the invention provides methods and compositions for treating NAS by administering to a subject in need thereof a therapeutically effective amount of oxytocin in a pharmaceutically acceptable carrier. In some embodiments, the subject is a mammal and is a human subject. A subject may be a neonate, an infant, a child, an adolescent or an adult. A therapeutic effective amount, within a suitable therapeutic range detailed herein for a subject, may be selected by one skilled in the art.

In another aspect of the invention, oxytocin, an analog or derivative of oxytocin, or an oxytocin receptor agonist is provided as a dry powder, which can be hydrated for use at a suitable time period to be used in any of the routes of delivery described herein, for example, as an oral dosage, as an infusion, as an injectable dosage or as a nasal dosage.

In some embodiments, the analogue or derivative of oxytocin is carbetocin. Carbetocin may be any one of or a combination thereof, which is not limited to, 1-Butanoic acid-2-(O-methyl-L-tyrosine)-1-carbaoxytocin, 1-Butyric acid-2-(3-(P-methoxyphenyl)-L-alanine)oxytocin and Deamino-2-O-methyltyrosine-1-carbaoxytocin. Carbetocin, includes, for example, brand names, such as Duratocin, Pabal, Lonactene, Depotocin, Comoton, Decomoton, or 1-butanoic acid-2-(0-methy-L-tyrosine)-1-carbaoxytocin. Carbetocin is commercialized for obstetrics use in Canada and the United Kingdom and many other countries throughout the world, but not in the United States.

In another aspect of the invention, the compositions and methods may contain one or more excipients, vehicles, emulsifiers, stabilizers, preservatives, mucosal adhesives, antibacterial agents, buffers and/or other additives. Additionally, the invention envisions a composition that optionally contains an alkaline earth metal.

In some embodiments of the invention, the composition of the invention may be administered over a time period of hours, over a time period of days, over a time period of weeks, over a time period of months or over a time period of years to the subject. For example, the composition of the invention might be administered at any time upon birth (post-birth) as determined by a medical team and/or physician, be administered to the subject immediately upon birth, within about 1 hour post-birth, within about 24 hours post-birth, within about 36 hours post-birth, within about 48 hours post-birth, within about 72 hours post-birth, within about 96 hours post birth, within about 7 days post-birth (about a week), within about 10 days post-birth, within about 14 days post-birth, within about 30 days post-birth and continue for a time period up to about 30 days post-birth (about 1 month), up to about 45 days post-birth, up to about 60 days post-birth, up to about 3 months post-birth, up to about 6 months post-birth, up to about 12 months post-birth, up to about 18 months post-birth, up to about 24 months post-birth or more after the subject has been diagnosed with, suspected of having or determined to be suffering from neonatal abstinence syndrome.

In another aspect of the invention, the compositions and methods contain oxytocin in amounts determined to be necessary to provide effective treatment and/or prophylactic treatment to a subject to alleviate, minimize, reduce and/or eliminate the effects and/or symptoms of NAS. The proper dose and amounts of oxytocin may range from about 1 international unit ("IU") to about 100 IUs of oxytocin or more.

In another aspect of the invention, the composition is administered to a subject as an infusion, such as an intravenous drip, over a time period between about 1-hour post-birth to about 96 hours post-birth, after the subject has been diagnosed with, is determined to be suffering from the effects and/or symptoms of NAS or is suspected of having NAS or is at potential risk for developing NAS. Such intravenous treatment to the subject includes treatment of up to about 3 days, up to about 1 week, up to about 10 days, up to about 14 days, up to about 30 days, up to about 45 days, up to about 60 days, up to about 90 days or more.

In other embodiments of the invention, the compositions and methods optionally contain magnesium or a magnesium salt. In some embodiments, the magnesium salt is magnesium citrate and/or magnesium chloride. In some embodiments, provided is a composition comprising an oxytocin formulation or composition and a magnesium salt, and a pharmaceutically acceptable carrier, wherein the oxytocin and the magnesium salt are in an amount that produces a synergistic effect when used in the treatment of NAS.

In another aspect of the invention, the composition typically exhibits a pH of between about 3.0 and about 8.5. In some aspects of the invention, the composition of the invention has a pH of between about 4.5 to about 6.5.

The present invention also provides an embodiment wherein the components and/or compositions for practicing the invention can be conveniently provided in a kit. In its simplest embodiment, a kit of the invention provides a set number of predetermined doses, wherein the dosages are set according to the needs of the subject.

In yet other embodiments of the invention, a subject may be of any age, such as a neonate, an infant, toddler, child, pre-teen, preadolescent, adolescent or other individual with a developing, growing, reorganizing or remodeling nervous system. Thus, administration of the compounds and compositions of the invention is well suited for subjects having, diagnosed with or suspected of having diseases, disabilities, disorders or conditions that are caused by, are characterized by, or otherwise associated with exposure to a drug agent in utero.

The present invention provides pharmaceutical compositions comprising at least one oxytocin, carbetocin, an oxytocin receptor agonist, a derivative or analogue of oxytocin or a fragment of oxytocin that may be mixed with other active ingredients or pharmaceutically acceptable carriers. Advantageously, the compositions of the invention are formulated to permit their uptake into the blood stream and/or nervous system and/or passage into the nervous system.

Further provided are implantable sustained release formulations containing at least one oxytocin, carbetocin, an oxytocin receptor agonist or a fragment of oxytocin that are also useful embodiments of the pharmaceutical compositions of the invention. For example, the pharmaceutically acceptable carrier, being a biodegradable matrix implanted within the body or under the skin of a human can be a hydrogel. Alternatively, it may be formed from a poly-alpha-amino acid component. Other techniques for making implants for delivery of drugs are also known and useful in accordance with the invention.

Pulmonary delivery of the inventive compositions is also useful. The at least one oxytocin, carbetocin, an oxytocin receptor agonist or a fragment of oxytocin is delivered to the lungs of a mammal while inhaling and traverses across the lung epithelial lining to the blood stream. A wide range of mechanical devices designed for pulmonary delivery of therapeutic products, including but not limited to nebulizers, metered dose inhalers, and powder inhalers, all of which are familiar to those skilled in the art may be employed. All such devices require the use of formulations suitable for the dispensing of the inventive compound. Typically, each formulation is specific to the type of device employed and can involve the use of an appropriate propellant material, in addition to diluents, adjuvants and/or carriers useful in therapy. The use of liposomes, microcapsules or microspheres, inclusion complexes, or other types of carriers is contemplated.

In some embodiments, a pharmaceutical composition comprising at least one oxytocin, carbetocin, an oxytocin receptor agonist, a derivative or analogue of oxytocin, or a fragment of oxytocin is configured as a part of a pharmaceutically acceptable transdermal or transmucosal patch or a troche. Transdermal patch drug delivery systems, for example, matrix type transdermal patches, are known and useful for practicing T-sonic transdermal patch embodiments of the present pharmaceutical compositions.

Medical devices suitable for single, metered, depot, or continuous administration of compositions according to the invention are also contemplated. A device may be designed or adapted to control, meter, measure a precise volume or amount of at least one oxytocin, carbetocin, an oxytocin receptor agonist, a derivative or analogue of oxytocin, or a fragment of oxytocin. It may also be designed or adapted to administer the oxytocin, carbetocin, an oxytocin receptor agonist or a fragment of oxytocin to a subject prophylactically or deemed at risk for developing symptoms and/or conditions associated with biological exposure to at least one drug agent. Such devices or compositions may be included in a kit that includes packaging materials or instructions for use.

In certain embodiments of the invention, the incidence of negative effects, conditions, symptoms or disabilities, including cognitive development issues, neurodevelopmental indications in a subject associated with biological exposure to at least one drug agent is ameliorated, reduced or eliminated. A subject may be of any age, such as first, a neonate, toddler, child, pre-teen, preadolescent, adolescent or other individual.

Patents, patent applications, publications, procedures, and the like are cited throughout this application, the disclosures of which are incorporated herein by reference in their entireties.

BRIEF DESCRIPTION OF THE FIGURES

FIGS. 1a, 1b, 1c and 1d: Oxytocin reduces naloxone-induced withdrawal symptoms in rat pups chronically exposed to morphine prenatally.

FIGS. 2a, 2b and 2c: Neonatal oxytocin treatment reduces mortality in rat pups chronically exposed to morphine prenatally.

FIGS. 3a, 3b and 3c: Neonatal oxytocin treatment reduces mortality in rat pups chronically exposed to diazepam prenatally.

FIGS. 4a, 4b and 4c: Neonatal oxytocin treatment reduces mortality in rat pups chronically exposed to fluoxetine prenatally.

DETAILED DESCRIPTION OF THE INVENTION

Figure 1B:
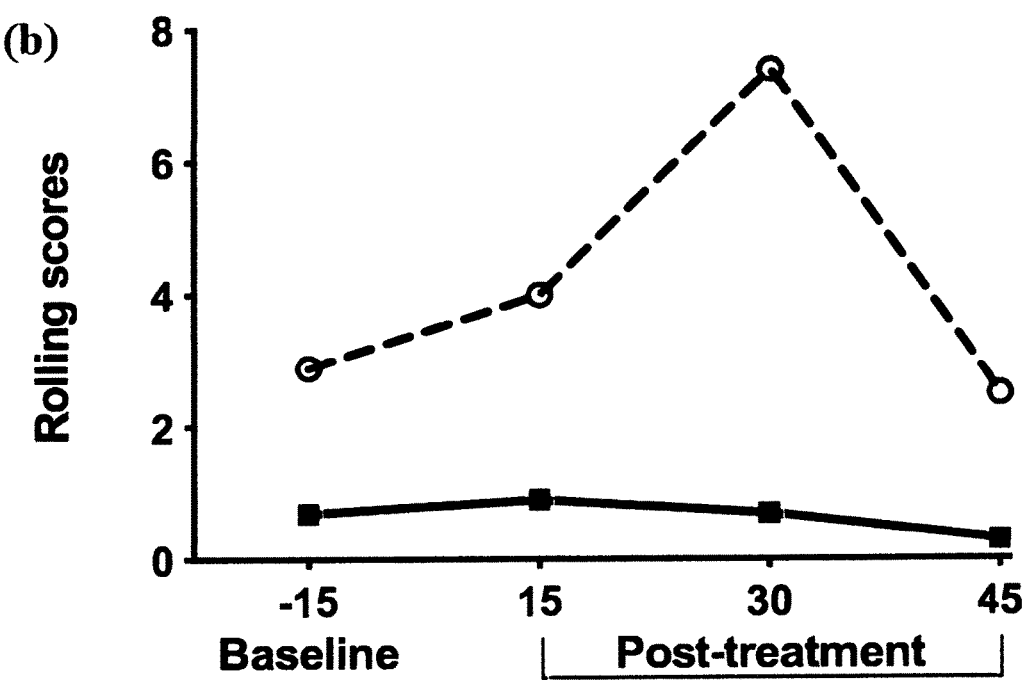

The present invention is not to be limited in scope by the specific embodiments described herein. Indeed, various modifications of the invention in addition to those described herein will become apparent to those skilled in the art from the following description and the accompanying Figures. Such modifications are intended to fall within the scope of the appended claims. It is further to be understood that values are approximate and are provided for description. The invention further includes combinatorial fusion of the sequences described herein. Such fusions may be performed using standard molecular biology techniques or by chemical synthesis such as peptide synthesis. Further modifications to oxytocin, carbetocin, an oxytocin receptor agonist or a fragment of oxytocin or other derivatives or analogs include addition of linker peptides, effector moieties, or other covalent modifications, such as insertion or addition of non-natural amino acids (e.g., D-amino acids, or D- or L-amino acids other than the conventional twenty amino acids), use of modified or functionalized amino acids, or replacement of amino acids in the sequence with other chemical compounds.

Definitions

As used herein, "Neonatal Abstinence Syndrome" or "NAS", is a term employed for a collection of health issues and/or health problems a neonate experiences when withdrawing from exposure to a drug agent, such as, opioids. This exposure to a drug agent includes both prenatal exposure, for example, in utero, and postnatal exposure, which may result in an "iatrogenic disorder or syndrome." In addition to the specific difficulties of withdrawal after birth, problems in the neonate may include, but are not limited to, for example, poor intrauterine growth, premature birth, seizures and birth defects. Specific drugs often cause specific problems in the neonate and may include, for example, heroin and other opiates, including methadone and buprenorphine, amphetamines, cocaine, alcohol, and marijuana and can cause significant withdrawal in the neonate, with some symptoms lasting as long as four to six months. Symptoms of withdrawal may include, but are not limited to, tremors (trembling), irritability (excessive crying), sleep problems, high pitched crying, tight muscle tone, hyperactive reflexes, seizures, yawning, stuffy nose and sneezing, poor feeding and suckling, vomiting, diarrhea, dehydration, sweating, fever or unstable temperature. If left untreated, babies will often die from NAS. Other terms may also be used to describe the syndrome, including neonatal withdrawal syndrome, neonatal drug withdrawal syndrome, neonatal opioid withdrawal syndrome, and neonatal withdrawal. These terms are also suitable for the claimed invention.

"Iatrogenic disorder" or "iatrogenic syndrome" and/or "iatrogenic disease" typically are the result of diagnostic and therapeutic procedures undertaken on a subject, such as, a neonate following birth, i.e., postnatal. Depending on the indications and/or issues noted, perceived or diagnosed by a medical team at birth, a multitude of drugs may be employed to a subject and adverse drug reactions may be observed in the subject.

As used herein, an "opioid" or "opioid drug agent," includes, but is not limited to: codeine, fentanyl(Actiq, Duragesic, Fentora, Abstral, Onsolis), carfentanil, sufentanil, alfentanil, remifentanil, hydrocodone (Hysingla, Zohydro ER), hydrocodone/acetaminophen (Lorcet, Lortab, Norco, Vicodin), hydromorphone (Dilaudid, Exalgo), Meperidine (Demerol), tramadol, heroin, methadone (Dolophine, Methadose), morphine (Kadian, MS Contin, Morphabond), oxycodone (OxyContin, Oxaydo), oxycodone and acetaminophen (Percocet, Roxicet), oxycodone and naloxone, meloxicam, kratom, Opana and Opana ER.

As used herein, a "non-opioid" or "non-opiate analgesic" or "a non-opioid or non-opiate analgesic drug agent" includes, but is not limited to: NSAIDS, Cox 1 and Cox 2 inhibitors, acetaminophen, ibuprofen, aspirin, naproxen diclofenac, bromfenac, diflunisal, etodolac, fenoprofen, flurbiprofen, indomethacin, ketoprofen, ketorolac, meclofenamate, mefenamic acid, meloxicam, nabumetone, nepafenac, oxaprozin, phenylbutazone, piroxicam, sulindac, tolmetin, butalbital, caffeine, celecoxib and combinations of these agents.

As used herein, an "anxiolytic or sedative" or "anxiolytic and sedative drug agent" includes, but is not limited to sedatives, utilized during pregnancy, and non-benzodiazepine hypnotic drug agents or "Z-drugs," for example: zolpidem (Ambien®), eszopiclone (Lunesta®), zaleplon (Sonata®) and zopiclone. Other drug agents include, for example: Benzodiazepines, such as alprazolam (Xanax®), bromazepam (Lectopam®, Lexotan®), chlordiazepoxide (Librium®), clonazepam (Klonopin®, Rivotril®), clorazepate (Tranxene®), diazepam (Valium®), flurazepam (Dalmane®), lorazepam (Ativan®), temazepam (Restoril®), triazolam (Halcion®), tofisopam (Emandaxin® and Grandaxin®), carbamates such as meprobamate (Miltown®, Equanil®), carisoprodol, tybamate, lorbamate, xazepam (Serax®, Zaxopam®, Serapax®), clobazam (Onfi®), estazolam (Prosom®), flurazepam (Dalmane®), midazolam (Versed®), temazepam (Restoril®), bromazepam (Lectopam®, Lexotan®), beta-blockers, such as propranolol and oxprenolol, barbiturates, alpha blockers, such as prazosin, alpha adrenergic agonists, such as clonidine and guanfacine, and antihistamines, such as hydroxyzine.

Other "anxiolytic or sedative" or "anxiolytic or sedative drug agents" include, but are not limited to: phenibut, mebicar, fabomotizole, selank, bromantane, eoxypine, azapirones, menthyl-isovalerate, propofol, racetams and inhalants.

As used herein, an "antidepressant" or an "antidepressant drug agent" includes, but is not limited to: SSRIs, SNRIs, tricyclic antidepressants ("TCAs"), monoamine oxidase inhibitors ("MAOIs") and atypical antidepressants.

As used herein, a "stimulant" or "psychostimulant" or "psychostimulant drug agent" includes, but is not limited to: cocaine, 3,4 methylenedioxymethamphetamine (ecstasy or MDMA), propylhexedrine, *Catha edulis*, methylenedioxypyrovalerone, mephedrone, kratom, isoproterenol, epinephrine, norepinephrine, phenylpropanolamine, apomorphine, methamphetamine, phenmetrazine, pipradol, tyramine, pemoline, caffeine, nicotine, scopolamine, strychnine, pentylenetetrazol, modafinil, dextroamphetamine (Adderall® and Adderall® XR, Procentra®, Zenzedi®), methylphenidate (Concerta®, Ritalin®, Ritalin® LA and Ritalin® SR, Methylin® and Methylin® ER, Metadate® CD and Metadate® ER, Aptensio® XR, Cotempla® XR-ODT XR, Daytrana®, Quillichew® ER and Quillichew® XR), dextroamphetamine (Dexedrine®), atomoxetine (Strattera®), lisdexamfetamine (Vyvase®), dexmethylphenidate (Focalin® and Focalin® XR), amphetamine sulfate (Evekeo®), amphetamine (Adzenys® XR-ODT, Dyanavel® XR, Mydayis®), oxymetazoline (Afrin®, Dristan®, Vicks®, Sinex®), pseudoephedrine (Sudafed®, Suphedrin®, Silfedrine®), phenylephrine (Suphedrin® PE, Sudafed® PE).

As used herein, an "anticonvulsant agent" or "anticonvulsant drug agent," includes, but is not limited to: acetazolamide, carbamazepine, clobazam, clonazepam, diazepam, ethosuximide, gabapentin, lamotrigine, levetiracetam, lorazepam, nitrazepam, oxcarbazepine, phenobarbital, phenytoin, pregabalin, primidone, rufinamide, stiripentol, topiramate, valproic acid, vigabatrin, sabril, felbamate, tiagabine hydrochloride and zonisamide.

As used herein, a "sympatholytic" or "sympatholytic drug agent" includes, but is not limited to: metoprolol, atenolol, sotalol, propranolol, nadolol, nebivolol, bisoprolol, timolol, carvedilol, acebutolol, betaxololm and labetalol.

As used herein, "biologically exposed" and "biological exposure" to a drug agent, includes, but is not limited to a passive in utero exposure and/or administration of a drug agent to a subject during a mother's pregnancy, i.e., the mother has ingested the drug agent via any route of administration of a drug agent, direct or intentional in utero exposure of a drug agent to the subject during a mother's pregnancy, postnatal administration and/or application of the drug agent to the subject for any reason, for example, pain relief for the subject due to an invasive and/or non-invasive surgical procedure performed on the subject.

As used herein, "improved survival rate" and "reduced mortality rate," refers to the survival outcome (verses death outcome) for subjects receiving and/or provided the oxytocin compositions and methods of the invention herein. When NAS was first identified, no pharmacological treatments existed, and the subjects died. Once the condition was recognized to be caused by the interruption of placental supply of in particular opioids, pharmacological interventions were introduced resulting in improvement of the survival rates. Currently, the most common medications used to treat NAS are morphine, methadone, buprenorphine, phenobarbital, and clonidine. (see, for example, Gomez-Pomar et al., *Front. Pediatr.*, 6:33 (2018)).

As used herein "improved cognitive abilities" refers to a subject's general mental capability involving reasoning, problem solving, planning, abstract thinking, complex idea comprehension, memory and learning from experience. Subjects exposed to drug agents prenatally may experience impairments in their cognitive ability during childhood, adolescence or adulthood, such as emotion processing, social behavior, psychomotor functioning, and learning and memory. Data provided herein, demonstrates that treatment with the oxytocin compositions and methods of the invention, improves cognitive, emotional, motor and social functioning as measured by the Passive Avoidance Task, Light-Dark Box Test, Locomotor Assay, and Social Novelty and Social Memory Tests, respectively.

As used herein "improved neurodevelopmental outcomes" refers to functional abnormalities that may not be detected at birth but later in childhood, adolescence or adulthood. Most frequent manifestations of injury to the developing central nervous system do not typically result in nervous system malformations but in functional abnormalities resulting from a subject's prenatal exposure to a drug agent. This drug agent exposure can affect neurodevelopmental outcomes resulting in impairments to cognitive, emotional, motor and social functioning. (see, for example, Henrietta S. Bada, MD, MPH, slide presentation, Department of Pediatrics, College of Medicine, University of Kentucky).

"Optional" or "optionally" as used herein, means that the subsequently described element, component or circumstance may or may not occur, so that the description includes instances where the element, component, or circumstance occurs and instances where it does not.

The term "about," particularly in reference to a given quantity, is meant to encompass deviations of plus or minus five percent.

As used herein, an "analogue," or "derivative" refers to any oxytocin peptide analogous to naturally occurring oxytocin wherein one or more amino acids within the peptide have been substituted, deleted, or inserted. The term also refers to any oxytocin peptide wherein one or more amino acids (for example one, two or three amino acids) have been modified, for example by chemical modification. In general, the term covers all peptides which exhibit oxytocin activity, but which may, if desired, have a different potency or pharmacological profile.

As used herein, the term "composition," or "pharmaceutical composition" refers to a mixture of at least one compound useful within the invention with a pharmaceutically acceptable carrier. The pharmaceutical composition facilitates administration of the compound to a patient, individual or subject. Multiple techniques of administering a compound exist in the art including, but not limited to, mucosal, which includes, for example, nasal/intranasal, aerosol, buccal, sublingual and ocular; oral, which includes, for example, liquid; subcutaneous delivery; topical, which includes for example, gels and transdermal patches; intramuscular; suppository and intravenous delivery.

A "therapeutic" treatment is a treatment administered to a subject, patient, individual who exhibits signs of pathology, for the purpose of diminishing, minimizing, moderating and/or eliminating those signs.

As used herein, the term "treat," "treatment," or "treating" is defined as the application or administration of a therapeutic agent, i.e., a compound of the invention (alone or in combination with another pharmaceutical agent), to a subject, patient, individual, or application or administration of a therapeutic agent to an isolated tissue or cell line from a subject (e.g., for diagnosis or ex vivo applications), who has a condition contemplated herein, a symptom of a condition contemplated herein or the potential to develop a condition contemplated herein, with the purpose to cure, heal, alleviate, relieve, alter, remedy, ameliorate, improve or affect a condition contemplated herein, the symptoms of a condition contemplated herein or the potential to develop a condition contemplated herein. Such treatments may be specifically tailored or modified, based on knowledge obtained from the field of pharmacogenomics.

As used herein, the terms "effective amount," "pharmaceutically effective amount," and "therapeutically effective amount" refer to a nontoxic but sufficient amount of an agent to provide the desired biological result. That result may be reduction and/or alleviation of the signs, symptoms, or causes of a disease, or any other desired alteration of a biological system. An appropriate therapeutic amount in any individual case may be determined by one of ordinary skill in the art using routine experimentation.

As used herein, the term "pharmaceutically acceptable" refers to a material, such as a carrier or diluent, which does not abrogate the biological activity or properties of the compound, and is relatively non-toxic, i.e., the material may be administered to a subject, patient and/or individual without causing undesirable biological effects or interacting in a deleterious manner with any of the components of the composition in which it is contained.

As used herein, the language "pharmaceutically acceptable salt" refers to a salt of the administered compounds prepared from pharmaceutically acceptable non-toxic acids, including inorganic acids, organic acids, solvates, hydrates, or clathrates thereof. Examples of such inorganic acids are hydrochloric, hydrobromic, hydroiodic, nitric, sulfuric, phosphoric, acetic, hexafluorophosphoric, citric, gluconic, benzoic, propionic, butyric, sulfosalicylic, maleic, lauric, malic, fumaric, succinic, tartaric, amsonic, pamoic, p-toluenesulfonic, and mesylic. Appropriate organic acids may be selected, for example, from aliphatic, aromatic, carboxylic and sulfonic classes of organic acids, examples of which are formic, acetic, propionic, succinic, camphorsulfonic, citric, fumaric, gluconic, isethionic, lactic, malic, mucic, tartaric, para-toluenesulfonic, glycolic, glucuronic, maleic, furoic, glutamic, benzoic, anthranilic, salicylic, phenylacetic, mandelic, embonic (pamoic), methanesulfonic, ethanesulfonic, pantothenic, benzenesulfonic (besylate), stearic, sulfanilic, alginic, galacturonic, and the like. Furthermore, pharmaceutically acceptable salts include, by way of non-limiting example, alkaline earth metal salts (e.g., calcium or magnesium), alkali metal salts (e.g., sodium-dependent or potassium), and ammonium salts.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the subject such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations.

As used herein, "pharmaceutically acceptable carrier" also includes any and all coatings, antibacterial and antifungal agents, and absorption delaying agents, and the like that are compatible with the activity of the compound useful within the invention and are physiologically acceptable to the patient. Supplementary active compounds may also be incorporated into the compositions. The "pharmaceutically acceptable carrier" may further include a pharmaceutically acceptable salt of the compound useful within the invention. Other additional ingredients that may be included in the pharmaceutical compositions used in the practice of the invention are known in the art and described, for example in Remington's Pharmaceutical Sciences (Genaro, Ed., Mack Publishing Co., (1985)), which is incorporated herein by reference.

An "effective amount" of a delivery vehicle is that amount sufficient to effectively bind or deliver a compound.

A "subject," "individual," or "patient" as used herein refers to a mammal, including but not limited to a human. Mammals include, but are not limited to, farm animals (such as cows), sport animals, pets (such as guinea pigs, cats, dogs, rabbits and horses), primates, mice and rats. In one embodiment, a subject is a human. In another embodiment, the human is a neonate, a child, an adolescent or an adult.

"Intranasal administration," or "administered intranasally" refers to delivery to the nose, nasal passageways or nasal cavity by spray, drops, powder, gel, film, inhalant or other means.

As used herein, "q.d.," "qd," or "QD" means one-a-day or once-daily administration or delivery of a composition and/or drug.

"b.i.d., or "BID" is understood to mean twice a day administration or delivery of a composition and/or drug.

"t.i.d.," or "TID" means three times a day administration or delivery of a composition and/or drug.

"q.i.d.," or "QID" is understood to mean four times a day administration or delivery of a composition and/or drug.

"q_h" is understood to mean a composition and/or drug is to be taken every so-many hours, it is typically written as "q_h" wherein the "q" stands for "quaque" and the "h" indicates the number of hours. So, for example, "2 doses q4h" means "administer or take 2 doses every 4 hours."

"q.a.d.," is understood to mean every other day administration or delivery of a composition and/or drug.

"q.l.," and "q.s.," are understood to mean as much as a subject needs, requires or suffices of a composition and/or drug.

"p.r.n." or "PRN," refers to the administration of prescribed medication whose timing is left to the patient, doctor, nurse or caregiver, as opposed to medication that is to be taken according to a fixed "scheduled dosage."

"Synergism," "synergy" or "synergistic effect" refers to a joint action of two or more components in such a manner that one supplements or enhances the action of the other to produce an effect greater than that which would be predicted or expected by adding the effects of given doses of two or more components if given individually.

As used herein, a "neonate," or "newborn infant" is a subject from the time of birth through about the first month of life. At birth, the gestational age, as well as birth weight, is assessed, and the neonate classified accordingly; for example, as a large for gestational age neonate, a preterm or premature neonate, or a low birth weight neonate.

The term "infant" as used herein, is meant to mean a human child from birth to the end of the first year of life. Development of muscular control proceeds from the head downward (cephalocaudal development). The infant controls the head first and gradually acquires the ability to control the neck, then the arms, and finally the legs and feet. Movements are general and random at first, beginning with the use of the larger muscles and progressing to specific smaller muscles, such as those needed to handle small objects. Factors that influence growth and development are hereditary traits, sex, environment, nationality, race and physical makeup.

A "large-for-gestational age infant" is typically a preterm, term or post term infant who is above the $90^{th}$ percentile for gestational age in head circumference, body weight or length.

A "low-birth weight infant" is typically defined as one that weighs less than about 2500 grams at birth. This standard is routinely used for infants in developed countries, but infants born in other countries typically weigh less at birth. In India, for example, the criterion for normal birthweight is about 2150 grams and in Malaysia the criterion for normal birth weight is about 2000 grams.

A "premature infant," or "preterm infant" is one born before a gestational age of about 37 completed weeks (about 259 days). The duration of gestation is measured from the first day of the last menstrual period and is expressed in completed days or weeks.

A "post-mature infant," or "post-term infant" is typically recognized as one born any time after the beginning of about the forty-second week (about 288 days) of gestation.

A "small-for-gestational-age infant" means an infant a preterm, term or post-term infant who is below about the $10^{th}$ percentile for gestational age in head circumference, body weight, or length.

A "term infant" is one born at a gestational age of about 37 to about 42 completed weeks (about 259 to about 293 completed days).

A "very-low-birth-weight infant" is one born that weighs less than about 1000 grams at birth.

As used herein, "oxytocin," or "oxytocin peptide" refers to a substance having biological activity associated with natural oxytocin. Oxytocin (SEQ ID NO. 1) can be a naturally occurring endogenous peptide, fragments (SEQ ID NO. 2, SEQ ID NO. 3 and SEQ ID NO. 4), analogues or derivatives thereof. Oxytocin can also be a non-endogenous peptide, fragments, analogues or derivatives thereof. Oxytocin was one of the first peptide hormones to be isolated and sequenced. Natural oxytocin is a nine amino acid cyclic peptide hormone with two cysteine residues that form a disulfide bridge between positions 1 and 6. The amino acid sequence for human oxytocin is Cys-Tyr-Ile-Gln-Asn-Cys-Pro-Leu-Gly (SEQ ID NO:1). In one aspect, the oxytocin peptide is human oxytocin. In other aspects, oxytocin may be an analogue or derivative of human oxytocin, such as carbetocin.

An "international unit" (IU, UI or IE) is an internationally accepted unit of activity. It defines the amount of a substance that gives a unit of activity as determined using a defined biological assay in order to standardize preparations from multiple source materials. Similarly, a USP unit is a defined dosage unit established by the United States Pharmacopeia in cooperation with the Food and Drug Administration in order to ensure the identity, strength, quality, purity and consistency of a drug product. In general, USP units are equal to International Units, due to harmonization efforts. By convention, for oxytocin, 1 unit of activity is generally defined as equal to approximately 2 micrograms of synthetic oxytocin peptide; or 1 mg is equal to 500 units (Stedman's Medical Dictionary). Therefore, as used herein, one "IU" or "International Unit" of an oxytocin peptide is the amount of the oxytocin peptide that has the same biological activity or produces the same level of a biological effect (e.g. contractile response of rat uterine strips) as approximately 2 micrograms of the synthetic peptide. An analogue with weaker activity would require more material to achieve the same level of biological effect. Determinations of drug potency are well known to those skilled in the art and may include either in vitro or in vivo assays using synthetic oxytocin as a reference (Engstrom et al., *Eur J Pharmacol:* 355(2-3): 203-10 (1998)).

"Carbetocin" functions as an agonist at peripheral oxytocin receptors, particularly in the myometrium, with lesser affinity for myoepithelial cells. Oxytocin receptors are G protein-coupled and their mechanism of action involves second messengers and the production of inositol phosphates. Carbetocin mimics this mechanism. Binding for carbetocin and other oxytocin agonists has been shown to be nonselective at the extracellular N-terminus and loops E2 and E3. Although the oxytocin receptor shows equal affinity for oxytocin and carbetocin, the biological effect of carbetocin is almost 50% that of endogenous or exogenous oxytocin. Carbetocin has a much longer lasting effect than oxytocin, necessitating, at times, only a single dose. Carbetocin inhibits endogenous oxytocin release, interrupting the uterine feedback loop with the hypothalamus and decreasing both central and peripheral release of oxytocin. Carbetocin, either alone, in combination with one or more additionally agents, and/or present in a formulation, is typically refrigerated and maintained at a temperature at or below about 4° C.

As used herein the term "Finnegan," "Finnegan score," and "Finnegan scale" refer to a system developed by Dr. Loretta P. Finnegan. The Finnegan scale is based on 21 symptoms of neonatal drug withdrawal, such as opioid withdrawal, which include tremors, seizures, excessive crying, diarrhea, vomiting, congestion, sneezing and other symptoms that can make it difficult for a newborn to eat and sleep. The score monitors the passively addicted infant in a more comprehensive and objective fashion and facilitates a more precise evaluation of the clinical status of the infant undergoing withdrawal. In addition, the scoring system has been applied in research designed to test the comparative usefulness of various pharmacologic agents currently recommended for the neonatal abstinence syndrome and has been found useful in following the progression and diminution of withdrawal symptomatology before, during, and after therapy. Furthermore, the scoring system provides a basis for developing uniform criteria for the assessment and treatment of the neonate born to the addicted mother.

The Finnegan test is typically given to a neonate withdrawing from drugs about every four hours and uses a numbered scale to guide doctors and nurses towards the best course of treatment for the oxytocin compositions and methods provided herein. The individual NAS symptoms are weighted (numerically scoring 1-5) depending on the symptom, and the severity of the symptom. Infants scoring 8 or higher are typically recommended to receive the compositions and methods containing oxytocin provided herein. The scale helps doctors regulate how much treatment a specific neonate needs at any given time. It is to be appreciated, however, the compositions and methods detailed herein may be administered and/or employed at any value on the Finnegan scale where the physician believes therapeutic intervention is needed. It is to be appreciated that the Finnegan scale was first introduced in the 1970s. Thus, it is to be expected modifications, updates and/or changes may be made periodically to the scale. The current invention includes, and is understood to include, all forms, representations and/or iterations of the Finnegan scale currently and/or any future updates or modifications.

The term "AUC" (i.e., "area under the curve," "area under the concentration curve," or "area under the concentration-time curve") is a pharmacokinetic term used to refer a method of measurement of bioavailability or extent of absorption of a drug based on a plot of an individual or pool of individual's blood plasma concentrations sampled at frequent intervals; the AUC is directly proportional to the total amount of unaltered drug in the subjects blood plasma. For example, a linear curve for a plot of the AUC versus dose (i.e., straight ascending line) indicates that the drug is being released slowly into the blood stream and is providing a steady amount of drug to the patient; if the AUC versus dose is a linear relationship this generally represents optimal delivery of the drug into the patient's blood stream. By contrast, a non-linear (i.e. less than dose proportional) AUC versus dose curve indicates rapid release of drug such that some of the drug is not absorbed, or the drug is metabolized before entering the blood stream.

The term "Cmax" (i.e., "maximum concentration") is a pharmacokinetic term used to indicate the peak concentration of a particular drug in the blood plasma of a patient.

The term "Tmax" (i.e., "time of maximum concentration" or "time of Cmax") is a pharmacokinetic term used to indicate the time at which the Cmax is observed during the time course of a drug administration. As would be expected, a dosage form that would include an immediate release as well as a gastric retentive component would have a shorter Tmax and higher Cmax for an immediate release dosage form, but longer Tmax and lower Cmax for a purely gastric retentive dosage form.

"Preventing" in reference to a disorder or unwanted physiological event in a subject, refers specifically to inhibiting or significantly reducing the occurrence of symptoms associated with the disorder and/or the underlying cause of the symptoms.

It should be noted that, as used herein, the singular form "a," "an," and "the" includes plural references unless indicated otherwise. Additionally, as used herein, the term "comprising," and its cognates, are used in their inclusive sense; that is, equivalent to the term "including" and its corresponding cognates.

Neonatal Abstinence Syndrome

NAS has been described as a complex disorder that primarily involves the Central and autonomic nervous systems and the gastrointestinal system. The clinical manifestations of the syndrome vary, ranging from mild tremors and irritability to fever, excessive weight loss, and seizures. Clinical signs typically develop within the first few days after birth, although the timing of their onset, as well as their severity may vary. This variation is poorly understood and is believed to be multifactorial. In particular, the type of drug and the dose and timing of exposure may alter the risk of withdrawal (Hudak et al., *Pediatrics*, 129:e540-e560 (2012)).

Clinical manifestations may develop later in infants who have been exposed to opioids with a longer half-life (e.g., methadone and buprenorphine) than in infants exposed to short-acting opioids. Exposure to additional substances, such as selective serotonin-reuptake inhibitors (SSRIs), benzodiazepines (eg. valium), anticonvulsants (eg. gabapentin) psychostimulants and nicotine, may also alter the onset of the syndrome, as well as the severity of symptoms. Furthermore, other variables may influence the development of NAS, including maternal factors (poor nutrition or stress), placental opioid metabolism, genetic variables, neonatal conditions (prematurity or infection), and environmental factors such as the early care that neonates receive. With these considerations in mind, a typical hospital stay of about 24 to about 48 hours for term neonates known to not be biologically exposed to a drug agent, needs to be extended for neonates known, suspected of having biological exposure to at least one drug agent either prenatally or postnatally. For example, The American Academy of Pediatrics has recommended that opioid-exposed neonates be observed for at least about 3 to about 7 days before discharge if no symptoms appear. However, if the mother is known to have an addiction, suspected of having an addiction, diagnosed as having an addiction or has admitted to having an addiction to one or more drug agents, care providers may begin treatment, as described herein, immediately upon birth.

It is estimated that the percentage of the population that has abused amphetamine type stimulants, for example, amphetamine, methamphetamine, MDMA and cocaine combined is between 1% to 5%. Stimulants, such as cocaine, bind to monoaminergic, preferably dopaminergic transporters and prevent the uptake of extracellular monoamines into the presynaptic cell, resulting in excess neurotransmitter in the synaptic cleft and excess stimulation of dopamine receptors. The dopamine system develops early in gestation in all vertebrate species and is therefore sensitive to exogenous manipulation early in gestation. In fact, some early reports suggested a very severe phenotype in children exposed to cocaine in utero (Thompson et al., *Nat Rev Neurosci.*, 10(4):303-312 (2009)). Children were reported to be emotionally disrupted, cognitively impaired, less likely to socially interact and more likely to die from sudden infant death syndrome ("SIDS").

In general, benzodiazepines and/or barbiturates are indicated, for example, for treatment of generalized anxiety disorder, treatment of panic disorder (with or without agoraphobia), sedation, light anesthesia and anterograde amnesia of perioperative events, control of seizures, and skeletal muscle relaxation. Benzodiazepines are used commonly, even in the absence of complete knowledge of their potential adverse effects. Benzodiazepine compounds fall into three major categories:long-acting compounds—diazepam, chlordiazepoxide, chlorazepate, flurazepam, halazepam, and prazepam; intermediate-acting compounds—clonazepam, lorazepam, quazepam, and estazolam; and short-acting compounds—alprazolam, oxazepam, temazepam, midazolam, and triazolam. The most commonly used benzodiazepines in the United States are diazepam, chlordiazepoxide, clonazepam, lorazepam and alprazolam. For nearly all the current benzodiazepines, the physiological action of the drug has not been fully described. The effects of these drugs appear to be mediated through the inhibitory neurotransmitter gamma-aminobutyric acid ("GABA"). The drugs appear to act on the limbic, thalamic, and hypothalamic levels of the central nervous system to produce sedative and hypnotic effects, reduction of anxiety, anticonvulsant effects, and skeletal muscle relaxation. Specific binding sites with high affinity for benzodiazepines have been detected in the central nervous system, and both GABA and chloride enhance the affinities of these sites for the drugs.

Benzodiazepines and barbiturates are known to cause withdrawal symptoms in neonates that can begin shortly after birth and last for potentially months after birth. Diazepam for example has been shown to cause symptoms that include hypotonia, poor suck, hypothermia, apnea, hypertonia, hyperreflexia, tremors, vomiting, hyperactivity and tachypnea (American Academy of Pediatrics, Committee on Drugs, Pediatrics 101;1079 (1998)).

Many examples have been reported of the specific heath issues and problems associated with neonates having been exposed to a variety of drugs, such as SSRIs and SNRIs, during pregnancy. For example, neonates exposed to the drug citalopram have developed complications requiring prolonged hospitalization, respiratory support and tube feeding and these complications may be observed immediately upon delivery (Celexa® (citalopram hydrobromide) Tablets/Oral Solution). Additionally, reported clinical findings have included respiratory distress, cyanosis, apnea, seizures, temperature instability, feeding difficulty, vomiting, hypoglycemia, hypotonia, hypertonia, hyperreflexia, tremor, jitteriness, irritability, and constant crying. These features are consistent with a direct toxic effect of SSRIs and SNRIs. Moreover, in animal reproduction studies, citalopram has been shown to have adverse effects on embryo/fetal and postnatal development, including teratogenic effects. In rat embryo/fetal development studies, oral administration of citalopram (dosing of 32, 56, or 112 mg/kg/day) to pregnant animals during the period of organogenesis resulted in decreased embryo/fetal growth and survival and an increased incidence of fetal abnormalities. These abnormalities include, for example, cardiovascular and skeletal defects and decreased body weight gain.

It has also been reported that infants exposed to SSRIs in late pregnancy may have an increased risk for persistent pulmonary hypertension of the newborn ("PPHN"). PPHN is associated with a substantial neonatal morbidity and mortality. In a retrospective, case-control study of 377 women whose infants were born with PPHN and 836 women whose infants were born healthy, the risk for developing PPHN was approximately six-fold higher for infants exposed to SSRIs after the 20th week of gestation compared to infants who had not been exposed to antidepressants during pregnancy.

Fluoxetine represents yet another example of specific heath issues and problems reported for neonates having been exposed to this drug during pregnancy. For example, in a study conducted by the European Network of Teratology Information Services, an increased risk of cardiovascular malformations in infants born to women exposed to fluoxetine during the first trimester of pregnancy was observed. Additionally, neonates exposed to fluoxetine late in the third trimester of pregnancy have developed complications, much like those reported for other SSRIs and SNRIs, such as requiring prolonged hospitalization, respiratory support and tube feeding. The reported clinical findings are essentially identical to those described above for citalopram.

It is understood that infants diagnosed with, suspected of having and/or determined or diagnosed to be suffering from NAS are at increased risk for admission to the NICU, birth complications, the need for pharmacologic treatment, and a prolonged hospital stay, outcomes that separate the mother and her infant at a critical time for infant development and bonding. The average length of health facility stay for infants with NAS may vary, but can be about 1 day, about 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days or about 30 days or more for those requiring treatment. Prolonged hospitalization results in the use of a greater portion of health care resources for the care of infants with the neonatal abstinence syndrome than for those without the syndrome. Primary concerns regarding management of NAS include, but are not limited to, the promotion of normal growth and development and to avert or minimize negative outcomes, including discomfort and seizures in the infant and impaired maternal bonding.

It is also understood that a medical treatment for infants, such as neonates, is not a "miniaturized" treatment employed for adults. In addition to the obvious size differences that exist between infants and adults, there are a number of other issues, for example, a much greater vulnerability to infections and diseases, which come into play. As infants are still physically and mentally developing, special attention needs to be present when caring for infants for a variety of unique infant related aspects such as growth, development, symptoms of disease and/or infection and addiction, which uniquely differ when present in adult subjects. These considerations significantly impact the course and type of care prescribed by pediatric health specialists when compared to treatment options for adults.

Most drugs given to neonates have not been sufficiently studied in this population and are often dosed based on information extrapolated from adults or older children. Disease, critical illness, specialized therapies, and developmental changes in the expression of organ-specific drug transporters may further contribute to these differences. Differences in neonatal physiology can also affect pharmacodynamics, resulting in differences in the expected potency, efficacy, or toxicity of drugs. In fact, up to 90% of the medications administered to neonates are either unauthorized, unapproved, or administered off-label (Tayman et al., J Pediatr. Pharmacol. Ther. 16:170-184 (2011)).

Neonates have significant differences in physiology affecting drug absorption, distribution, metabolism, and elimination that makes extrapolating dosages from adults and older children inappropriate. The neonatal period is a time of incredible physiological change leading to unpredictable responses to doses of drugs deemed safe and efficacious in adults. When at comparable drug exposures, neonates can respond differently than older populations due to immaturity of drug targets and receptors. For example, neonates may be more sensitive to morphine than adults due to increased expression of the mu opioid receptor. Opioids lead to an increased incidence of apnea and hypotension in neonates as compared with adults, owing to the early development of receptors primarily in respiratory/cardiovascular areas of the brain (LC Ku & PB Smith, Pediatr. Res. 77:2-9 (2015)).

Additionally, GABA is the principal neurotransmitter of inhibition in the adult mammalian brain. However, at early stages of development, including the embryonic period and first week of postnatal life, GABA plays the role of main neurotransmitter of excitation. The paradoxical excitatory effect of GABA is caused by an inverted chloride gradient and, therefore, a depolarizing direction of GABA type A (GABAA) receptor mediated responses. In addition, another type of GABAergic inhibition mediated by postsynaptic GABA type B (GABAB) receptors is not functional at early stage of life. This change in GABA function results in part from intracellular chloride accumulation which has profound implications for antiepileptics that act by enhancing GABAergic signaling, including phenobarbital and benzodiazepines, as these antiepileptics could potentially worsen seizures in neonates (X Leinekugel et al., 79:189-201 (1999)).

It has been noted that some drugs, such as phenobarbital and phenytoin, cross the neonatal rat and rabbit blood-brain barrier (BBB) to a greater extent than in adults, possibly resulting from greater permeability of the BBB itself or the decreased blood flow to the brain in neonates. It has been determined that the decreased cerebral blood flow gives rise to increased levels of these antiepileptics in the brain, as the increased time spent at the BBB is sufficient to allow more drug—protein dissociation. Furthermore, neonates display an increased sensitivity to the morphine, potentially due to increased BBB permeability. It has also been proposed that another reason for higher brain/plasma ratios of certain drugs in neonates is immature clearance pathways; with increasing age, there is an increase in CSF secretion levels and an opening in ventricular spaces which increases drainage out of the brain (M. D Donovan et al., *Br J Clin Pharmacol*, 81: 62-77 (2016)).

Moreover, it is to be appreciated by one of skill in the art that administration of the compositions and employment of the methods provided herein are amenable to a plurality of medically situational variables. For example, wherein a neonate and/or infant is identified post-birth that requires a surgical procedure, utilization of one of more drug agents may be necessary for performing the surgical procedure, which has the potential to place the neonate and/or infant at risk to experience one or more NAS and/or withdrawal symptoms. This surgical procedure may occur at any time post-birth and at any time during infancy, which includes, for example, up to a year or more post-birth.

Oxytocin

Oxytocin is a naturally occurring nine-amino acid neuropeptide that is primarily produced in the paraventricular and supraoptic nuclei of the mammalian hypothalamus. It is released in to the central nervous system via distributed neural pathways and in to peripheral circulation via the posterior pituitary. The intramuscular injection or intravenous infusion of synthetic oxytocin (Pitocin®) is currently approved in the U.S. to produce or improve uterine contractions to facilitate vaginal delivery and to control postpartum hemorrhage. Intranasal oxytocin (Syntocinon®) had been approved in the U.S. for stimulating milk letdown to facilitate breast-feeding from 1960 until 1997. While the nasal spray of Syntocinon was withdrawn from the U.S. market at the request of the manufacturer, intranasal oxytocin is still marketed outside of the United States in countries such as Switzerland, Portugal, or Brazil.

Oxytocin was one of the first peptide hormones to be isolated and sequenced. Natural oxytocin is a nine amino acid cyclic peptide hormone with two cysteine residues that form a disulfide bridge between positions 1 and 6. The amino acid sequence for human oxytocin is Cys-Tyr-Ile-Gln-Asn-Cys-Pro-Leu-Gly (SEQ ID NO:1).

Oxytocin shares structural similarities with the nine-amino acid neuropeptide vasopressin. Vasopressin is also produced in the supraoptic and paraventricular nuclei of the hypothalamus and is similarly stored in the posterior pituitary. Both of these neuro-hypo-physical hormones are nonapeptides with a disulfide bridge between Cys residues 1 and 6. This results in a peptide constituted of a six-amino acid cyclic part and a COOH-terminal α-amidated three-residue tail. Based on the amino acid at position 8, these peptides are classified into vasopressin and OT families: the vasopressin family contains a basic amino acid (Lys, Arg), and the OT family contains a neutral amino acid at this position. Isoleucine in position 3 is essential for stimulating OT receptors and Arg or Lys in position 8 for acting on vasopressin receptors. The difference in the polarity of these amino acid residues is believed to enable the vasopressin and OT peptides to interact with their respective receptors. However, based on the structural similarities between the two peptides and their respective receptor subtypes, there is considerable binding affinity of both peptide to each of the four known receptor subtypes (OTR, V1aR, V1bR, and V2) and this cross-reactivity is known to account for a significant portion of the physiological and behavioral actions of the two peptides (Gimpl et al., *Physiological Reviews,* 81(2): 630-668 (2001)).

There are processes described for the production of oxytocin, see for example U.S. Pat. Nos. 2,938,891 and 3,076,797; in addition, oxytocin is commercially available. A variety of analogues and derivatives, such as carbetocin or an oxytocin receptor agonist, are available and others can be contemplated for use within the invention and can be produced and tested for biological activity according to known methods. Oxytocin analogues may include, but are not limited to, 4-threonine-1-hydroxy-deaminooxytocin, 4-serine-8-isoleucine-oxytocin, 9-deamidooxytocin, 7-D-proline-oxytocin and its deamino analogue, (2,4-diisoleucine)-oxytocin, deamino oxytocin analogue, 1-deamino-1-monocarba-E12-Tyr(OMe)]-OT(dCOMOT), 4-threonine-7-glycine-oxytocin (TG-OT), oxypressin, deamino-6-carba-oxytoxin (dC60), L-371,257 and the related series of compounds containing an ortho-trigluoro-ethoxyphenylacetyl core such as L-374,943. Other exemplary oxytocin analogues include 4-threonine-1-hydroxy-deaminooxytocin, 9-deamidooxytocin, an analogue of oxytocin containing a glycine residue in place of the glycinamide residue, 7-D-proline-oxytocin (2,4-diisoleucine)-oxytocin, an analogue of oxytocin with natriuretic and diuretic activities, deamino oxytocin analogue; a long-acting oxytocin analogue, 1-deamino-1-monocarba-E12-Tyr(OMe)[-OT(dCOMOT), carbetocin, (1-butanoic acid-2-(O-methyl-L-tyrosine)-1-carbaoxytocin, deamino-1 monocarba-(2-O-methyltyrosine)-oxytocin[d(COMOT)]), [Thr4-Gly7]-oxytocin (TG-OT), oxypressin, Ile-conopres sin, deamino-6-carba-oxytoxin (dC60), d[Lys(8)(5/6C-Fluorescein)]VT, d[Thr(4), Lys(8)(5/6C-Fluorescein)]VT, [HO(1)][Lys(8)(5/6C-Fluorescein)VT, [HO(1)][Thr(4), Lys(8)(5/6CFluorescein)]VT, d[Om(8)(5/6C-Fluorescein)]VT, d[Thr(4), Om(8)(5/6C-Fluorescein)]VT, [HO(1)][Om(8)(5/6C-Fluorescein)]VT, [HO(1)][Thr(4), Om(8)(5/6C-Fluorescein)]VT, and 1-deamino-oxytocin in which the disulfide bridge between residues 1 or 6 is replaced by a thioether, and desamino-oxytocin analogues in which the disulfide bond is replaced by a diselenide bond, a ditelluride bond, a telluroseleno bond, a tellurosulfide bond or a selenosulfide bond (e.g., the peptide analogues of oxytocin described in PCT patent application WO 2011/120,071, incorporated herein by reference). Oxytocin peptides for use within the invention can be peptides that are obtainable by partial substitution, addition, or deletion of amino acids within a naturally occurring or native peptide sequence. Peptides can be chemically modified, for example, by amidation of the carboxyl terminus (—NH$_2$), the use of D amino acids in the peptide, incorporation of small non-peptidyl moieties, as well as the modification of the amino acids themselves (e.g. alkylation or esterification of side chain R-groups). Such analogues, derivatives and fragments should substantially retain the desired biological activity of the native oxytocin peptide. In some embodiments, the oxytocin analogue is 4-serine-8-isoleucine-oxytocin or 9-deamidooxytocin. In some embodiments, the oxytocin analogue is carbetocin. The present disclosure also embraces other known oxytocin analogs, for example, the peptidic oxytocin receptor agonists described in PCT patent application WO 2012/042371 and Wiśniewski et al., *J Med Chem.*, 57:5306-5317 (2014), the entire content of which is incorporated herein by reference. In some embodiments, the oxytocin analogue is a compound selected from Compound Nos. 1-65 described in Tables 1-3 in Wiśniewski et al. *Ibid.* In some embodiments, the oxytocin analogue is a selected from the group consisting of Compound No. 31, Compound No. 47, Compound No. 55 and Compound No. 57.

In some embodiments, oxytocin or an oxytocin analogue is isotopically labeled by having one or more atoms replaced by an isotope having a different atomic mass. Examples of isotopes that may be incorporated into the disclosed compounds include isotopes of hydrogen. The isotopically labeled compound may be administered to a subject of the invention and subsequently detected, yielding useful diagnostic and/or therapeutic management data, according to conventional techniques. Additionally, the isotopically labeled compound may be administered to a subject in need thereof, yielding therapeutically advantageous absorption, distribution, metabolism and/or elimination profiles. All isotopic variations of the oxytocin peptide, e.g. human oxytocin or an analogue or derivative thereof, whether radioactive or not, are contemplated in the instant invention.

In some embodiments, the oxytocin formulation or composition may further comprise one or more mucosal delivery-enhancing agents selected from (A)-(K):(A) solubilization agents; (B) charge modifying agents; (C) pH control agents; (D) degradative enzyme inhibitors; (E) mucolytic or mucus clearing agents; (F) ciliostatic agents; (G) membrane penetration-enhancing agents; (H) modulatory agents of epithelial junction physiology, such as nitric oxide (NO) stimulators, chitosan, and chitosan derivatives; (I) vasodilator agents; (J) selective transport-enhancing agents; and (K) stabilizing delivery vehicles, carriers, supports or complex-forming species with which oxytocin is effectively combined, associated, contained, encapsulated or bound to stabilize the active agent for enhanced mucosal delivery. Membrane penetration-enhancing agents in Group (G) may be (i) a surfactant, (ii) a bile salt, (iii) a phospholipid or fatty acid additive, mixed micelle, liposome, or carrier, (iv) an alcohol, (v) an enamine, (iv) an NO donor compound, (vii) a long-chain amphipathic molecule, (viii) a small hydrophobic penetration enhancer; (ix) sodium or a salicylic acid derivative; (x) a glycerol ester of acetoacetic acid, (xi) a cyclodextrin or beta-cyclodextrin derivative, (xii) a medium-chain fatty acid, (xiii) a chelating agent, (xiv) an amino acid or salt thereof, (xv) an N-acetylamino acid or salt thereof, (xvi) an enzyme degradative to a selected membrane component, (xvii) an inhibitor of fatty acid synthesis, (xviii) an inhibitor of cholesterol synthesis; or (xiv) any combination of the membrane penetration enhancing agents of (i)-(xviii).

In various embodiments of the invention, oxytocin may be combined with one, two, three, four or more of the mucosal delivery-enhancing agents recited in (A)-(K). These mucosal delivery-enhancing agents may be admixed, alone or together, with the oxytocin peptide, or otherwise combined therewith in a pharmaceutically acceptable formulation or delivery vehicle. The oxytocin formulation or composition described herein may provide increased bioavailability of the oxytocin following delivery thereof to a mucosal surface (e.g., in the nasal cavities) of a mammalian subject.

The lists of carriers and additives discussed herein are by no means complete and a worker skilled in the art can choose carriers and excipients from the GRAS (generally regarded as safe) list of chemicals allowed in pharmaceutical preparations and those that are currently allowed by the U.S. Food and Drug Administration in topical and parenteral formulations, and those that become allowed in the future. (See, Wang et al., *J. Parent. Drug Assn.*, 34:452-462 (1980)).

In some embodiments, the oxytocin formulation or composition of the invention may further contain one or more solvent or excipient selected from the group consisting of chlorobutanol, benzalkonium, methyl 4-hydroxybenzoate, propyl 4-hydroxybenzoate, acetic acid, citric acid, glycerol, sodium chloride, sodium monohydrogen phosphate, sorbitol and water.

In some embodiments, the oxytocin formulation or composition, further contains a chitosan-containing excipient. In some embodiments, a chitosan glutamate salt may be preferred for nasal delivery for its superior absorption enhancing ability. In some embodiments, chitosan co-polymer nanoparticles may be used, such as nanoparticles containing chitosan glutamate and a negatively charged polymer (e.g., tripolyphosphate pentasodium). Thiolated chitosans (e.g. chitosan covalently modified with 2-iminothiolane), which have been used in microparticles containing insulin and reduced glutathione, may also be useful as an excipient in the oxytocin formulation or composition described herein.

In some embodiments, the oxytocin formulation or composition, may further contain one or more gelling agents, such that the oxytocin composition forms a gel in the nasal cavity, thus enhancing nasal absorption of oxytocin. Gelling systems useful in the compositions and methods described herein may include any known gelling system, such as a chemically reactive pectin-based gelling system (e.g., PecSys™, Archimedes Pharma) and a thermoreactive polymer gelling system (e.g., Pluronic®, F127, BASF). PecSys.™ is a low viscosity aqueous pectin-based solution, delivered as a fine mist in which each droplet gels on contact with calcium ions in the nasal mucosa. Other low methoxy pectin could also be employed. The gelling temperatures vary depending on the ratios of components and the amount of co-polymer employed in the final formulation. Gelling in the adult human nasal cavity has been demonstrated for Pluronic®. F127 at approximately 18-20% wt/vol, for examples, as used in a vitamin B12 gel supplement (EnerB, Nature's Bounty, NY) and in a gelling sumatriptan, which contains 18% wt/vol Pluronic® F127 and 0.3% wt/vol Carbopol (anionic bioadhesive polymer C934P). The monomer ratios and concentrations may be adjusted for the intended oxytocin formulations to ensure gelling at 25-37° C., around the typical temperature of 34° in the nasal cavity. If the gelation temperature is lower than 25° C., the formulation could gel at room temperature; if the gelation temperature is above 37° C. the formulation would not fully gel on contact with the nasal mucosa. In some embodiments, the oxytocin formulation or composition may further utilize a mucoadhesive agent such as Carbopol. Addition of a mucoadhesive, e.g., addition of up to 0.5% Carbopol, may further lower the gelation temperature.

In some embodiments, the oxytocin formulation or composition, may further contain a surface-active agent, such as a nonionic surfactant (e.g., polysorbate-80), and one or more buffers, stabilizers, or tonicifiers. In some embodiments, the oxytocin formulation or composition further includes a propellant. The pH of the nasal spray solution is optionally between about pH 3.0 and 8.5, but when desired the pH is adjusted to optimize delivery of a charged macromolecular species in a substantially unionized state. The pharmaceutical solvents employed can also be a slightly acidic aqueous buffer (pH 3-7). Suitable buffers for use within these compositions are as described above or as otherwise known in the art. Other components may be added to enhance or maintain chemical stability, including preservatives, surfactants, dispersants or gases. Suitable preservatives include, but are not limited to, phenol, methyl paraben, paraben, m-cresol, thiomersal, benzalkonium chloride, and the like. Suitable surfactants include, but are not limited to, oleic acid, sorbitan trioleate, polysorbates, lecithin, phosphotidyl cholines, and various long chain diglycerides and phospholipids. Suitable dispersants include, but are not limited to, ethylenediaminetetraacetic acid (EDTA), and the like. Suitable gases include, but are not limited to, nitrogen, helium, chlorofluorocarbons (CFCs), hydrofluorocarbons (HFCs), carbon dioxide, air, and the like. Suitable stabilizers and tonicifying agents include sugars and other polyols, amino acids, and organic and inorganic salts.

To further enhance the mucosal delivery of the oxytocin formulation or composition, an enzyme inhibitor, particularly proteases inhibitors, can be included in the composition. Protease inhibitors may include, but are not limited to, antipain, arphamenine A and B, benzamidine HCl, AEBSF, CA-074, calpain inhibitor I and II, calpeptin, pepstatin A, actinonin, amastatin, bestatin, boroleucine, captopril, chloroacetyl-HOLeu-Ala-Gly-$NH_2$, DAPT, diprotin A and B, ebelactone A and B, foroxymithine, leupeptin, phosphoramidon, aprotinin, puromycin, BBI, soybean trypsin inhibitor, phenylmethylsulfonyl fluoride, E-64, chymostatin, 1,10-phenanthroline, EDTA and EGTA. Other enzyme inhibitors such as bacitracin may also be included in the formulation.

To enhance delivery into or across a mucosal surface and/or absorption of the oxytocin formulation or composition, an absorption-enhancing agent can be included in the formulation. These enhancing agents may enhance the release or solubility (e.g., from a formulation delivery vehicle), diffusion rate, penetration capacity and timing, uptake, residence time, stability, effective half-life, peak or sustained concentration levels, clearance and other desired mucosal delivery characteristics (e.g., as measured at the site of delivery) of the composition. Enhancement of mucosal delivery can thus occur by any of a variety of mechanisms, for example by increasing the diffusion, transport, persistence or stability of the oxytocin composition, increasing membrane fluidity, modulating the availability or action of calcium and other ions that regulate intracellular or paracellular permeation, solubilizing mucosal membrane components (e.g., lipids), changing non-protein and protein sulfhydryl levels in mucosal tissues, increasing water flux across the mucosal surface, modulating epithelial junctional physiology, reducing the viscosity of mucus overlying the mucosal epithelium, reducing mucociliary clearance rates, and other mechanisms.

Mucosal absorption enhancing compounds may include, but are not limited to, surfactants, bile salts, dihydrofusidates, bioadhesive/mucoadhesive agents, phospholipid additives, mixed micelles, liposomes, or carriers, alcohols, enamines, cationic polymers, NO donor compounds, long-chain amphipathic molecules, small hydrophobic penetration enhancers; sodium or a salicylic acid derivatives, glycerol esters of acetoacetic acid, cyclodextrin or beta-cyclodextrin derivatives, medium-chain fatty acids, chelating agents, amino acids or salts thereof, N-acetylamino acids or salts thereof, mucolytic agents, enzymes specifically targeted to a selected membrane component, inhibitors of fatty acid synthesis and inhibitors of cholesterol synthesis.

The oxytocin molecule described and/or contemplated herein can be prepared by chemical synthesis using either automated or manual solid phase synthetic technologies, generally known in the art. The oxytocin molecules can also be prepared using molecular recombinant techniques known in the art.

Where a range of oxytocin values is provided, it is intended that each intervening value between the upper and lower limit of that range and any other stated or intervening value in that stated range is encompassed within the disclosure. For example, if a range of 0.01 μg to 10 μg is stated, it is intended that 0.02 μg, 0.03 μg, 0.04 μg, 0.05 μg, 0.06 μg. 0.07 μg, 0.08 μg, 0.09 μg, 0.1 μg, 0.2 μg, 0.3 μg, 0.4 μg, 0.5 μg, 0.6 μg. 0.7 μg, 0.8 μg, 0.9 μg, 1.0 μg, 2.0 μg, 3.0 μg, 4.0 μg, 5.0 μg, 6.0 μg. 7.0 μg, 8.0 μg, and 9.0 μg are also explicitly disclosed, as well as the range of values greater than or equal to 10 μg and the range of values less than or equal 0.01 μg. If a range of 1-20% is stated, it is intended that 2%, 3%, 4%, 5%, 6%, 7%, 8%, 9%, 10%, 11%, 12%, 13%, 14%, 15%, 16%, 17%, 18%, 19% are also explicitly disclosed. Furthermore, each smaller range in a stated range between any stated value or intervening value and any other stated or intervening value in that stated range is encompassed within the disclosure. The upper and lower limits of these smaller ranges may independently be included or excluded in the range, and each range where either, neither, or both limits are included in the smaller ranges is also encompassed within the disclosure, subject to any specifically excluded limit in the stated range. Where the stated range includes one or both of the limits, ranges excluding either or both of those included limits are also included in the disclosure.

In some embodiments, the effective dose of oxytocin is about 0.01 μg to about 10 mg. In some embodiments, the effective dose of oxytocin is about 0.01 μg to about 5 mg, 0.01 μg to about 4 mg, about 0.01 μg to about 3 mg, about 0.01 μg to about 2 mg, or about 0.01 μg to about 1 mg. In some embodiments, the effective dose of oxytocin is about 0.05 μg to about 5 mg, 0.05 μg to about 4 mg, about 0.05 μg to about 3 mg, about 0.05 μg to about 2 mg, or about 0.05 μg to about 1 mg. In other embodiments, the effective dose of oxytocin is about 0.1 μg to about 5 mg, about 0.1 μg to about 4 mg, about 0.1 μg to about 3 mg, about 0.1 μg to about 2 mg, or about 0.1 μg to about 1 mg. In other embodiments, the effective dose of oxytocin is about 0.2 μg to about 5 mg, about 0.2 μg to about 4 mg, about 0.2 μg to about 3 mg, about 0.2 μg to about 2 mg, or about 0.2 μg to about 1 mg.

In other embodiments, the effective dose of oxytocin is about 0.3 μg to about 5 mg, about 0.3 μg to about 4 mg, about 0.3 μg to about 3 mg, about 0.3 μg to about 2 mg, or about 0.3 μg to about 1 mg. In other embodiments, the effective dose of oxytocin is about 0.4 μg to about 5 mg, about 0.4 µg to about 4 mg, about 0.4 µg to about 3 mg, about 0.4 µg to about 2 mg, or about 0.4 µg to about 1 mg. In other embodiments, the effective dose of oxytocin is about 0.5 µg to about 5 mg, about 0.5 µg to about 4 mg, about 0.5 µg to about 3 mg, about 0.5 µg to about 2 mg, or about 0.5 µg to about 1 mg. In other embodiments, the effective dose of oxytocin is about 0.6 µg to about 5 mg, about 0.6 µg to about 4 mg, about 0.6 µg to about 3 mg, about 0.6 µg to about 2 mg, or about 0.6 µg to about 1 mg. In other embodiments, the effective dose of oxytocin is about 0.7 µg to about 5 mg, about 0.7 µg to about 4 mg, about 0.7 µg to about 3 mg, about 0.7 µg to about 2 mg, or about 0.7 µg to about 1 mg. In some embodiments, the effective dose of oxytocin is about 0.8 µg to about 5 mg, about 0.8 µg to about 4 mg, about 0.8 µg to about 3 mg, about 0.8 µg to about 2 mg, or about 0.8 µg to about 1 mg.

In some embodiments, the effective dose of oxytocin is about 0.9 µg to about 5 mg, about 0.9 µg to about 4 mg, about 0.9 µg to about 3 mg, about 0.9 µg to about 2 mg, or about 0.9 µg to about 1 mg. In some embodiments, the effective dose of oxytocin is about 0.01 µg to about 1000 µg, about 0.01 µg to about 800 µg, about 0.01 µg to about 600 µg, about 0.01 µg to about 400 µg, about 0.01 µg to about 200 µg, or about 0.01 µg to about 100 µg. In some embodiments, the effective dose of oxytocin is about 0.02 µg to about 1000 µg, about 0.02 µg to about 800 µg, about 0.02 µg to about 600 µg, about 0.02 µg to about 400 µg, about 0.02 µg to about 200 µg, or about 0.02 µg to about 100 µg. In some embodiments, the effective dose of oxytocin is about 0.03 µg to about 1000 µg, about 0.03 µg to about 800 µg, about 0.03 µg to about 600 µg, about 0.03 µg to about 400 µg, about 0.03 µg to about 200 µg, or about 0.03 µg to about 100 µg. In some embodiments, the effective dose of oxytocin is about 0.04 µg to about 1000 µg, about 0.04 µg to about 800 µg, about 0.04 µg to about 600 µg, about 0.04 µg to about 400 µg, about 0.04 µg to about 200 µg, or about 0.02 µg to about 100 µg. In some embodiments, the effective dose of oxytocin is about 0.05 µg to about 1000 µg, about 0.05 µg to about 800 µg, about 0.05 µg to about 600 µg, about 0.05 µg to about 400 µg, about 0.05 µg to about 200 µg, or about 0.05 µg to about 100 ng.

In some embodiments, the effective dose of oxytocin is about 0.06 µg to about 1000 µg, about 0.06 µg to about 800 µg, about 0.06 µg to about 600 µg, about 0.06 µg to about 400 µg, about 0.06 µg to about 200 µg, or about 0.06 µg to about 100 µg. In some embodiments, the effective dose of oxytocin is about 0.07 µg to about 1000 µg, about 0.07 µg to about 800 µg, about 0.07 µg to about 600 µg, about 0.07 µg to about 400 µg, about 0.07 µg to about 200 µg, or about 0.07 µg to about 100 µg. In some embodiments, the effective dose of oxytocin is about 0.08 µg to about 1000 µg, about 0.08 µg to about 800 µg, about 0.08 µg to about 600 µg, about 0.08 µg to about 400 µg, about 0.08 µg to about 200 µg, or about 0.08 µg to about 100 µg. In some embodiments, the effective dose of oxytocin is about 0.09 µg to about 1000 µg, about 0.09 µg to about 800 µg, about 0.09 µg to about 600 µg, about 0.09 µg to about 400 µg, about 0.09 µg to about 200 µg, or about 0.09 µg to about 100 µg.

In other embodiments, the effective dose of oxytocin is about 0.1 µg to about 1000 µg, about 0.1 µg to about 800 µg, about 0.1 µg to about 600 µg, about 0.1 µg to about 400 µg, about 0.1 µg to about 200 µg, or about 0.1 µg to about 100 µg. In some embodiments, the effective dose of oxytocin is about 0.2 µg to about 1000 µg, about 0.2 µg to about 800 µg, about 0.2 µg to about 600 µg, about 0.2 µg to about 400 µg, about 0.2 µg to about 200 µg, or about 0.2 µg to about 100 µg. In some embodiments, the effective dose of oxytocin is about 0.3 µg to about 1000 µg, about 0.3 µg to about 800 µg, about 0.3 µg to about 600 µg, about 0.3 µg to about 400 µg, about 0.3 µg to about 200 µg, or about 0.3 µg to about 100 µg. In some embodiments, the effective dose of oxytocin is about 0.4 µg to about 1000 µg, about 0.4 µg to about 800 µg, about 0.4 µg to about 600 µg, about 0.4 µg to about 400 µg, about 0.4 µg to about 200 µg, or about 0.4 µg to about 100 µg. In some embodiments, the effective dose of oxytocin is about 0.5 µg to about 1000 µg, about 0.5 µg to about 800 µg, about 0.5 µg to about 600 µg, about 0.5 µg to about 400 µg, about 0.5 µg to about 200 µg, or about 0.5 µg to about 100 µg.

In some embodiments, the effective dose of oxytocin is about 0.6 µg to about 1000 µg, about 0.6 µg to about 800 µg, about 0.6 µg to about 600 µg, about 0.6 µg to about 400 µg, about 0.6 µg to about 200 µg, or about 0.6 µg to about 100 µg. In some embodiments, the effective dose of oxytocin is about 0.7 µg to about 1000 µg, about 0.7 µg to about 800 µg, about 0.7 µg to about 600 µg, about 0.7 µg to about 400 µg, about 0.7 µg to about 200 µg, or about 0.7 µg to about 100 µg. In some embodiments, the effective dose of oxytocin is about 0.8 µg to about 1000 µg, about 0.8 µg to about 800 µg, about 0.8 µg to about 600 µg, about 0.8 µg to about 400 µg, about 0.8 µg to about 200 µg, or about 0.8 µg to about 100 µg. In some embodiments, the effective dose of oxytocin is about 0.9 µg to about 1000 µg, about 0.9 µg to about 800 µg, about 0.9 µg to about 600 µg, about 0.9 µg to about 400 µg, about 0.9 µg to about 200 µg, or about 0.9 µg to about 100 µg.

In other embodiments, the effective dose of oxytocin is about 1 µg to about 1000 µg, about 1 µg to about 800 µg, about 1 µg to about 600 µg, about 1 µg to about 400 µg, about 1 µg to about 200 µg, about 1 µg to about 100 µg, about 1 µg to about 50 µg, about 1 µg to about 40 µg, about 1 µg to about 30 µg, about 1 µg to about 20 µg, about 1 µg to about 10 µg, or about 1 µg to about 5 µg.

In some embodiments, the effective dose of oxytocin is about 0.02 IU to about 1000 IU. In some embodiments, the effective dose of the oxytocin peptide is about 0.04 IU to about 500 IU, about 0.06 IU to about 500 IU, about 0.08 IU to about 500 IU or about 0.1 IU to about 1000 IU. In some embodiments, the effective dose of the oxytocin peptide is about 0.2 IU to about 500 IU, about 0.4 IU to about 500 IU, about 0.4 IU to about 400 IU, about 0.4 IU to about 250 IU, about 0.4 IU to about 200 IU, about 0.4 IU to about 150 IU, about 0.4 IU to about 100 IU, about 0.4 IU to about 50 IU, about 0.4 IU to about 40 IU, about 0.4 IU to about 25 IU, about 0.5 IU to about 500 IU, about 0.5 IU to about 250 IU, about 0.5 IU to about 100 IU, about 0.5 IU to about 50 IU, about 0.8 IU to about 500 IU, about 0.8 IU to about 400 IU, about 0.8 IU to about 250 IU, about 0.8 IU to about 200 IU, about 0.8 IU to about 100 IU, about 0.8 IU to about 80 IU, about 0.8 IU to about 60 IU, about 0.8 IU to about 40 IU, about 1 IU to about 500 IU, about 1 IU to about 400 IU, about 1 IU to about 250 IU, about 1 IU to about 100 IU, about 1 IU to about 80 IU, about 1 IU to about 60 IU, about 1 IU to about 40 IU, about 1 IU to about 20 IU, about 1 IU to about 10 IU, about 2 IU to about 500 IU, about 2 IU to about 250 IU, about 2 IU to about 150 IU, about 2 IU to about 60 IU, about 2 IU to about 45 IU, about 2 IU to about 25 IU, about 4 IU to about 500 IU, about 4 IU to about 250 IU, about 4 IU to about 125 IU, about 4 IU to about 50 IU, or about 4 IU to about 40 IU.

In some embodiments, the effective dose of oxytocin is about 0.02 IU, about 0.04 IU, about 0.06 IU, about 0.08 IU, about 0.1 IU, about 0.2 IU, about 0.3 IU, about 0.4 IU, about 0.6 IU, about 0.8 IU, about 1 IU, about 2 IU, about 3 IU, about 4 IU, about 5 IU, about 6 IU, about 7 IU, about 8 IU, about 9 IU, about 10 IU, about 11 IU, about 12 IU, about 13 IU, about 14 IU, about 15 IU, about 16 IU, about 17 IU, about 18 IU, about 19 IU, about 20 IU, about 21 IU, about 22 IU, about 23 IU, about 24 IU, about 25 IU, about 26 IU, about 27 IU, about 28 IU, about 29 IU, about 30 IU, about 31 IU, about 32 IU, about 33 IU, about 34 IU, about 35 IU, about 36 IU, about 37 IU, about 38 IU, about 39 IU, about 40 IU, about 41 IU, about 42 IU, about 43 IU, about 44 IU, about 45 IU, about 46 IU, about 47 IU, about 48 IU, about 49 IU, or about 50 IU, or about 55 IU, or about 60 IU, or about 65 IU, or about 70 IU, or about 75 IU, or about 80 IU, or about 85 IU, or about 90 IU, or about 95 IU, or about 100 IU.

In some embodiments, oxytocin is present in a composition, formulation, a diluent, or a pharmaceutically acceptable carrier in a concentration of between about 0.01 µg to about 10 mg, preferably about 0.05 µg to about 5 mg, more preferably about 0.1 µg to about 1 mg or most preferably about 0.1 µg to about 500 µg. Thus, in a liquid composition or formulation the oxytocin is present in an amount between about 0.01 µg/0.5 µL to about 10 mg/500 mL, or in an amount between about 0.05 µg/0.25 µL to about 5 mg/250 mL, or in an amount between about 0.1 µg/5 to about 1 µg/50 µL, or in an amount between about 1 µg/50 µL to about 1 mg/25 mL, or in an amount between about 0.5 µg/25 µL to about 0.5 mg/12.5 mL. See, for example, Tauber et al., *Pediatrics,* 139(2) (2017)).

In one embodiment, the oxytocin is human oxytocin having the amino acid sequence Cys-Tyr-Ile-Gln-Asn-Cys-Pro-Leu-Gly (SEQ. ID NO:1). In another embodiment the oxytocin is human oxytocin having the amino acid sequence Cys-Tyr-Ile-Gln-Asn-Cys-Pro-Leu (SEQ. ID NO:2). In yet another embodiment, the oxytocin is human oxytocin having the amino acid sequence Cys-Tyr-Ile-Gln-Asn-Cys-Pro (SEQ. ID NO:3). In still another embodiment, the oxytocin is human oxytocin having the amino acid sequence Cys-Tyr-Ile-Gln-Asn-Cys (SEQ. ID NO:4).

Optionally, the oxytocin formulation or composition may contain magnesium or a magnesium salt or other divalent metals (Liu et al., *J Am. Chem. Soc.*, 127(7) (2005)). Such agents may be obtained from commercial sources or prepared following methods known in the art. For example, magnesium citrate may be prepared following procedures described in Staszczuk P, et al. *Physicochem Probl Mineral Proc* 37: 149-158 (2003), U.S. Pat. Nos. 1,936,364 and 2,260,004).

In some embodiments, the oxytocin formulation or composition contains one or more magnesium salts selected from the group consisting of magnesium citrate, magnesium chloride, magnesium sulfate, magnesium acetate, magnesium lactate, magnesium stearate, magnesium oxide, magnesium carbonate, magnesium glycinate, magnesium maltate, magnesium taurate, magnesium gluconate, magnesium succinate, and magnesium pyrophosphate.

In some embodiments, the oxytocin formulation or composition may further contain one or more pharmaceutically acceptable carriers (thus constituting a pharmaceutical composition) and optionally other ingredients, such as excipients, vehicles, emulsifiers, stabilizers, preservatives, buffers, and/or other additives that may enhance stability, delivery, absorption, half-life, efficacy, pharmacokinetics, and/or pharmacodynamics, reduce adverse side effects, or provide other advantages for pharmaceutical use. Exemplary excipients include solubilizers, surfactants and chelators. For example, formulations may include, methyl-.beta.-cyclodextrin, edetate disodium, arginine, sorbitol, NaCl, methylparaben sodium (MP), propylparaben sodium (PP), chlorobutanol (CB), benzyl alcohol, zinc chloride, ethyl alcohol, didecanoyl L-.alpha.-phosphatidylcholine (DDPC), polysorbate, lactose, citrate, tartrate, acetate, and/or phosphate.

Liquid carriers of the invention include, but are not limited to, water, saline, aqueous dextrose, and glycols particularly (when isotonic) for solutions. The carrier can also be selected from various oils, including those of petroleum, animal, vegetable or synthetic origin (e.g. peanut oil, olive oil, soybean oil, mineral oil, sesame oil, and the like). Suitable pharmaceutical excipients include, but are not limited to, starch, cellulose, talc, glucose, lactose, sucrose, gelatin, malt, rice, flour, chalk, silica gel, magnesium stearate, sodium stearate, glycerol monostearate, sodium chloride, dried skim milk, glycerol, propylene glycol, water, ethanol, and the like. The compositions can be subjected to conventional pharmaceutical processes, such as sterilization, and can contain conventional pharmaceutical additives, such as preservatives, stabilizing agents, reducing agents, antioxidants, chelating agents, wetting agents, emulsifying agents, dispersing agents, jelling agents or salts for adjusting osmotic pressure, buffers, and the like. A liquid carrier may be hypotonic or isotonic with body fluids and may have a pH within the range of between about 3.5 to about 8.5. The use of additives in the preparation of peptide and/or protein-based compositions, particularly pharmaceutical compositions, is well-known in the art. In some embodiments, the composition has a pH of about 2 to about 7. In some embodiments, the composition has a pH of about 4 to about 7. In a preferred embodiment, the pH of the formulation/composition is about 4.5.

Drug Agents

Opioid Drug Agents

Opioid and opiate drug agents are described herein and include, for example: codeine, fentanyl(Actiq, Duragesic, Fentora, Abstral, Onsolis), carfentanil, sufentanil, alfentanil, remifentanil, hydrocodone (Hysingla, Zohydro ER), hydrocodone/acetaminophen (Lorcet, Lortab, Norco, Vicodin), hydromorphone (Dilaudid, Exalgo), Meperidine (Demerol), tramadol, heroin, methadone (Dolophine, Methadose), morphine (Kadian, MS Contin, Morphabond), oxycodone (OxyContin, Oxaydo), oxycodone and acetaminophen (Percocet, Roxicet), oxycodone and naloxone, meloxicam, kratom, Opana and Opana ER.

Anxiolytic Drug Agents

Benzodiazepines: The prevalence of anxiety disorders during pregnancy and the postnatal period has not been studied as extensively. However, based on a systematic review of the literature by Ross and McLean, obsessive-compulsive disorder and generalized anxiety disorder have high perinatal prevalence rates, being up to 4% and 9%, respectively (Ross et al., *J Clin Psychiatry.*, 67:1285-1298 (2006)). Perinatal anxiety disorders are associated with adverse obstetric consequences, such as premature labor and delivery, and adverse developmental outcomes due to fetal exposure to elevated hormone levels, for example, cortisol. Pharmacotherapy for anxiety disorders consists of benzodiazepines and SSRIs.

Benzodiazepines act on the GABA receptor, leading to sedative, anticonvulsant, and hypnotic effects. This class of medication has various subgroups with varying durations of action, such as long-acting (diazepam), which is described in detail below, intermediate-acting (clonazepam, lorazepam), which is described in detail below, and short-acting (alprazolam, midazolam) compounds, further described in detail below (Iqbal et al., *Psychiatr Serv.*, 53:39-49 (2002)).

Intoxication and withdrawal syndromes related to maternal benzodiazepine use have been reported in the literature (Laegreid L., *Acta Obstet Gynecol Scand.*, 71:655-656 (1992)). Laegreid et al. compared the effect of maternal use of benzodiazepines in 17 newborn infants with that in a group of 21 newborns exposed to other psychotropic drugs and 29 control newborns with no known exposures (Laegreid et al., *Neuropediatrics*, 23:18-23 (1992)).

Neurological examinations demonstrated significant differences, from depression to hyperexcitability of the central nervous system. Symptoms such as drowsiness, absent reflexes, and poor sucking were attributed to neonatal intoxication, whereas other symptoms and signs such as regurgitation, jitteriness, tremor, startles, and monotonous cry were linked to neonatal withdrawal. This study provided evidence for the presence of both a neonatal drug effect and a withdrawal syndrome in response to gestational benzodiazepine use. Neonatal withdrawal has been linked to more prolonged gestational use of benzodiazepines and has also been described subsequent to acute maternal use during labor.

An early case report by Rementeria and Bhatt from 1977 described early onset of symptoms within 2-3 hours after birth, consisting of mild tremor in three infants with prolonged intrauterine exposure to diazepam (Rementeria et al., *J Pediatr.*, 90:123-126 (1977)). Later onset of withdrawal was manifested by irritability, hypertonicity, tachypnea, vigorous sucking, hyperactivity, vomiting, loose stools, and poor weight gain. Symptoms increased in severity and lasted for variable lengths of time of up to 1 month in duration.

A randomized controlled trial of the use of lorazepam premedication for management of labor pain demonstrated some differences on the neurobehavioral examination performed at 2-4 hours and again at 24 hours after birth (McAuley et al., *BJOG*, 89:149-154 (1982)). Although no significant differences were found, there was a trend towards poorer results on tests of resistance to passive movement, for example, truncal and general body tone, and more neonatal respiratory depression in infants acutely exposed to lorazepam. Repeat examination at 24 hours showed significant improvement in symptoms such as increased muscle tone and alertness. These findings can be explained by the limited ability of infants to metabolize diazepam, leading to a prolonged presence of the drug in their tissues and, therefore, more prolonged pharmacologic effects, resulting in later onset of withdrawal symptoms/signs at 2-3 weeks of life. Earlier withdrawal symptoms can be attributed to maternal abstinence from benzodiazepine use for a couple of days before delivery.

Thus, there is a spectrum of clinical presentations related to both neonatal intoxication and withdrawal. Neonatal benzodiazepine withdrawal includes hypertonia, hypothermia, hyperbilirubinemia, irritability, abnormal sleep patterns, tremors, suckling difficulties, inconsolable crying, and respiratory depression, with onset immediately after delivery and potentially lasting for up to 3 weeks postnatally (Iqbal M M et al., *Psychiatr Serv.*, 2002; 53:39-49 (2002).

Diazepam: Among anxiolytic agents, it appears only diazepam has been systematically studied among pregnant women (Valium®). Until the early 1980s, diazepam was the most frequently prescribed benzodiazepine in the United States and worldwide (Shader R I et al., *New England Journal of Medicine*, 328:1398-1405 (1993)). Diazepam is indicated for the management of anxiety disorders and for the short-term relief of symptoms of anxiety. Diazepam is also useful in the relief of acute agitation; the relief of tremor; management of withdrawal from benzodiazepines or barbiturates; and treatment of hallucinosis. It is also used as a skeletal muscle relaxant, as preoperative medication, and as an adjunct to anticonvulsants in the treatment of seizures. Diazepam and its major metabolite, N-desmethyldiazepam, which are both pharmacologically active, freely cross the human placenta during early pregnancy as a result of their high lipid solubility. After the sixth month of pregnancy, the loss of the cytotrophoblasts—Langerhan's cells—from the placenta further facilitates the transport of diazepam across the placenta.

Also, diazepam and N-desmethyldiazepam are bound to fetal plasma proteins more extensively than to maternal plasma proteins; maternal protein binding is lower in the pregnant than the nonpregnant state. After either intravenous or intramuscular injection, diazepam was found to cross the placenta rapidly and to reach considerably higher concentrations in cord plasma than in maternal plasma, with a fetal-maternal ratio of 1.2 to 2, during early pregnancy.

Substantial accumulation of diazepam may occur in adipose tissue. High concentrations are also present in the brain, the lungs, and the heart. The lipophilic nature of diazepam, its high intake in animal fat tissue, its easy penetration into brain white matter, and its long retention in neural tissues in monkeys all suggest that human tissue may act as a depot for diazepam. In most cases the neonate is capable of slowly metabolizing small doses of diazepam although diazepam and its active metabolite may persist for at least a week in pharmacologically active concentrations after administration of high dosages to the mother. The mean plasma half-life in the neonate is about 31 hours. There is evidence that diazepam and its metabolite, N-desmethyldiazepam, is excreted in the breast milk of nursing mothers in low concentrations, depending on the dosage (Patrick M J et al., *Lancet* 1:542-543 (1972)).

Chlordiazepoxide:Chlordiazepoxide hydrochloride is a long-acting benzodiazepine indicated for the management of anxiety disorders, withdrawal symptoms from chronic alcoholism, and preoperative apprehension and anxiety. It also has appetite-stimulating and weak analgesic effects. Chlordiazepoxide has a very low toxicity and is safe for preanesthetic use during labor, even in large intravenous dosages. Chlordiazepoxide is readily transmitted across the placenta, and concentrations in fetal blood are similar to those in maternal circulation. There has been one report of congenital malformation associated with the use of chlordiazepoxide during early pregnancy. In an analysis by Milkovich and Van den Berg Milkovich L., et al., *New England Journal of Medicine*, 291:1268-1271 (1974)) of 19,044 live births, severe congenital anomalies—spastic diplegia, microcephaly, duodenal atresia, and mental deficiency—occurred more often among infants of mothers who took chlordiazepoxide during the first 42 days of pregnancy than among infants of mothers who took other drugs or no drugs (11.4 per 100 compared with 4.6 per 100 and 2.6 per 100, respectively). Fetal death rates were also higher in the group exposed to chlordiazepoxide than in the control group. Like many other benzodiazepines, chlordiazepoxide is excreted in human milk.

Clonazepam: Clonazepam is a benzodiazepine anticonvulsant that has been available for clinical use since 1973 (Klonopin®, Rivotril®). Among adults, clonazepam is metabolized primarily by hydroxylation, although this metabolic pathway generally is impaired in the newborn. The half-life in adults is 20 to 60 hours. Although the half-life for clonazepam in neonates is not known, the half-lives of other benzodiazepine derivatives are two to four times longer for neonates than for adults. No adequate studies have determined the risks of the use of clonazepam by pregnant women to the unborn fetus. There have been some clinical reports of congenital anomalies and other adverse effects among the children of epileptic mothers who took clonazepam alone or with other drugs during pregnancy. In Turkey, 12 of 104 children who had been exposed to antiepileptic drugs in utero had various major congenital malformations. As with many other benzodiazepines, clonazepam is excreted in human milk.

Lorazepam: Lorazepam belongs to a group of 1,4-benzodiazepam derivatives that have a higher potency than the drugs that belong to the closely related chlordiazepoxide group of derivatives (Ativan®). Lorazepam is used in comparatively small dosages-1 to 4 mg a day for adults—as a broad-spectrum tranquilizer for the treatment of anxiety and physical tension, for insomnia in association with anxiety, as an effective anticonvulsant, and for premedication before surgical anesthesia. One useful property of lorazepam is its prolonged amnestic action during labor. Its use has been suggested for pregnancy-related hypertension, for which a similar drug—diazepam—has also been used. Lorazepam and its pharmacologically inactive glucuronide metabolite do not cross the placenta as easily as other benzodiazepines, such as diazepam, and do not have the long-lasting effects on the newborn that occur with diazepam and nitrazepam. Several studies have shown that cord plasma concentrations of lorazepam were generally lower than the corresponding maternal concentrations (McBride R J et al., *British Journal of Anaesthesia,* 51:971-978 (1979)). Lorazepam has a half-life of about 12 hours in adults, which is appreciably shorter than that of diazepam. Lorazepam is metabolized predominantly to a pharmacologically inactive glucuronide that does not accumulate in the tissues. Lorazepam's elimination from the newborn is slow—term babies continue to excrete detectable amounts for up to eight days. Elimination of several other benzodiazepines is even slower in premature infants. In addition, lorazepam's short half-life could increase the risk of neonatal withdrawal. Lorazepam is excreted into breast milk in low concentrations (Summerfield R J et al., *British Journal of Anaesthesia,* 57:1042-1043 (1985)).

Alprazolam:Alprazolam, which was introduced in 1980, has replaced diazepam as the most widely prescribed benzodiazepine and is one of the drugs most often prescribed for anxiety to women of reproductive age (Xanax®). It is used in the treatment of generalized anxiety disorder and panic disorder with or without agoraphobia. Alprazolam has a shorter half-life (ten to 24 hours) than other benzodiazepines, which results in less cumulative sedation when multiple daily doses are taken (Garzone P D et al., *Clinical Pharmacokinetics,* 16:337-364 (1989)). Alprazolam, a triazolobenzodiazepine, and its two hydroxylated metabolites are known to cross the placenta. Alprazolam is found in low concentrations in breast milk.

Additional anxiolytic drugs include, but are not limited to, Oxazepam (Serax®, Zaxopam®, Serapax®), clobazam (Onfi®), estazolam (Prosom®), flurazepam (Dalmane®), midazolam (Versed®), temazepam (Restoril®), and triazolam (Halcion®), bromazepam (Lectopam®, Lexotan®), clorazepate (Tranxene®), tofisopam (Emandaxin® and Grandaxin®).

Excretion of benzodiazepines is markedly delayed among premature infants. Signs of withdrawal may be noticed only after fetal exposure to the drug. In general, these symptoms appear within a few days to three weeks after birth and can last up to several months. Physicians should be aware of the potential for a delayed withdrawal syndrome when caring for infants whose mothers received benzodiazepine compounds—especially diazepam, chlordiazepoxide, triazolam, and alprazolam—during pregnancy. Signs of withdrawal may develop even after the infant has been discharged from the newborn nursery.

Meprobamate: Meprobamate is a carbamate with hypnotic, sedative, and some muscle relaxant properties, although in therapeutic doses, reduction of anxiety rather than a direct effect may be responsible for muscle relaxation. Meprobamate is widely known as Miltown® and Equanil®. Meprobamate has been reported to have anticonvulsant actions against petit mal seizures, but not against grand mal seizures (which may be exacerbated). It is used in the treatment of anxiety disorders, and also for the short-term management of insomnia.

Beta-blockers: Beta-blockers, such as propranolol and oxprenolol, are agents that work by temporarily stopping or reducing the body's natural "fight-or-flight" responses. In turn, they reduce stress on certain parts of the body, such as the heart and the blood vessels in the brain. They lower blood pressure, protect against heart attacks, and can improve the outlook for people with heart failure. A beta-blocker is typically prescribed for several different conditions including high blood pressure, angina and some abnormal heart rhythms, heart, anxiety, migraine, glaucoma, and overactive thyroid symptoms. They are also sometimes known as beta antagonists, beta-adrenergic blocking agents, or beta-adrenergic antagonists.

Barbiturates: Barbiturates are central nervous depressants. They reduce the activity of nerves causing muscle relaxation. They can reduce heart rate, breathing and blood pressure. All barbiturates affect GABA, a neurotransmitter (chemical) that nerves use to communicate with one another. Barbiturates include, for example, amobarbital (Amytal®), butobarbital (Butisol®), pentobarbital (Nembutal®), secobarbital (Seconal®), belladonna and phenobarbital (Donnatal®), butalbital/acetaminophen/caffeine (Esgic®, Fioricet®), butalbital/aspirin/caffeine (Fiorinal Ascomp®, Fortabs®). Barbiturates are known to slow breathing, reduce heart rate, and are habit forming.

Antidepressant Drug Agents

The prevalence of depression and anxiety disorders during pregnancy and the postnatal period has not been well characterized. However, based on a systematic review of the literature by Ross and McLean, obsessive-compulsive disorder and generalized anxiety disorder have high perinatal prevalence rates, being up to 4% and 9%, respectively (Ross et al., *J Clin Psychiatry.,* 67:1285-1298 (2006)). Perinatal anxiety disorders are associated with adverse obstetric consequences, such as premature labor and delivery, and adverse developmental outcomes due to fetal exposure to elevated hormone levels, for example, cortisol. Pharmacotherapy for depression and anxiety disorders include, for example, SSRIs, SNRIs and other agents described herein.

Neurological examinations demonstrated significant differences, from depression to hyperexcitability of the central nervous system. Symptoms such as drowsiness, absent reflexes, and poor sucking were attributed to neonatal intoxication, whereas other symptoms and signs such as regurgitation, jitteriness, tremor, startles and monotonous cry were linked to neonatal withdrawal.

SSRIs:SSRIs are among the most commonly prescribed antidepressants. They are highly effective and generally cause fewer side effects when compared to other antidepressants. SSRIs help to alleviate symptoms of depression by blocking the reabsorption or reuptake of serotonin in the brain. Serotonin is a naturally occurring neurotransmitter, i.e., chemical, which is used by brain cells to communicate. As SSRIs mainly affect the levels of serotonin and not levels of other neurotransmitters, they are commonly referred to as "selective." SSRIs include, for example, but are not limited to: citalopram (Cipramil®) (Recital®) (Celexa®), escitalopram (Cipralex®) (Lexapro®), fluoxetine (Prozac®) (Prizma®) (Flutine®) (Profem®), fluvoxamine (Luvox®) (Favoxil®), fluvoxamine CR(Luvox® CR), paroxetine (Paxil®) (Seroxat®) (Paxxet®) (Paroxetine teva) (Parotine®), paroxetine CR(Paxil® CR) and sertraline (Lustral®) (Serenade®) (Sertraline teva) (Zoloft®) and venlafaxine (Efexor®) (Venla®) (Viepax®) (Venlafafaxine teva).

SNRIs: SNRIs work by blocking the reabsorption of the neuro-transmitters serotonin and norepinephrine in the brain. They may also have an effect on other neurotransmitters. SNRIs include, for example, but are not limited to: desvenlafaxine (Pristiq®), duloxetine (Cymbalta®), venlafaxine (Effexor®), venlafaxine XR (Effexor®), milnacipran (Savella®) and levomilnacipran (Fetzima®).

Tricyclic antidepressants ("TCAs"):TCAs were one of the first approved antidepressants. Although they are effective, they have been replaced by newer antidepressants that generally cause fewer side effects. Like SNRIs, TCAs work by blocking the reabsorption of the neuro-transmitters serotonin and norepinephrine in the brain. Additionally, they block muscarinic M1, histamine H1 and alpha-adrenergic receptors. TCAs include, for example, but are not limited to: amitriptyline (Elavil®), desipramine (Norpramin®), doxepine (Sinequan®), Imipramine (Tofranil®), nortriptyline (Pamelor®), amoxapine, clomipramine (Anafranil®), maprotiline (Ludiomil®), trimipramine (Surmontil®) and protriptyline (Vivactil®).

Monoamine Oxidase Inhibitors ("MAOIs"): MAOIs block the activity of monoamine oxidase, an enzyme that breaks down norepinephrine, serotonin, and dopamine in the brain and other parts of the body. MAOIs have many drug and food interactions and cause significant side effects in comparison to more current antidepressants. MAOIs include, for example, but are not limited to: phenelzine (Nardil®), selegiline (Emsam®), and tranylcypromine (Parnate®).

Atypical Antidepressants: Atypical antidepressants are considered "atypical," as these agents do not fit into any of the other classes of antidepressants. Each medicine in this category has a unique mechanism of action in the body. However, like other antidepressants, atypical antidepressants affect the levels of dopamine, serotonin, and norepinephrine in the brain. Brintellix® and Viibryd® inhibit reuptake of serotonin but also act on serotonin receptors. Atypical antidepressants include, for example, but are not limited to: bupropion (Wellbutrin®), mirtazapine (Remeron®), nefazodone (Serzone®), trazodone (Desyrel®) (Oleptro®), vilazodone (Viibryd®) and vortioxetine (Brintellix® In particular, being exposed to any of the agents/drugs set forth herein during the third trimester of pregnancy can cause unusual phenomena in a neonate/newborn including, for example, but not limited to: irritability, increased muscle tension, tremor, respiratory distress, vomiting and emissions, difficulty maintaining body temperature, problems in maintaining a normal sugar level, slow or fast heartbeat and bleeding. The incidence of these side effects can reach up to 30% of these babies (Hadassah Medical Center website). The symptoms may appear within about 2 to about 10 days or sooner after birth, and often appear at an age of just several hours.

Serotonin syndrome ("SS"):SS is a group of symptoms that may occur following use of certain serotonergic medications or drugs. The degree of symptoms can range from mild to severe. Symptoms include, for example, high body temperature, agitation, increased reflexes, tremor, sweating, dilated pupils and diarrhea. SS is typically caused by the use of two or more serotonergic medications or drug. This may include SSRIs, SNRIs, MAOIs, TCAs, amphetamines, pethidine(meperidine), tramadol, dextromethorphan, buspirone, L-tryptophan, 5-HTP, St.John's wort, triptans, ecstasy ("MDMA"), metoclopramide, ondansetron or cocaine. SS is known to occur in about 15% of SSRI overdoses. SS is a predictable consequence of excess serotonin on the central nervous system ("CNS"). Typically, the onset of symptoms is observed within about a day of the extra serotonin.

Stimulant or Psychostimulant Drug Agent

Stimulants may exhibit a wide variety of mechanisms. For example, many stimulants exert their effects through manipulations of monoamine neuro-transmission. Monoamines are a class of neurotransmitter relevant in reward, motivation, temperature regulation and pain sensation that include dopamine, norepinephrine, and serotonin. Stimulants usually block the reuptake or stimulate the efflux of dopamine and norepinephrine resulting in increased activity of their circuits. Some stimulants, notably those with empathogenic and hallucinogenic effects alter serotonergic neurotransmission. Interference with vesicular storage, activating amine associated ("TAAR1"), and reversing the flow of monoamine transporters may play a mechanism in the activity of these drugs. Adrenergic stimulants, such as ephedrine, may act by directly binding and activating the receptors that norepinephrine and epinephrine normally bind to (adrenergic receptors), producing sympathomimetic effects.

Some drugs, such as MDMA and derivatives may decrease regulatory capability by antagonizing regulatory pre-synaptic auto receptors. Caffeine is a notable exception, as it exerts its effects by antagonizing adenosine receptors instead of acting directly on monoamines.

Amphetamines: Amphetamines are a potent CNS stimulant of the phenethylamine class that is approved for the treatment of attention deficit hyperactivity disorder ("ADHD") and narcolepsy (Adderall® XR prescribing information, United States Food and Drug administration (2013)). Amphetamine was discovered in 1887 and exists as two enantiomers: levoamphetamine and dextroamphetamine (Heal et al., *J. Psychopharmacol.*, 27(6):479-496 (2013)). Amphetamine refers to equal parts of the enantiomers, that is 50% levoamphetamine and 50% dextroamphetamine. Amphetamine is also used as a performance and cognitive enhancer and recreationally as an aphrodisiac and euphoriant.

The first pharmaceutical amphetamine was Benzedrine®, a brand of inhalers used to treat a variety of conditions. As the dextro-isomer has greater stimulant properties, Benzedrine was gradually discontinued in favor of formulations containing all or mostly dextroamphetamine. Presently it is typically prescribed as Adderall®, dextroamphetamine ("Dexedrine"), or the inactive pro-drug lisdexamfetamine ("Vyvanse®"). In high doses, amphetamines are likely to impair cognitive function and induce rapid muscle breakdown.

Substituted amphetamines are a class of compounds based upon the amphetamine structure and includes all derivative compounds that are formed by replacing or substituting one or more hydrogen atoms in the amphetamine core structure with substituents. Examples of substituted amphetamines are amphetamine (itself), methamphetamine, ephedrine, cathinone, phentermine, mephentermine, bupropion, methoxyphenamine, selegiline, amfepramone, pyrovalerone, MDMA ("ecstasy") and DOM ("STP"). Many drugs in this class work primarily by activating TAAR1, in turn, this causes reuptake inhibition and effluxion, or release, of dopamine, norepinephrine and serotonin. An additional mechanism of some substituted amphetamine is the release of vesicular stores of monoamine neurotransmitters through VMAT2, thereby increasing the concentration of these neurotransmitters in the cytosol, or intracellular fluid, of the presynaptic neuron.

Cocaine and cocaine analogues:Cocaine is a serotonin-norepinephrine-dopamine reuptake inhibitor ("SNDRI"), also known as a triple reuptake inhibitor ("TRI") and is a type of drug that acts as a combined reuptake inhibitor of the monoamine neurotransmitters serotonin, norepinephrine and dopamine. There are five known dopamine receptors: D1-like receptors (D1 and D5), and D2-like receptors (D2, D3, and D4). The roles of dopamine and these receptors in reward pathways have been demonstrated in both human and animal model. Dopamine receptors are also located in the prefrontal cortex, hypothalamus and brainstem. Cocaine is a stimulant but is not normally prescribed therapeutically for its stimulant properties, although it sees clinical use as a local anesthetic, in particular in ophthalmology. Other tropane derivative drugs related to cocaine are also known such as troparil and lometopane. Hundreds of cocaine analogues have been created, all of them usually maintaining a benzyloxy connected to the 3-carbon of a tropane. Various modifications include substitutions on the benzene ring, as well as additions or substitutions in place of the normal carboxylate on the tropane 2-carbon. Various compound with similar structure activity relationships to cocaine that aren't technically analogues have been developed as well.

Caffeine:Caffeine is a stimulant compound belonging to the xanthine class of chemicals naturally found in coffee, tea, and (to a lesser degree) cocoa or chocolate. It is included in many soft drinks, as well as a larger amount in energy drinks. Caffeine is the world's most widely used psychoactive drug and by far the most common stimulant. In North America, 90% of adults consume caffeine daily. A few jurisdictions restrict its sale and use. Caffeine is also included in some medications, usually for the purpose of enhancing the effect of the primary ingredient or reducing one of its side-effects (especially drowsiness). Tablets containing standardized doses of caffeine are also widely available.

Caffeine's mechanism of action differs from many stimulants, as it produces stimulant effects by inhibiting adenosine receptors. Adenosine receptors are thought to be a large driver of drowsiness and sleep, and their action increases with extended wakefulness. Caffeine has been found to increase striatal dopamine in animal models, as well as inhibit the inhibitory effect of adenosine receptors on dopamine receptors, however the implications for humans are unknown.

Ephedrine: Ephedrine is a sympathomimetic amine that is similar in molecular structure to the well-known drugs phenylpropanolamine and methamphetamine, as well as to the important neurotransmitter epinephrine (adrenaline). Ephedrine is commonly used as a stimulant, appetite suppressant, concentration aid and decongestant, and to treat hypotension associated with anesthesia. In chemical terms, it is an alkaloid with a phenethylamine skeleton found in various plants in the genus Ephedra (family Ephedraceae). It works mainly by increasing the activity of norepinephrine (noradrenaline) on adrenergic receptors. It is most usually marketed as the hydrochloride or sulfate salt. The herb má huáng (Ephedra sinica), used in traditional Chinese medicine, contains ephedrine and pseudoephedrine as its principal active constituents. The same may be true of other herbal products containing extracts from other Ephedra species.

3,4-Methylenedioxymethamphetamine: 3,4-Methylenedioxymethamphetamine ("MDMA," "ecstasy," or "molly") is a euphoriant, empathogen and stimulant of the amphetamine class. MDMA is known for its entactogenic properties. The stimulant effects of MDMA include, for example, hypertension, anorexia, euphoria, social disinhibition, insomnia, improved energy, increased arousal and increased perspiration. MDMA differs from most stimulants in that its primary pharmacological effect is on the neurotransmitter serotonin rather than dopamine or norepinephrine.

Methylenedioxypyrovalerone: ("MDPV")Methylenedioxypyrovalerone ("MDPV") is a psychoactive drug with stimulant properties that acts as a norepinephrine-dopamine reuptake inhibitor ("NDRI"). MDPV was first developed in the 1960s by a team at Boehringer Ingelheim (U.S. Pat. No. 3,478,050). Incidents of psychological and physical harm have been attributed to MDP.

Mephedrone: Mephedrone is a synthetic stimulant drug of the amphetamine and cathinone classes. Mephedrone is chemically similar to the cathinone compounds found in the khat plant of eastern Africa. It was first synthesized in 1929, however it did not become widely known until it was rediscovered in 2003. By 2007, mephedrone was reported to be available for sale on the Internet; by 2008 law enforcement agencies had become aware of the compound; and, by 2010, it had been reported in most of Europe, becoming particularly prevalent in the United Kingdom.

Methamphetamine:Methamphetamine is a neurotoxin and potent psychostimulant of the phenethylamine and amphetamine classes that is used to treat attention deficit hyperactivity disorder (ADHA) and obesity. Methamphetamine exists as two enantiomers, dextrorotary and levorotary. Methamphetamine may be sold illicitly, either as pure dextromethamphetamine or in a racemic mixture of the right- and left-handed molecules, for example, 50% levomethamphetamine and 50% dextromethamphetamine. Both dextromethamphetamine and racemic methamphetamine are schedule II controlled substances in the United States. In low doses, methamphetamine can cause an elevated mood and increase alertness, concentration, and energy in fatigued individuals. At higher doses, it can induce psychosis, rhabdomyolysis, and cerebral hemorrhage (Desoxyn® Prescribing Information, United States Food and Drug Administration (2013)).

Methamphetamine is known to have a high potential for abuse and addiction. Recreational use of methamphetamine may result in psychosis or lead to post-withdrawal syndrome, a withdrawal syndrome that can persist for months beyond the typical withdrawal period.

Methylphenidate: Methylphenidate is a stimulant drug that is often used in the treatment of ADHD and narcolepsy and occasionally to treat obesity in combination with diet restraints and exercise. Its effects at therapeutic doses include increased focus, increased alertness, decreased appetite, decreased need for sleep and decreased impulsivity. Methylphenidate is not usually used recreationally, but when it is used, its effects are very similar to those of amphetamines. Ritalin® LA is a form of methylphenidate that has a long duration of action.

Methylphenidate acts a norepinephrine-dopamine reuptake inhibitor, by blocking the norepinephrine transporter ("NET") and the dopamine transporter ("DAT").

Methylphenidate has a higher affinity for the dopamine transporter than for the norepinephrine transporter, and so its effects are mainly due to elevated dopamine levels caused by the inhibited reuptake of dopamine, however increased norepinephrine levels also contribute to various of the effects caused by the drug. Methylphenidate is sold in many forms and its most common trade name is the oral tablet Ritalin®, Concert® and the long-lasting transdermal patch Daytrana®.

Nicotine: Nicotine is the active chemical constituent in tobacco, which is available in many forms, including cigarettes, cigars, chewing tobacco, and smoking cessation aids such as nicotine patches, nicotine gum, and electronic cigarettes. Nicotine is used widely throughout the world for its stimulating and relaxing effects. Nicotine exerts its effects through the agonism of nicotinic acetylcholine receptor, resulting in multiple downstream effects such as increase in activity of dopaminergic neurons in the midbrain reward system, as well as the decreased expression of monoamine oxidase in the brain.

Phenylpropanolamine: Phenylpropanolamine ("PPA," "Accutrim®," and β-hydroxyamphetamine), also known as the stereoisomers norephedrine and norpseudoephedrine, is a psychoactive drug of the phenethylamine and amphetamine chemical classes that is used as a stimulant, decongestant, and anorectic agent. It is commonly used in prescription and over-the counter cough and cold preparations. In veterinary medicine, it is used to control urinary incontinence in dogs under trade names Propalin® and Proin®.

Propylhexedrine: Propylhexedrine ("Hexahydromethamphetamine," and Obesin) is a stimulant medication, sold over-the-counter in the United States as the cold medication Benzedrex®. Propylhexedrine is not an amphetamine, though it is structurally similar; it is instead a cycloalkylamine, and thus has stimulant effects somewhat less potent than similarly structured amphetamines, such as methamphetamine. An abuse potential for propylhexedrine may be limited due its primary route of administration, which is as an inhalant, mixed with lavender oil and menthol. Injection of the drug has been found to cause transient diplopia and brain stem dysfunction.

Pseudoephedrine: Pseudoephedrine is a sympathomimetic drug of the phenethylamine and amphetamine chemical classes. It may be used as a nasal/sinus decongestant, as a stimulant or as a wakefulness-promoting agent. The salts of pseudoephedrine hydrochloride and pseudoephedrine sulfate are found in many over-the-counter "OYC") preparations, either as a single ingredient or, more commonly, in combination with antihistamines, guaifenesin, dextromethorphan and/or paracetamol (acetaminophen) or another NSAID, such as aspirin or ibuprofen. It is also used as a precursor chemical in the production of methamphetamine.

*Catha edulis* ("Khat"): Khat contains a monoamine alkaloid called cathinone, a "keto-amphetamine," which is said to cause excitement, loss of appetite, and euphoria. In 1980, the World Health Organization (WHO) classified it as a drug of abuse that can produce mild to moderate psychological dependence. It is a controlled substance in some countries, for example, such as the United States, Canada and Germany.

Delivery of the Compositions

The oxytocin pharmaceutical composition may be adapted for mucosal administration (e.g., nasal, buccal, sublingual or ocular administration). In some embodiments, the composition may further comprise a device for mucosal delivery. In some embodiments, the composition is adapted for buccal, such as a buccal aerosol spray, and/or sublingual mucosal delivery, which may further comprise a device for buccal and/or sublingual mucosal administration, such as unit dose containers, pump sprays, droppers, squeeze bottles, airless and preservative-free sprays, nebulizers, dose inhalers and pressurized dose inhalers. In some embodiments, the composition is adapted for ocular delivery, which may further comprise a device for conjunctival administration, such as a dropper or a squeeze bottle. In some embodiments, the composition is adapted for intranasal administration, which may further comprise a device for intranasal administration, such as a dropper, pump spray, squeeze bottle, airless and preservative-free sprays, or a nasal pump apparatus, e.g., a nasal pump apparatus comprising a reservoir bottle attached to an aerosolizer.

The oxytocin pharmaceutical composition may also be adapted for subcutaneous delivery, intramuscular delivery, intravenous administration, such as a slow drip, or a suppository dosage form.

Intranasal drug delivery has been a topic of research and development for many years, although it has been only within the past decade that carrier systems have been devised which make delivery of substances effective. Intranasal delivery has a number of advantageous features including comparatively high bioavailability, rapid kinetics of absorption and avoidance of a first-pass effect in the liver. In some aspects of the invention, intranasal administration can allow for delivery of oxytocin to the nasal cavity and in other aspects, intranasal administration can allow for targeted delivery to the nerves of the nose and/or the brain. There are four distinct routes that the oxytocin pharmaceutical composition may follow when administered nasally: oral mucosa into the gastroenteral and respiratory systems; nasal vasculature into systemic circulation; olfactory nerve pathways into the olfactory bulb and surrounding lymphatic fluid; trigeminal nerve pathways to the brainstem.

Oxytocin may be delivered intranasally in any applicable forms, including but is not limited to a liquid formulation, a solid formulation (e.g., a dry powder formulation), a gel formulation or an emulsion formulation.

In embodiments where the combination of oxytocin and an alkaline earth metal are administered intranasally, the composition can be prepared as a liquid aerosol formulation combined with a dispersing agent and/or a physiologically acceptable diluent. Alternatively, dry powder aerosol formulations are contemplated, and may contain a finely divided solid form of the subject compound and a dispersing agent allowing for the ready dispersal of the dry powder particles. With either liquid or dry powder aerosol formulations, the formulation is aerosolized into small, liquid or solid particles in order to ensure that the aerosolized dose reaches the mucous membranes of the nasal passages or the lung. The term "aerosol particle" is used herein to describe a liquid or solid particle suitable of a sufficiently small particle diameter for nasal (in a range of about 1 micron to about 10 microns) or pulmonary (in a range of from about 2-5 microns) distribution to targeted mucous or alveolar membranes. Other considerations include the construction of the delivery device, additional components in the formulation, and particle characteristics. These aspects of nasal or pulmonary administration of drugs are well known in the art, and manipulation of formulations, aerosolization means, and construction of delivery devices, is within the level of ordinary skill in the art.

In some embodiments, the device for intranasal delivery is a nasal pump apparatus or device. In some embodiments, the nasal pump apparatus comprises a reservoir bottle attached to a pump actuator. In some embodiments, the pump actuator is metered to deliver a specified volume (e.g. about 1 µL to about 150 preferably about 5 µL to about 100 more preferably about 10 µL to about 50 µL) in a specified distribution of droplet sizes. In some embodiments, the nasal pump apparatus comprises a reservoir bottle attached to an aerosolizer. In some embodiments, the device for nasal administration functions irrespective of the pressure applied to the pump once a threshold value is reached.

In some embodiments, the device for intranasal delivery is designed for delivery of multiple doses of the oxytocin compositions or formulations. In other embodiments, the device is designed for delivery of a single metered dose of oxytocin. For example, a nasal pump apparatus may comprise a reservoir bottle attached to a pump actuator where the reservoir bottle holds multiple dose of the liquid formulation and the pump actuator is metered to deliver a specified volume that is a fraction of the liquid formulation held in the reservoir bottle. In some embodiments, the pump actuator is metered to deliver about 0.5 µL to about 50 µL of the liquid formulation per spray. The nasal pump apparatus may comprise a filter for preventing back flow in order to reduce contaminant (e.g., bacterial) ingress into the reservoir bottle. In some embodiments, the nasal pump apparatus comprises a metal-free path for delivery of the liquid formulation (e.g., a plastic path). In some embodiments, the pump apparatus uses plastic material that is stable to gamma radiation (used for sterilizing the nasal apparatus). In some embodiments, the device for intranasal delivery is equipped with a multi-dose pump comprising a microbial filter and an auto-blocking mechanism in the pump actuator, for example, a spray device described in U.S. Pat. No. 5,988,449.

In some embodiments, the device for intranasal delivery is a unit-dose metering spray device suited for single administration of the oxytocin formulation or composition. In some embodiments, the device for intranasal delivery is a multi-dose metering spray pump apparatus suited for repeated administrations of an oxytocin formulation or composition.

Drop size, plume volume and flow rate can be modified to target specific nasal regions. The liquid spray may provide droplet size between about 0.5 microns to about 50 microns in order to target olfactory and/or respiratory epithelium. Larger droplets primarily travel down the nasopharynx and are swallowed, while smaller droplets are targeted to the pulmonary tissue. The Mass Median Equivalent Aerodynamic Diameter (MMAD) is used to specify the drop size. The nasal mucosa in an adult human can generally absorb volumes of approximately 100 µL before saturation occurs, however in a neonate or infant, this volume will be significantly lower, for example, between about 0.5 µL to about 50 µL, and liquid begins to drip out of the nose.

In some embodiments, the oxytocin formulation or composition is contained in any one of the devices for intranasal delivery described herein, and wherein the concentration of the oxytocin is within any of the concentration ranges described herein.

Methods

In one aspect, the invention provides a method for treating NAS by administering to a subject in need thereof an effective dose of an oxytocin formulation or composition. In another aspect of the invention, it is understood a care provider may readily anticipate that at birth, it is medically likely, possible and/or probable that an infant will be afflicted with NAS and/or may need immediate treatment for NAS with the formulations or compositions of the invention, e.g., oxytocin, an analog or derivative of oxytocin, or an oxytocin receptor agonist. The likelihood of such a response by a care provider, is increased when the mother is known to have an addiction to one or more substances, suspected to have an addiction to one or more substances, and/or the mother has been diagnosed with an addiction to one or more of these substances.

As stated herein, it is to be appreciated by one of skill in the art that administration and employment of the methods provided herein are amenable to a plurality of medically situational variables (timing of administration). For example, wherein a neonate and/or infant is identified post-birth undergoes a surgical procedure, utilization of one of more drug agents may be necessary for performing the surgical procedure, which has the potential to place the neonate and/or infant at risk to experience one or more NAS symptoms. This surgical procedure may occur at any time post-birth and at any time during infancy, which includes, for example, up to a year or more post-birth. Additionally, it is to be appreciated the timing of a diagnosis of NAS may be delayed and/or variable. For example, treatment with the methods herein may begin at any time within about 30 days post-birth, as the appearance and/or diagnosis of symptoms associated with NAS may not be readily apparent immediately following birth. However, it is to be understood that the methods herein may be employed prophylactically. Moreover, it is to be appreciated that application of the methods and administration of the compositions may be administered at any time during a subject's life wherein NAS has been identified in the subject.

Thus, in some embodiments, an oxytocin containing formulation or composition is prophylactically administered and/or immediately administered to a subject at birth and the administration of the oxytocin formulation or composition continues in a frequency of administration (dosing) and for a period of time as determined and/or suggested by the medical team for a specific subject. Typical administration may also occur within about 1 hour post-birth, within about 2 hours post-birth, within about 3 hours post-birth, within about 4 hours post-birth, within about 5 hours post-birth, within about 6 hours post-birth, within about 7 hours post-birth, within about 8 hours post-birth, within about 9 hours post-birth, within about 10 hours post-birth, within about 11 hours post-birth, within about 12 hours post-birth, within about 13 hours post-birth, within about 14 hours post-birth, within about 15 hours post-birth, within about 16 hours post-birth, within about 17 hours post-birth, within about 18 hours post-birth, within about 19 hours post-birth, within about 20 hours post-birth, within about 21 hours post-birth, within about 22 hours post-birth, within about 23 hours post-birth, within about 24 hours post-birth, within about 36 hours post-birth, within about 48 hours post-birth, within about 72 hours post-birth, within about 96 hours post-birth, within about 5 days post-birth, within about 6 days post-birth or within about 7 days post-birth (about a week).

In other embodiments, an oxytocin containing formulation or composition is immediately administered to a subject and the administration of an oxytocin formulation or composition continues for a time period up to about 14 days after the subject has been diagnosed with, determined to be suffering from NAS or suspected of having NAS. In other embodiments, an oxytocin containing formulation or composition is immediately administered to a subject and the administration of the oxytocin formulation or composition continues for a time period up to about 21 days after the subject has been diagnosed with, determined to be suffering from NAS or suspected of having NAS. In some embodiments, an oxytocin containing formulation or composition is immediately administered to a subject and the administration of an oxytocin formulation or composition continues for a time period up to about 30 days after the subject has been diagnosed with, determined to be suffering from NAS or suspected of having NAS. In other embodiments, an oxytocin containing formulation or composition is immediately administered to a subject and the administration of the oxytocin formulation or composition continues for a time period up to about 45 days after the subject has been diagnosed with, determined to be suffering from NAS or suspected of having NAS. In some embodiments, an oxytocin containing formulation or composition is immediately administered to a subject and the administration of the oxytocin formulation or composition continues for a time period of up to about 60 days after the subject has been diagnosed with, determined to be suffering from NAS or suspected of having NAS. In other embodiments, an oxytocin containing formulation or composition is immediately administered to a subject and administration of oxytocin formulation or composition continues for a time period of up to about 90 days after the subject has been diagnosed with, determined to be suffering from NAS or suspected of having NAS.

In other embodiments, an oxytocin containing formulation or composition is immediately administered to a subject and the administration of the oxytocin formulation or composition continues for a time period of up to about 120 days after the subject has been diagnosed with, determined to be suffering from NAS or suspected of having NAS. In another embodiment, an oxytocin containing formulation or composition is prophylactically and/or immediately administered to a subject and the administration of the oxytocin formulation or composition continues for a time period of up to about 5 months after the subject has been diagnosed with, determined to be suffering from NAS or suspected of having NAS. In other embodiments, an oxytocin containing formulation or composition is immediately administered to a subject and the administration of the oxytocin formulation or composition continues for a time period of up to about 6 months after the subject has been diagnosed with, determined to be suffering from NAS or suspected of having NAS. In still other embodiments, an oxytocin containing formulation or composition is immediately administered to a subject and the administration of the oxytocin formulation or composition continues for a time period of up to about 7 months after the subject has been diagnosed with, determined to be suffering from NAS or suspected of having NAS.

In still another embodiment, an oxytocin containing formulation or composition is immediately administered to a subject and the administration of the oxytocin formulation or composition continues for a time period of up to about 8 months after the subject has been diagnosed with, determined to be suffering from NAS or suspected of having NAS. In still other embodiments, an oxytocin containing formulation or composition is immediately administered to a subject and administration of oxytocin formulation or composition continues for a time period of up to about 9 months after the subject has been diagnosed with, determined to be suffering from NAS or suspected of having NAS. In still other embodiments, an oxytocin containing formulation or composition is immediately administered to a subject and the administration of the oxytocin formulation or composition continues for a time period of up to about 10 months after the subject has been diagnosed with, determined to be suffering from NAS or suspected of having NAS. In still another embodiment, an oxytocin containing formulation or composition is immediately administered to a subject and administration of oxytocin formulation or composition continues for a time period of up to about 11 months after the subject has been diagnosed with, determined to be suffering from NAS or suspected of having NAS. In still other embodiments, an oxytocin containing formulation or composition is immediately administered to a subject and the administration of the oxytocin formulation or composition continues for a time period of up to about 12 months after the subject has been diagnosed with, determined to be suffering from NAS or suspected of having NAS.

In still other embodiments, an oxytocin containing formulation or composition is immediately administered to a subject and the administration of the oxytocin formulation or composition continues for a time period of up to about 18 months after the subject has been diagnosed with, determined to be suffering from NAS or suspected of having NAS. In still other embodiments, an oxytocin containing formulation or composition is immediately administered to a subject and the administration of the oxytocin formulation or composition continues for a time period of up to about 2 years after the subject has been diagnosed with, determined to be suffering from NAS or suspected of having NAS.

In some embodiments, an oxytocin containing formulation or composition is administered to a subject within the first hour of birth and the administration of the oxytocin formulation or composition continues for a time period of up to about 24 hours after the subject has been diagnosed with, determined to be suffering from NAS or suspected of having NAS. In other embodiments, an oxytocin containing formulation or composition is administered to a subject within the first hour of birth and the administration of the oxytocin formulation or composition continues for a time period of up to about 48 hours after the subject has been diagnosed with, determined to be suffering from NAS or suspected of having NAS. In some embodiments, an oxytocin containing formulation or composition is administered to a subject within the first hour of birth and the administration of the oxytocin formulation or composition continues for a time period of up to about 72 hours after the subject has been diagnosed with, determined to be suffering from NAS or suspected of having NAS. In some embodiments, an oxytocin containing formulation or composition is administered to a subject within the first hour of birth and the administration of the oxytocin formulation or composition continues for a time period of up to about 4 days after the subject has been diagnosed with, determined to be suffering from NAS or suspected of having NAS. In other embodiments, an oxytocin containing formulation or composition is administered to a subject within the first hour of birth and the administration of the oxytocin formulation or composition continues for a time period of up to about 5 days after the subject has been diagnosed with, determined to be suffering from NAS or suspected of having NAS. In some embodiments, an oxytocin containing formulation or composition is administered to a subject within the first hour of birth and the administration of the oxytocin formulation or composition continues for a time period of up to about 6 days after the subject has been diagnosed with, determined to be suffering from NAS or suspected of having NAS.

In some embodiments, an oxytocin containing formulation or composition is administered to a subject within the first hour of birth and the administration of the oxytocin formulation or composition continues for a time period of up to about 7 days after the subject has been diagnosed with, determined to be suffering from NAS or suspected of having NAS. In other embodiments, an oxytocin containing formulation or composition is administered to a subject within the first hour of birth and the administration of the oxytocin formulation or composition continues for a time period of up to about 8 days after the subject has been diagnosed with, determined to be suffering from NAS or suspected of having NAS. In yet other embodiments, an oxytocin containing formulation or composition is administered to a subject within the first hour of birth and the administration of the oxytocin formulation or composition continues for a time period of up to about 9 days after the subject has been diagnosed with, determined to be suffering from NAS or suspected of having NAS.

In some embodiments, an oxytocin containing formulation or composition is administered to a subject within the first hour of birth and the administration of the oxytocin formulation or composition continues for a time period of up to about 10 days after the subject has been diagnosed with, determined to be suffering from NAS or suspected of having NAS. In other embodiments, an oxytocin containing formulation or composition is administered to a subject within the first hour of birth and the administration of the oxytocin formulation or composition continues for a time period of up to about 11 days after the subject has been diagnosed with, determined to be suffering from NAS or suspected of having NAS. In some embodiments, an oxytocin containing formulation or composition is administered to a subject within the first hour of birth and the administration of the oxytocin formulation or composition continues for a time period of up to about 12 days after the subject has been diagnosed with, determined to be suffering from NAS or suspected of having NAS. In some embodiments, an oxytocin containing formulation or composition is administered to a subject within the first hour of birth and the administration of the oxytocin formulation or composition continues for a time period of up to about 13 days after the subject has been diagnosed with, determined to be suffering from NAS or suspected of having NAS. In other embodiments, an oxytocin containing formulation or composition is administered to a subject within the first hour of birth and the administration of the oxytocin formulation or composition continues for a time period of up to about 14 days after the subject has been diagnosed with, determined to be suffering from NAS or suspected of having NAS.

In yet other embodiments, an oxytocin containing formulation or composition is administered to a subject within the first hour of birth and the administration of the oxytocin formulation or composition continues for a time period of up to about 15 days after the subject has been diagnosed with, determined to be suffering from NAS or suspected of having NAS. In some embodiments, an oxytocin containing formulation or composition is administered to a subject within the first hour of birth and the administration of the oxytocin formulation or composition continues for a time period of up to about 16 days after the subject has been diagnosed with, determined to be suffering from NAS or suspected of having NAS. In other embodiments, an oxytocin containing formulation or composition is administered to a subject within the first hour of birth and the administration of the oxytocin formulation or composition continues for a time period of up to about 17 days after the subject has been diagnosed with, determined to be suffering from NAS or suspected of having NAS.

In some embodiments, an oxytocin containing formulation or composition is administered to a subject within the first hour of birth and the administration of the oxytocin formulation or composition continues for a time period of up to about 18 days after the subject has been diagnosed with, determined to be suffering from NAS or suspected of having NAS. In some embodiments, an oxytocin containing formulation or composition is administered to a subject within the first hour of birth and the administration of the oxytocin formulation or composition continues for a time period of up to about 19 days after the subject has been diagnosed with, determined to be suffering from NAS or suspected of having NAS. In other embodiments, an oxytocin containing formulation or composition is administered to a subject within the first hour of birth and the administration of the oxytocin formulation or composition continues for a time period of up to about 20 days after the subject has been diagnosed with, determined to be suffering from NAS or suspected of having NAS.

In yet other embodiments, an oxytocin containing formulation or composition is administered to a subject within the first hour of birth and the administration of the oxytocin formulation or composition continues for a time period of up to about 21 days after the subject has been diagnosed with, determined to be suffering from NAS or suspected of having NAS. In some embodiments, an oxytocin containing formulation or composition is administered to a subject within the first hour of birth and the administration of the oxytocin formulation or composition continues for a time period of up to about 22 days after the subject has been diagnosed with, determined to be suffering from NAS or suspected of having NAS. In other embodiments, an oxytocin containing formulation or composition is administered to a subject within the first hour of birth and the administration of the oxytocin formulation or composition continues for a time period of up to about 23 days after the subject has been diagnosed with, determined to be suffering from NAS or suspected of having NAS.

In some embodiments, an oxytocin containing formulation or composition is administered to a subject within the first hour of birth and the administration of the oxytocin formulation or composition continues for a time period of up to about 24 days after the subject has been diagnosed with, determined to be suffering from NAS or suspected of having NAS. In some embodiments, an oxytocin containing formulation or composition is administered to a subject within the first hour of birth and the administration of the oxytocin formulation or composition continues for a time period of up to about 25 days after the subject has been diagnosed with, determined to be suffering from NAS or suspected of having NAS. In other embodiments, an oxytocin containing formulation or composition is administered to a subject within the first hour of birth and the administration of the oxytocin formulation or composition continues for a time period of up to about 26 days after the subject has been diagnosed with, determined to be suffering from NAS or suspected of having NAS. In yet other embodiments, an oxytocin containing formulation or composition is administered to a subject within the first hour of birth and the administration of the oxytocin formulation or composition continues for a time period of up to about 27 days after the subject has been diagnosed with, determined to be suffering from NAS or suspected of having NAS.

In some embodiments, an oxytocin containing formulation or composition is administered to a subject within the first hour of birth and the administration of the oxytocin formulation or composition continues for a time period of up to about 28 days after the subject has been diagnosed with, determined to be suffering from NAS or suspected of having NAS. In other embodiments, an oxytocin containing formulation or composition is administered to a subject within the first hour of birth and the administration of the oxytocin formulation or composition continues for a time period of up to about 29 days after the subject has been diagnosed with, determined to be suffering from NAS or suspected of having NAS. In some embodiments, an oxytocin containing formulation or composition is administered to a subject within the first hour of birth and the administration of the oxytocin formulation or composition continues for a time period of up to about 30 days after the subject has been diagnosed with, determined to be suffering from NAS or suspected of having NAS.

In some embodiments, an oxytocin containing formulation or composition is administered to a subject within the first hour of birth and the administration of the oxytocin formulation or composition continues for a time period of up to about 45 days after the subject has been diagnosed with, determined to be suffering from NAS or suspected of having NAS. In other embodiments, an oxytocin containing formulation or composition is administered to a subject within the first hour of birth and the administration of the oxytocin formulation or composition continues for a time period of up to about 60 days after the subject has been diagnosed with, determined to be suffering from NAS or suspected of having NAS. In yet other embodiments, an oxytocin containing formulation or composition is administered to a subject within the first hour of birth and the administration of the oxytocin formulation or composition continues for a time period of up to about 90 days after the subject has been diagnosed with, determined to be suffering from NAS or suspected of having NAS.

In some embodiments, an oxytocin containing formulation or composition is administered to a subject within the first hour of birth and the administration of the oxytocin formulation or composition continues for a time period of up to about 120 days after the subject has been diagnosed with, determined to be suffering from NAS or suspected of having NAS. In other embodiments, an oxytocin containing formulation or composition is administered to a subject within the first hour of birth and the administration of the oxytocin formulation or composition continues for a time period of up to about 5 months after the subject has been diagnosed with, determined to be suffering from NAS or suspected of having NAS. In yet other embodiments, an oxytocin containing formulation or composition is administered to a subject within the first hour of birth and the administration of the oxytocin formulation or composition continues for a time period of up to about 6 months after the subject has been diagnosed with, determined to be suffering from NAS or suspected of having NAS.

In some embodiments, an oxytocin containing formulation or composition is administered to a subject within the first hour of birth and the administration of the oxytocin formulation or composition continues for a time period of up to about 7 months after the subject has been diagnosed with, determined to be suffering from NAS or suspected of having NAS. In other embodiments, an oxytocin containing formulation or composition is administered to a subject within the first hour of birth and the administration of the oxytocin formulation or composition continues for a time period of up to about 8 months after the subject has been diagnosed with, determined to be suffering from NAS or suspected of having NAS. In yet other embodiments, an oxytocin containing formulation or composition is administered to a subject within the first hour of birth and the administration of the oxytocin formulation or composition continues for a time period of up to about 9 months after the subject has been diagnosed with, determined to be suffering from NAS or suspected of having NAS.

In some embodiments, an oxytocin containing formulation or composition is administered to a subject within the first hour of birth and the administration of the oxytocin formulation or composition continues for a time period of up to about 10 months after the subject has been diagnosed with, determined to be suffering from NAS or suspected of having NAS. In other embodiments, an oxytocin containing formulation or composition is administered to a subject within the first hour of birth and the administration of the oxytocin formulation or composition continues for a time period of up to about 11 months after the subject has been diagnosed with, determined to be suffering from NAS or suspected of having NAS. In yet other embodiments, an oxytocin containing formulation or composition is administered to a subject within the first hour of birth and the administration of the oxytocin formulation or composition continues for a time period of up to about 12 months after the subject has been diagnosed with, determined to be suffering from NAS or suspected of having NAS.

In yet other embodiments, an oxytocin containing formulation or composition is administered to a subject between about 2 hours and about 7 days after the subject has been diagnosed with or determined to be suffering from NAS. In some embodiments, an oxytocin containing formulation or composition is administered to a subject between about 3 hours and about 7 days after the subject has been diagnosed with or determined to be suffering from NAS. In some embodiments, an oxytocin containing formulation or composition is administered to a subject between about 4 hours and about 7 days after the subject has been diagnosed with or determined to be suffering from NAS. In some embodiments, an oxytocin containing formulation or composition is administered to a subject between about 5 hours and about 7 days after the subject has been diagnosed with or determined to be suffering from NAS. In some embodiments, an oxytocin containing formulation or composition is administered to a subject between about 6 hours and about 7 days after the subject has been diagnosed with or determined to be suffering from NAS. In some embodiments, an oxytocin containing formulation or composition is administered to a subject between about 7 hours and about 7 days after the subject has been diagnosed with or determined to be suffering from NAS.

In some embodiments, an oxytocin containing formulation or composition is administered to a subject between about 8 hours and about 7 days after the subject has been diagnosed with or determined to be suffering from NAS. In some embodiments, an oxytocin containing formulation or composition is administered to a subject between about 9 hours and about 7 days after the subject has been diagnosed with or determined to be suffering from NAS. In some embodiments, an oxytocin containing formulation or composition is administered to a subject between about 10 hours and about 7 days after the subject has been diagnosed with or determined to be suffering from NAS. In some embodiments, an oxytocin containing formulation or composition is administered to a subject between about 11 hours and about 7 days after the subject has been diagnosed with or determined to be suffering from NAS. In some embodiments, an oxytocin containing formulation or composition is administered to a subject between about 12 hours and about 7 days after the subject has been diagnosed with or determined to be suffering from NAS. In some embodiments, an oxytocin containing formulation or composition is administered to a subject between about 13 hours and about 7 days after the subject has been diagnosed with or determined to be suffering from NAS.

In some embodiments, an oxytocin containing formulation or composition is administered to a subject between about 14 hours and about 7 days after the subject has been diagnosed with or determined to be suffering from NAS. In some embodiments, an oxytocin containing formulation or composition is administered to a subject between about 15 hours and about 7 days after the subject has been diagnosed with or determined to be suffering from NAS. In some embodiments, an oxytocin containing formulation or composition is administered to a subject between about 16 hours and about 7 days after the subject has been diagnosed with or determined to be suffering from NAS. In some embodiments, an oxytocin containing formulation or composition is administered to a subject between about 17 hours and about 7 days after the subject has been diagnosed with or determined to be suffering from NAS. In some embodiments, an oxytocin containing formulation or composition is administered to a subject between about 18 hours and about 7 days after the subject has been diagnosed with or determined to be suffering from NAS. In some embodiments, an oxytocin containing formulation or composition is administered to a subject between about 19 hours and about 7 days after the subject has been diagnosed with or determined to be suffering from NAS. In some embodiments, an oxytocin containing formulation or composition is administered to a subject between about 20 hours and about 7 days after the subject has been diagnosed with or determined to be suffering from NAS.

In some embodiments, an oxytocin containing formulation or composition is administered to a subject between about 21 hours and about 7 days after the subject has been diagnosed with or determined to be suffering from NAS. In some embodiments, an oxytocin containing formulation or composition is administered to a subject between about 22 hours and about 7 days after the subject has been diagnosed with or determined to be suffering from NAS. In some embodiments, an oxytocin containing formulation or composition is administered to a subject between about 23 hours and about 7 days after the subject has been diagnosed with or determined to be suffering from NAS. In some embodiments, an oxytocin containing formulation or composition is administered to a subject between about 24 hours and about 7 days after the subject has been diagnosed with or determined to be suffering from NAS.

In other embodiments, an oxytocin containing formulation or composition is administered to a subject immediately post-birth and/or between about 1 hour and about 96 hours after the subject has been diagnosed with, determined to be suffering from NAS of suspected of having NAS or has the potential to be a NAS neonate. In some embodiments, an oxytocin containing formulation or composition is administered to a subject between about 2 hours and about 96 hours after the subject has been diagnosed with or determined to be suffering from NAS. In some embodiments, an oxytocin containing formulation or composition is administered to a subject between about 3 hours and about 96 hours after the subject has been diagnosed with or determined to be suffering from NAS.

In some embodiments, an oxytocin containing formulation or composition is administered to a subject between about 4 hours and about 96 hours after the subject has been diagnosed with or determined to be suffering from NAS. In some embodiments, an oxytocin containing formulation or composition is administered to a subject between about 5 hours and about 96 hours after the subject has been diagnosed with or determined to be suffering from NAS. In some embodiments, an oxytocin containing formulation or composition is administered to a subject between about 6 hours and about 96 hours after the subject has been diagnosed with or determined to be suffering from NAS. In some embodiments, an oxytocin containing formulation or composition is administered to a subject between about 7 hours and about 96 hours after the subject has been diagnosed with or determined to be suffering from NAS. In some embodiments, an oxytocin containing formulation or composition is administered to a subject between about 8 hours and about 96 hours after the subject has been diagnosed with or determined to be suffering from NAS.

In some embodiments, an oxytocin containing formulation or composition is administered to a subject between about 9 hours and about 96 hours after the subject has been diagnosed with or determined to be suffering from NAS. In some embodiments, an oxytocin containing formulation or composition is administered to a subject between about 10 hours and about 96 hours after the subject has been diagnosed with or determined to be suffering from NAS. In some embodiments, an oxytocin containing formulation or composition is administered to a subject between about 11 hours and about 96 hours after the subject has been diagnosed with or determined to be suffering from NAS. In some embodiments, an oxytocin containing formulation or composition is administered to a subject between about 12 hours and about 96 hours after the subject has been diagnosed with or determined to be suffering from NAS. In some embodiments, an oxytocin containing formulation or composition is administered to a subject between about 13 hours and about 96 hours after the subject has been diagnosed with or determined to be suffering from NAS.

In some embodiments, an oxytocin containing formulation or composition is administered to a subject between about 14 hours and about 96 hours after the subject has been diagnosed with or determined to be suffering from NAS. In some embodiments, an oxytocin containing formulation or composition is administered to a subject between about 15 hours and about 96 hours after the subject has been diagnosed with or determined to be suffering from NAS. In some embodiments, an oxytocin containing formulation or composition is administered to a subject between about 16 hours and about 96 hours after the subject has been diagnosed with or determined to be suffering from NAS. In some embodiments, an oxytocin containing formulation or composition is administered to a subject between about 17 hours and about 96 hours after the subject has been diagnosed with or determined to be suffering from NAS. In some embodiments, an oxytocin containing formulation or composition is administered to a subject between about 18 hours and about 96 hours after the subject has been diagnosed with or determined to be suffering from NAS.

In some embodiments, an oxytocin containing formulation or composition is administered to a subject between about 19 hours and about 96 hours after the subject has been diagnosed with or determined to be suffering from NAS. In some embodiments, an oxytocin containing formulation or composition is administered to a subject between about 20 hours and about 96 hours after the subject has been diagnosed with or determined to be suffering from NAS. In some embodiments, an oxytocin containing formulation or composition is administered to a subject between about 21 hours and about 96 hours after the subject has been diagnosed with or determined to be suffering from NAS. In some embodiments, an oxytocin containing formulation or composition is administered to a subject between about 22 hours and about 96 hours after the subject has been diagnosed with or determined to be suffering from NAS. In some embodiments, an oxytocin containing formulation or composition is administered to a subject between about 23 hours and about 96 hours after the subject has been diagnosed with or determined to be suffering from NAS. In some embodiments, an oxytocin containing formulation or composition is administered to a subject between about 24 hours and about 96 hours after the subject has been diagnosed with or determined to be suffering from NAS.

Frequency of administration will be clinically determined as to what is necessary for each individual neonate, infant, neonate toddler, child, pre-adolescent, adolescent or adult. Administration of an oxytocin formulation or composition to the subject may be, for example, as a slow infusion, or as described above, QD, b.i.d., t.i.d., q.i.d, q.a.d, q.l., q.s or p.r.n.

The oxytocin formulation or composition may be administered via the same route or different routes to a subject in need thereof as described above.

In some embodiments, the oxytocin formulation or composition is administered via intranasal administration. The oxytocin formulation or composition can be administered to the mucosa tissue within the nasal cavity using a suitable device for intranasal delivery such as a nasal delivery device described herein. Suitable regions within the nasal cavity include, but are not limited to, the inferior two-thirds of the nasal cavity, or the upper third, or the entire nasal passage. In some embodiments, the oxytocin formulation or composition is administered to the upper third of the nasal cavity. In some embodiments, the oxytocin formulation or composition is administered to the lower two thirds of the nasal cavity. In some embodiments, the oxytocin formulation or composition is administered specifically to reach both the lower two thirds and the upper third of the nasal cavity. In some embodiments, a method is provided for treating NAS by intranasally administering to a subject in need thereof an effective dose of the oxytocin formulation or composition.

Kits

Provided herein are kits for carrying out any of the methods described herein. Kits are provided for use in treatment, prevention or amelioration of the symptoms associated with NAS. In some embodiments, the kit contains an oxytocin formulation or composition for mucosal administration (e.g., intranasal administration) in suitable packaging. Kits may further contain specific adjuvants, diluents, agents, such as, a protease inhibitor and/or at least one absorption enhancer. Other kits may further include instructions providing information to the user and/or health care provider for carrying out any one of the methods described herein.

Also provided is a kit containing an oxytocin formulation or composition described herein contained in a device for mucosal administration (e.g., a device for intranasal administration such as a nasal pump apparatus) and suitable packaging. The kit may further include instructions for administering the oxytocin formulation or composition to a subject in need thereof.

The instructions relating to the use of the kit for carrying out the invention generally describe how the contents of the kit are used to carry out the methods of the invention. Instructions supplied in the kits of the invention are typically written instructions on a label or package insert (e.g., a paper sheet included in the kit), but machine-readable instructions (e.g., instructions carried on a magnetic or optical storage disk) are also acceptable.

EXAMPLES

The invention can be further understood by reference to the following examples, which are provided by way of illustration and are not meant to be limiting.

Example 1: Oxytocin Reduces Naloxone-Induced Withdrawal Symptoms in Rat Pups Chronically Exposed to Morphine Prenatally This example demonstrates the ability of oxytocin to attenuate naloxone-induced withdrawal symptoms in rat pups chronically exposed to an opioid analgesic agent prenatally. Beginning on the second day of gestation, timed-pregnant Sprague-Dawley rats (n=3) were treated with escalating doses (20-60 mg/kg/day) of morphine administered daily by subcutaneous injection for the entire period of gestation (approximately 21 days); Upon birth, rat pups were fostered by drug-naïve surrogate Sprague-Dawley rats (n=3) that had recently given birth to their own litter; On postnatal day one, a total of n=10 rat pups having been exposed to morphine prenatally, were each placed in to an automated SmartCage™ for 15 minutes and baseline locomotor activity was assessed; All animals were then injected subcutaneously with the opioid receptor antagonist naloxone to rapidly induce an opioid withdrawal syndrome; Immediately following treatment with naloxone, half of the rat pups (n=5) were injected subcutaneously with 2 mg/kg oxytocin and the other half of the animals (n=5) were injected subcutaneously with 0.9% saline; Animals were then placed back in to the SmartCage™ and locomotor activity was measured for an additional 45 minutes; In addition, animals were video recorded during the entire experiment and this footage was used as a visual aid to hand score rates of rolling, curling, and stretching behavior; All of these behaviors are associated symptoms of opioid withdrawal in rat pups.

Compared to the saline treated rat pups, a clear statistically significant reduction in locomotor activity (FIG. 1a) was observed for up to 30 minutes post-naloxone treatment for rat pups treated with single doses of 2 mg/kg oxytocin.

Figure 1C:
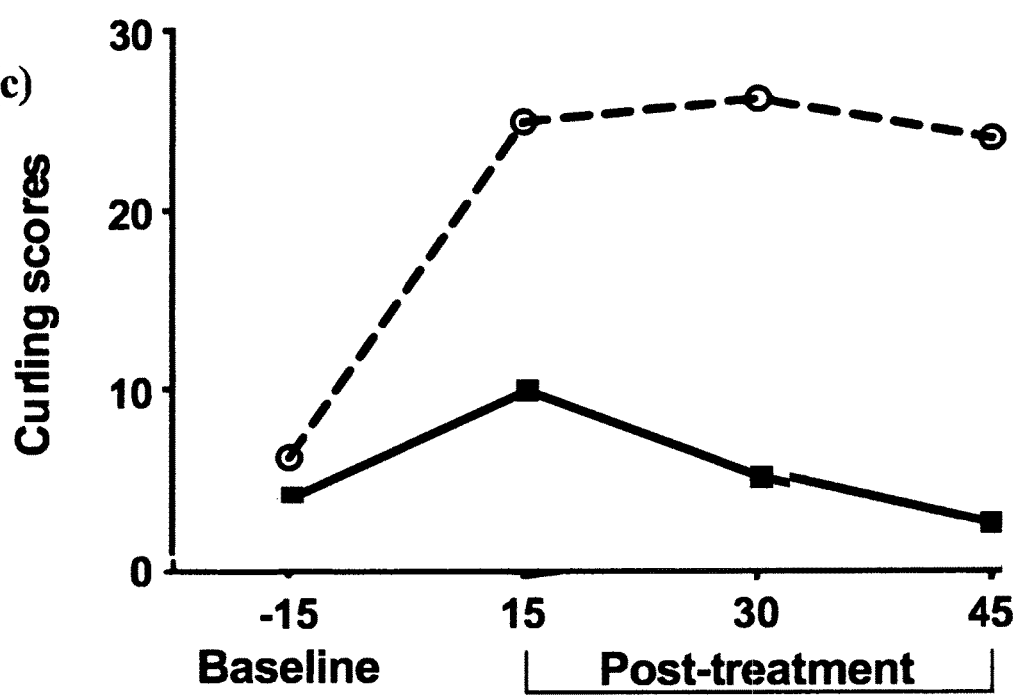

Compared to the saline treated rat pups, a numerical reduction in scores of rolling (FIG. 1b) and curling (FIG. 1c) behavior were observed for up to 45 minutes in rat pups treated with single doses of 2 mg/kg oxytocin.

Figure 1D:
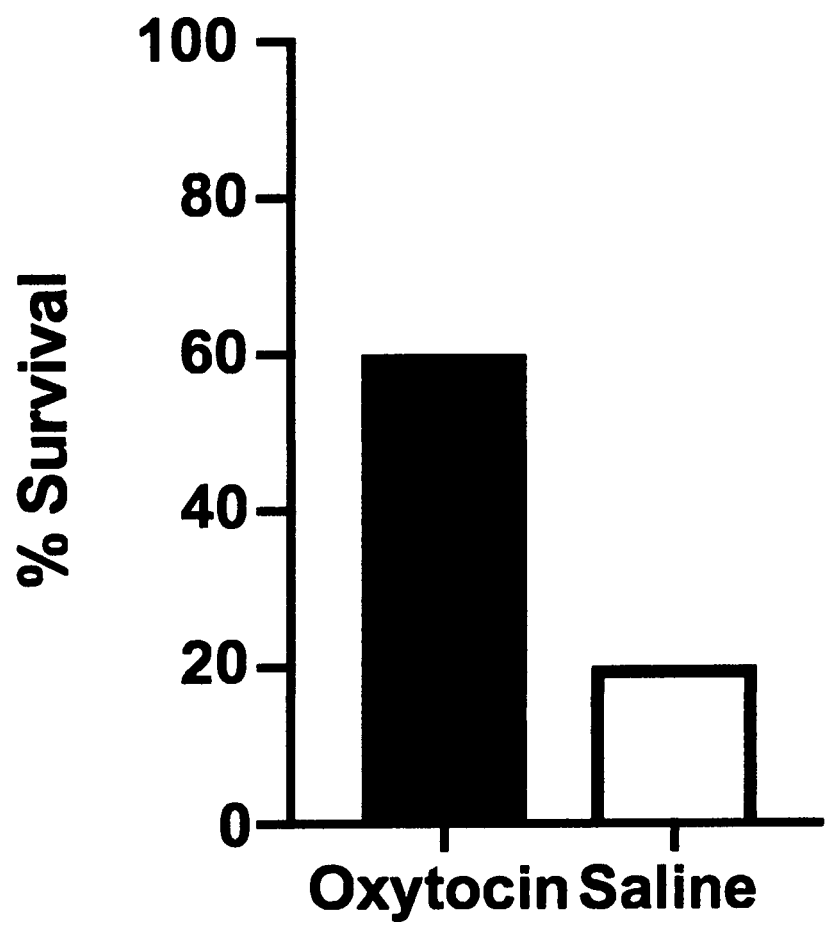

Compared to the saline treated rat pups, an unexpected finding for improved percentage survival rates at postnatal day 10 was also shown for rat pups treated with a single dose of 2 mg/kg oxytocin (FIG. 1d); This led to further research aimed at determining oxytocin's ability to reduce mortality rates in animals exposed to drugs prenatally.

Example 2: Neonatal Oxytocin Treatment Reduces Mortality in Rat Pups Chronically Exposed to Morphine Prenatally This example demonstrates the ability of neonatal oxytocin treatment to improve survival rates in rat pups chronically exposed to an opioid analgesic agent prenatally.

Beginning on the second day of gestation, timed-pregnant Sprague-Dawley rats (n=4) were treated with daily escalating doses (10-50 mg/kg/day) of morphine administered by subcutaneous injection for the entire period of gestation (approximately 21 days); Upon birth, rat pups were fostered by drug-naïve surrogate Sprague-Dawley rats (n=4) that had recently given birth to their own litter; Rat pups having been exposed to morphine prenatally, were dosed daily with either 2 mg/kg oxytocin or 0.9% saline (n=18/group) by subcutaneous injection for the first 10 postnatal days; Survival rates were measured for 15 days and body weight was measured during daily dosing and at postnatal day 31.

Figure 2C:
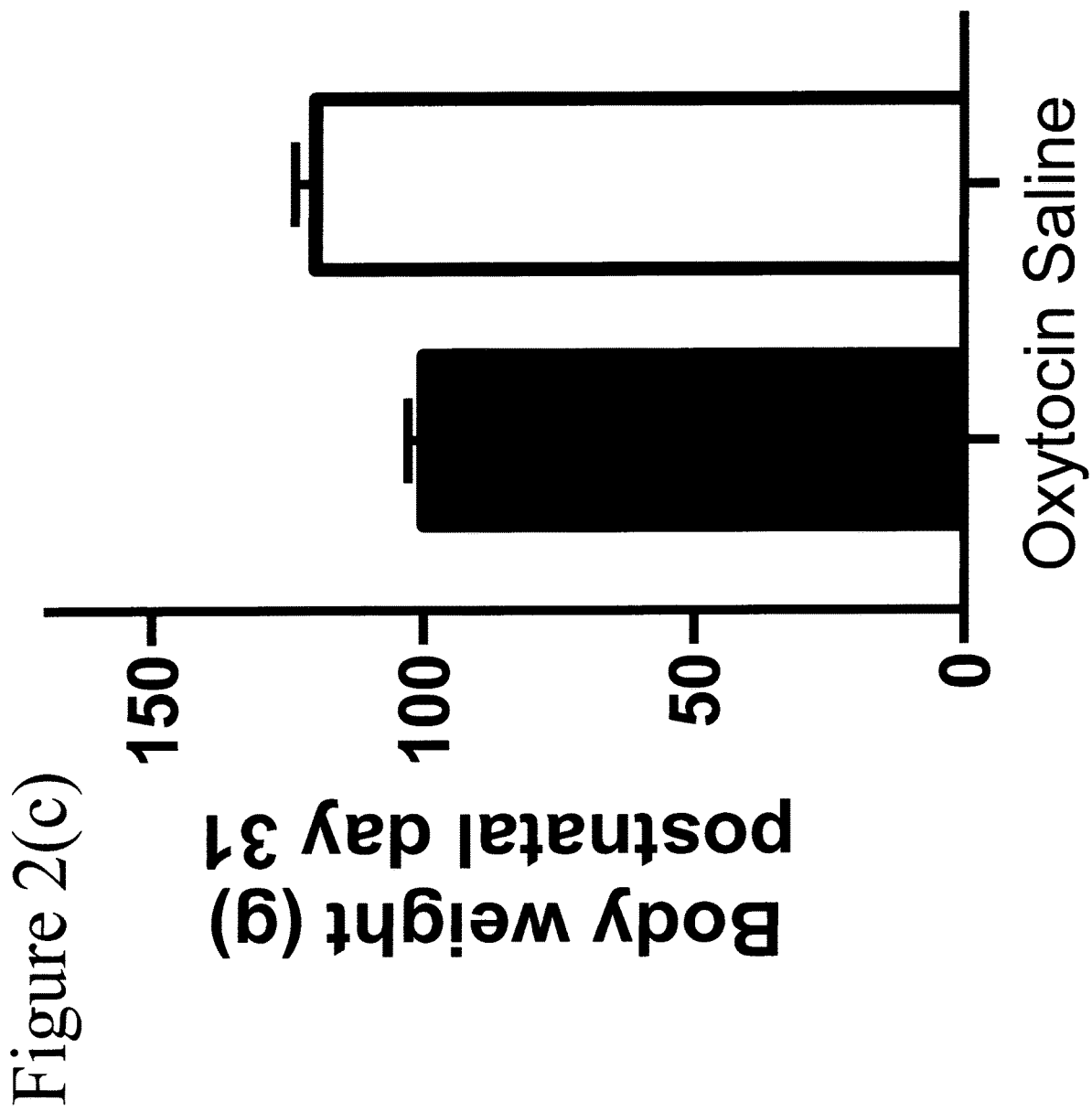

Compared to the saline treated rat pups, a clear statistically significant improvement in percentage survival rates was noted for rat pups that had been treated with daily doses of 2 mg/kg oxytocin (FIG. 2a) for the first 10 postnatal days.

Compared to the saline treated rat pups, a clear statistically significant reduction in body weight for the last four days of daily dosing (FIG. 2b), persisting until postnatal day 31 (FIG. 2c), was noted for rat pups that had been treated with daily injections of 2 mg/kg oxytocin for the first 10 postnatal days.

Example 3: Neonatal Oxytocin Treatment Reduces Mortality in Rat Pups Chronically Exposed to Diazepam Prenatally This example demonstrates the ability of oxytocin treatment to improve survival rates in rat pups chronically exposed to a benzodiazepine sedating agent prenatally.

Beginning on the second day of gestation, timed-pregnant Sprague-Dawley rats (n=2) were treated with daily escalating doses (2-15 mg/kg/day) of diazepam administered by subcutaneous injection for the entire period of gestation (approximately 21 days); Upon birth, rat pups were fostered by drug-naïve surrogate Sprague-Dawley rats (n=2) that had recently given birth to their own litter; Rat pups having been exposed to diazepam prenatally, were dosed daily with either 2 mg/kg oxytocin or 0.9% saline (n=13/group) by subcutaneous injection for the first 10 postnatal days; Survival rates were measured for 15 days and body weight was measured during daily dosing and at postnatal day 31.

Figure 3C:
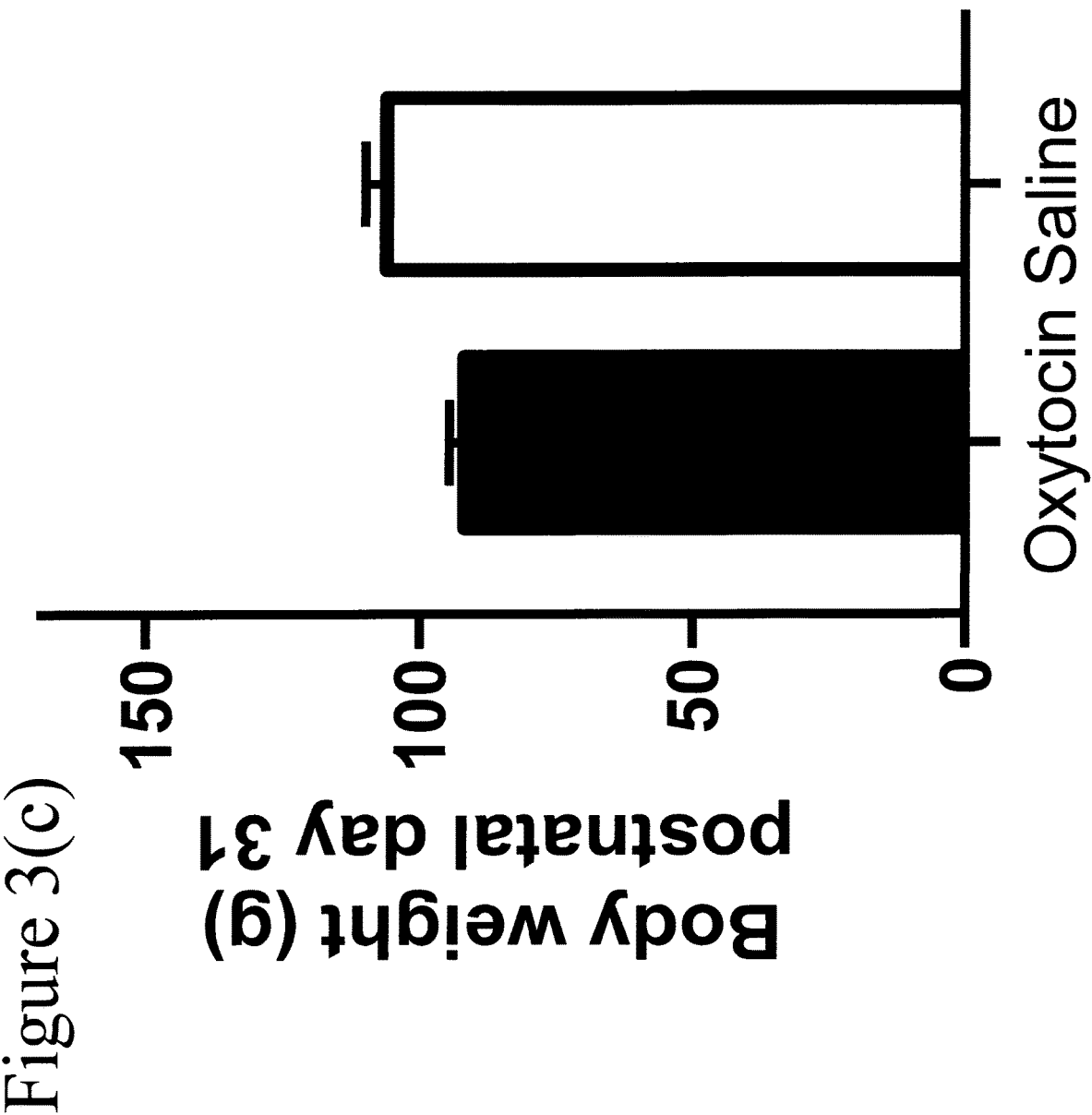

Compared to the saline treated rat pups, a clear statistically significant improvement in percentage survival rates was noted for rat pups that had been treated with daily injections of 2 mg/kg oxytocin (FIG. 3a) for the first 10 postnatal days.

Compared to the saline treated rat pups, a clear statistically significant increase in body weight throughout various time points of the dosing period was noted for rat pups that had been treated with daily injections of 2 mg/kg (FIG. 3b) for the first 10 postnatal days.

Conversely, compared to saline treated animals, a clear statistically significant decrease in body weight at postnatal day 31 was noted for animals treated with daily injections of 2 mg/kg oxytocin (FIG. 3c) for the first 10 postnatal days.

Example 4: Neonatal Oxytocin Treatment Reduces Mortality in Rat Pups Chronically Exposed To Fluoxetine Prenatally This example demonstrates the ability of oxytocin treatment to improve survival in rat pups chronically exposed to an antidepressant agent prenatally.

Beginning on the second day of gestation, timed-pregnant Sprague-Dawley rats (n=3) were treated with daily escalating doses (2-10 mg/kg/day) of fluoxetine administered by subcutaneous injection for the entire period of gestation (approximately 21 days); Upon birth, rat pups were fostered by drug-naïve surrogate Sprague-Dawley rats (n=4) that had recently given birth to their own litter; Rat pups having been exposed to fluoxetine prenatally, were dosed daily with either 2 mg/kg oxytocin or 0.9% saline (n=17/group) by subcutaneous injection for the first 10 postnatal days; Survival rates were measured for 15 days and body weight was measured during daily dosing and at postnatal day 36.

Figure 4C:
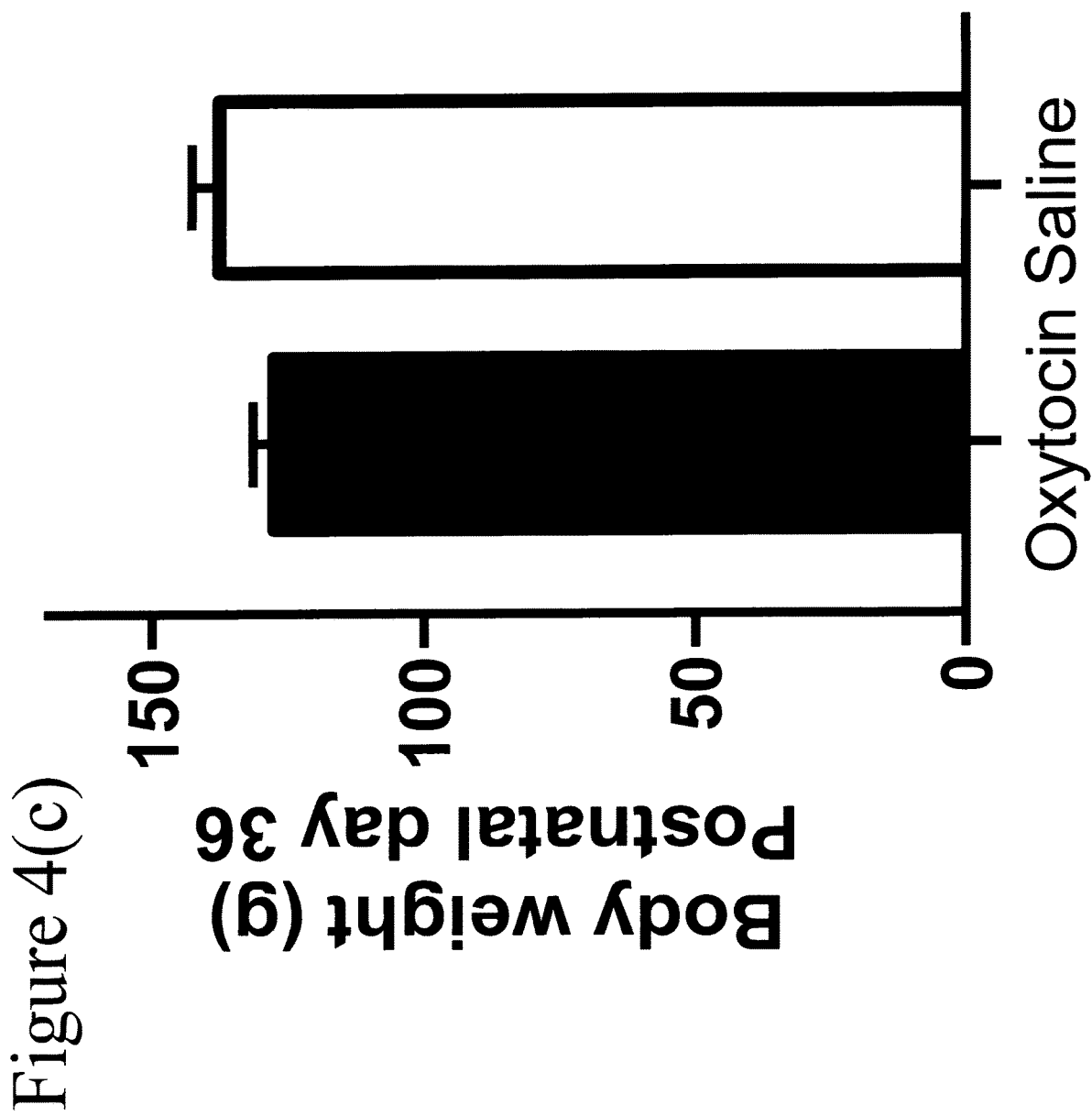

Compared to the saline treated rat pups, a statistical trend towards improvement in percentage survival rates was noted for rat pups that had been treated with daily injections of 2 mg/kg oxytocin (FIG. 4a) for the first 10 postnatal days.

Body weights were comparable during the first 10 postnatal days between animals treated with daily injections of 2 mg/kg oxytocin or saline (FIG. 4b) for the first 10 postnatal days.

Compared to the saline treated animals, a clear statistically significant reduction in body weight at postnatal day 36 was noted for animals treated with daily injections of 2 mg/kg oxytocin (FIG. 4c) for the first 10 postnatal days.

Example 5: Neonatal Oxytocin Treatment Improves Learning and Memory Function in Adolescent Rats Chronically Exposed to Fluoxetine Prenatally This example demonstrates the ability of oxytocin treatment during neonate development to improve adolescent memory function in rats chronically exposed to an antidepressant agent prenatally.

Between postnatal days 31 and 35, surviving animals that were exposed to fluoxetine prenatally and treated with subcutaneous injections of 2 mg/kg oxytocin (n=16) or 0.9% saline (n=12) during the first 10 postnatal days underwent testing for locomotor activity, anxiety-like behavior as measured by the Light/Dark Box, and learning and memory function as measured by the Passive Avoidance Test.

Briefly, locomotor activity is measured by placing an animal in to a small standardized test chamber for a five-minute period. Distance travelled, and time spent active is measured automatically using a SmartCage™.

Briefly, the Light/Dark Box is a characteristic tool used in the assessment of anxiety-like behavior; The apparatus consists of a simple test chamber divided in to a dark and a light compartment; Rodents prefer darker areas over lighter areas: however, when presented in a novel environment, rodents have a tendency to explore; These two conflicting emotions lead to observable anxiety-like behavior; Compounds with anxiolytic properties will increase the amount of time that an animal spends exploring the light compartment; Time spent in each compartment is automatically measured using a SmartCage™.

Briefly, in the Passive Avoidance Test an animal learns to avoid an unpleasant stimulus by inhibiting locomotion and exploration; On the training day, rats are placed in a brightly lit compartment of a test chamber; The animal quickly moves in to an adjacent dark compartment of the test chamber and receives an unavoidable mild foot shock; Twenty-four hours later during the test phase, the animals are again placed in to the light compartment and the latency to re-enter the dark compartment is measured. Latency to enter a compartment is automatically measured using a SmartCage™.

Figure 5:
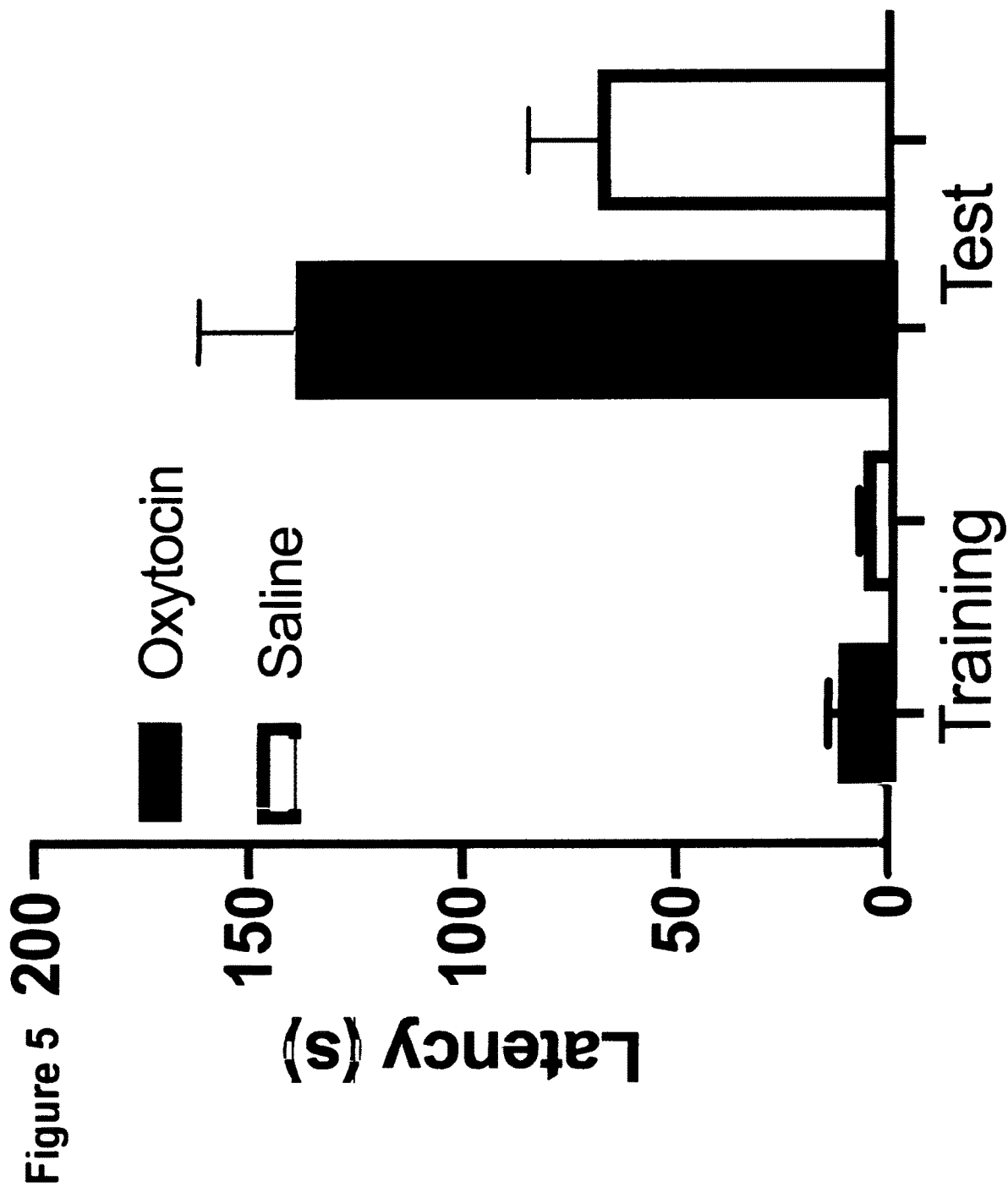
FIG. 5: Neonatal oxytocin treatment improves learning and memory function in adolescent rats chronically exposed to fluoxetine prenatally.

Compared to saline treated animals, a clear statistically significant improvement in learning and memory function as measured by the Passive Avoidance Test was noted for animals treated with daily injections of 2 mg/kg oxytocin for the first 10 postnatal days; That is, oxytocin treated animals showed a greater latency to enter a chamber that had previously been paired with a mild foot shock (FIG. 5).

No meaningful differences in locomotor activity or anxiety-like behavior were noted between the two treatment groups (data not shown).

Importantly, all animals were drug free during training and testing and had 21-25 days of wash-out from last exposure to oxytocin or saline

Example 6: Neonatal Treatment with Various Doses of Oxytocin Reduces Mortality in Rat Pups Chronically Exposed to Morphine Prenatally This example demonstrates the ability of three different doses of oxytocin to reduce mortality in rat pups chronically exposed to an opioid analgesic agent prenatally.

Beginning on the second day of gestation, timed-pregnant Sprague-Dawley rats (n=8) were treated with daily escalating doses (5-40 mg/kg/day) of morphine administered by subcutaneous injection for the entire period of gestation (approximately 21 days); Upon birth, rat pups were fostered by drug-naïve surrogate Sprague-Dawley rats (n=8) that had recently given birth to their own litter; Rat pups having been exposed to morphine prenatally, were dosed daily with either 0.3, 1, or 2 mg/kg oxytocin or 0.9% saline (n=18/group) by subcutaneous injection for the first 10 postnatal days; Survival rates and body weight were measured daily for the first 30 postnatal days.

Figure 6A:
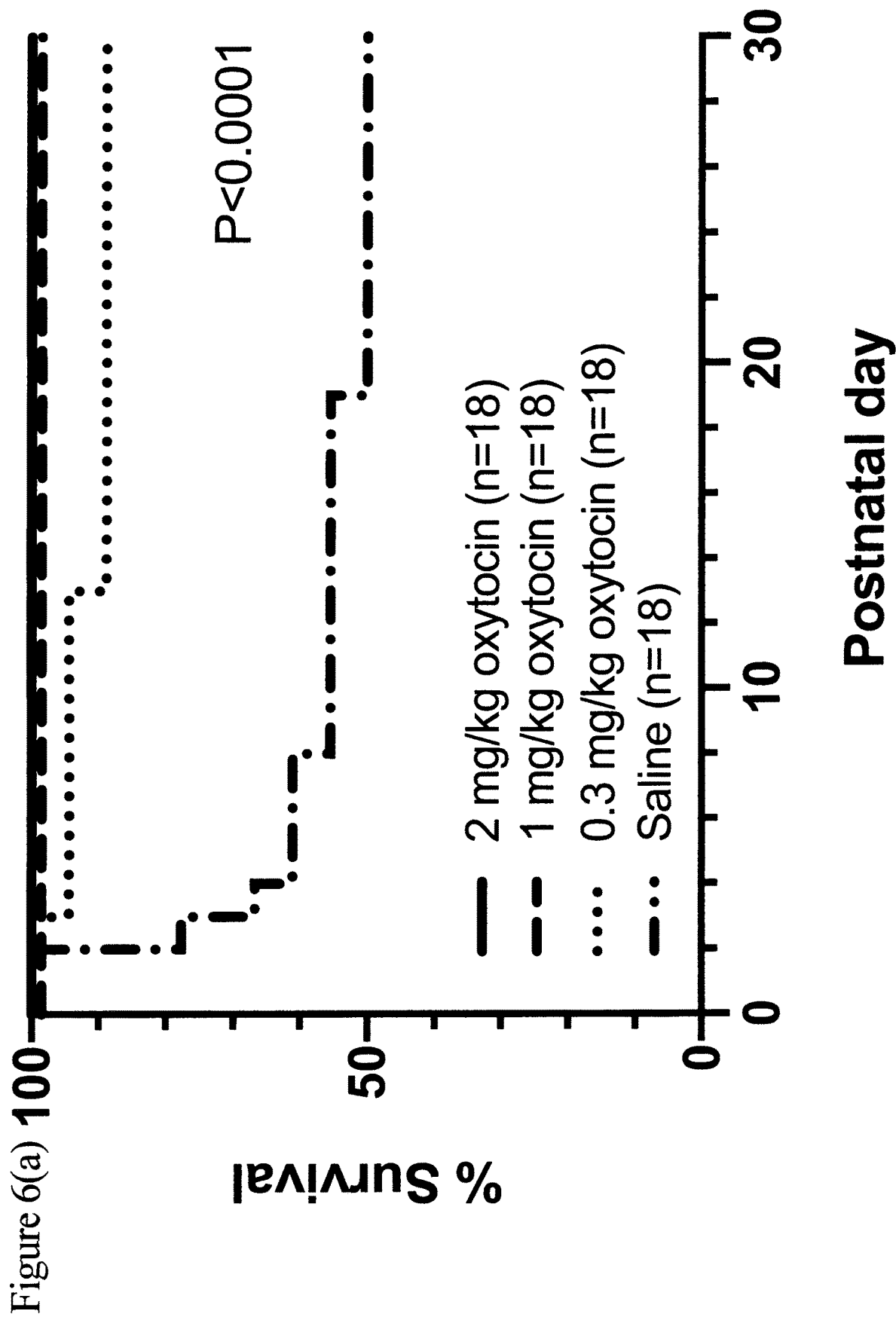
FIGS. 6a and 6b: Neonatal treatment with various doses of oxytocin reduces mortality in rat pups chronically exposed to morphine prenatally.

Compared to saline treated animals, a clear statistically significant improvement in percentage survival rates for the first 30 postnatal days was noted for animals that had been treated with daily injections of all three doses of oxytocin (FIG. 6a) for the first 10 postnatal days.

Figure 6B:
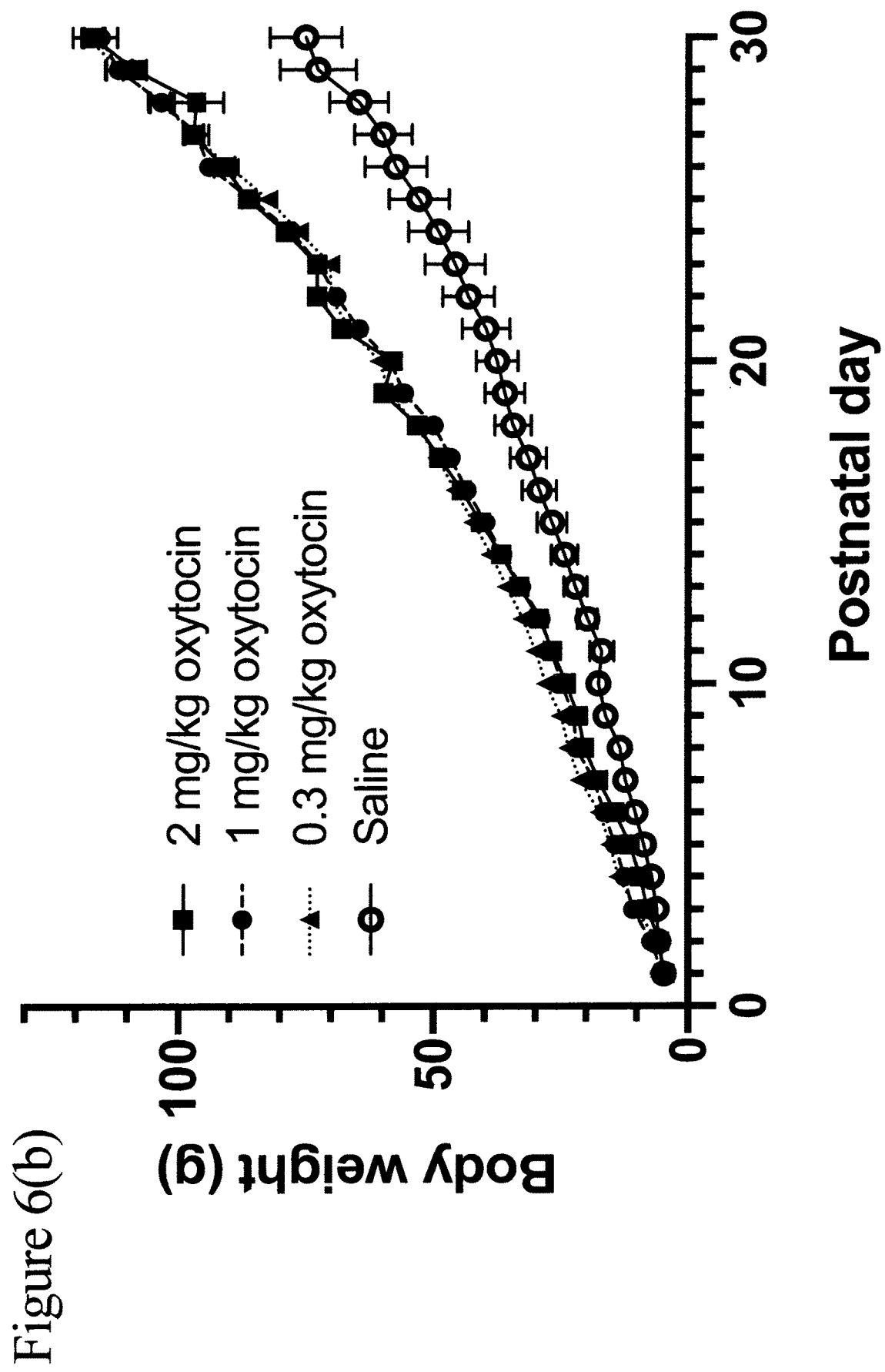

Compared to saline treated animals, a clear statistically significant increase in body weight throughout the first 30 postnatal days was noted for animals that had been treated with daily injections of all three doses of oxytocin (FIG. 6b) for the first 10 postnatal days.

Example 7: Neonatal Treatment with Oxytocin Dose-Dependently Increases Locomotor Activity During Acute Stages of Withdrawal in Rat Pups Chronically Exposed to Morphine Prenatally This example demonstrates the ability of specific doses of oxytocin to increase locomotor activity during the acute stages of withdrawal in rat pups chronically exposed to an opioid analgesic agent prenatally.

Locomotor activity was measured for 5 minutes on postnatal days 3, 6, 9, and 30 in rats that had been chronically exposed to morphine prenatally and treated with either daily 0.3, 1, or 2 mg/kg oxytocin or 0.9% saline by subcutaneous injection for the first 10 postnatal days.

Figure 7A:
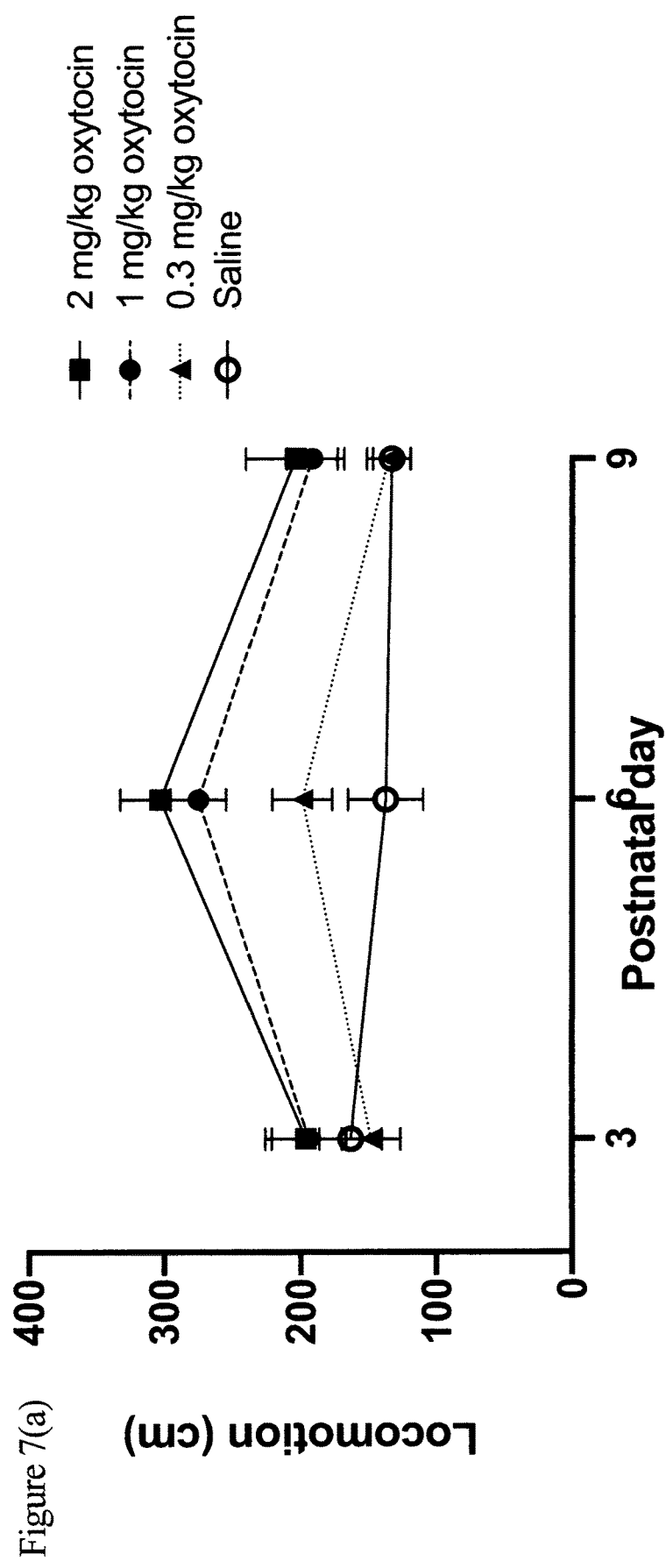
FIGS. 7a and 7b: Neonatal treatment with oxytocin dose-dependently increases locomotor activity during acute stages of withdrawal in rat pups chronically exposed to morphine prenatally.
Figure 7B:
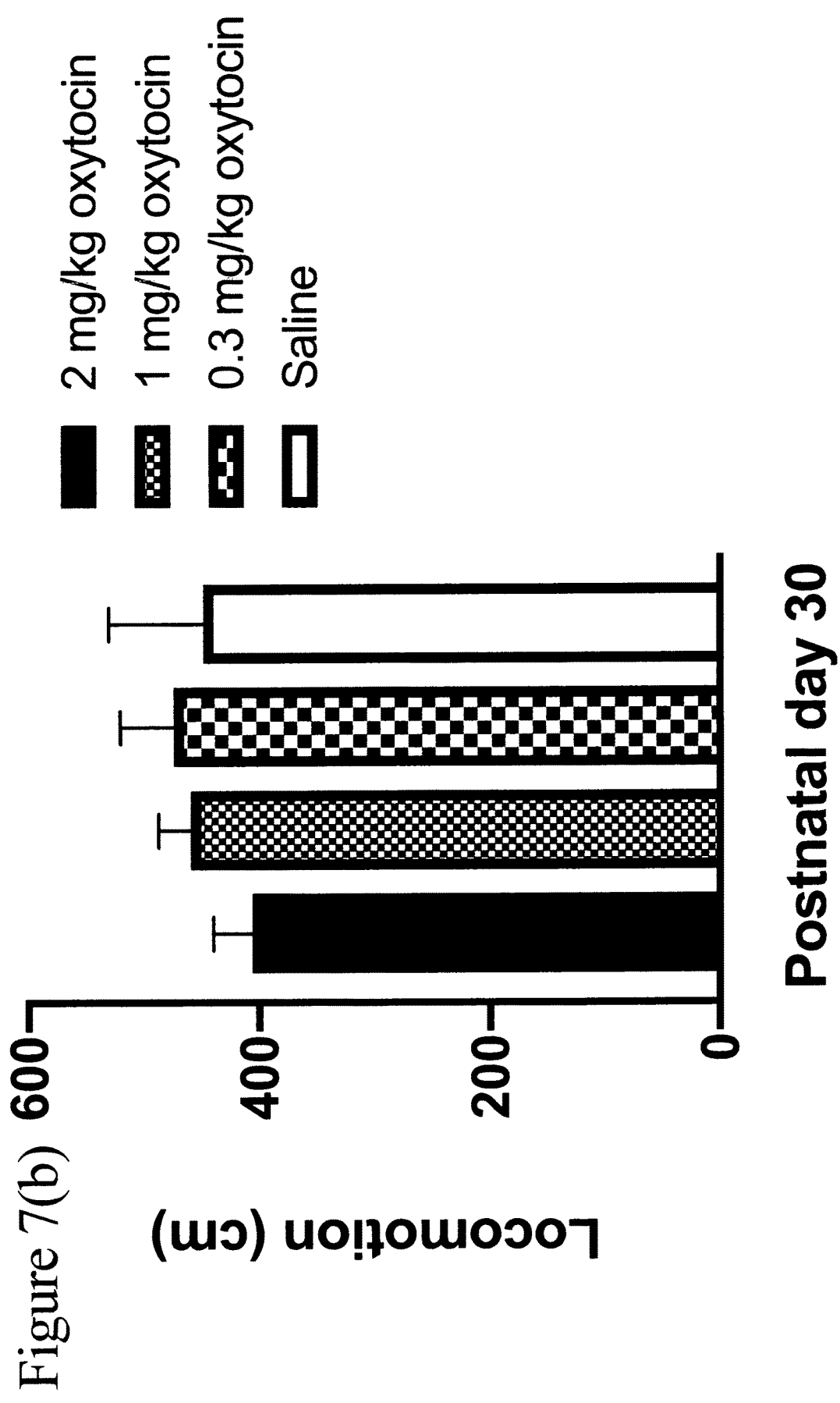

Compared to the saline (n=11) treated animals, a clear statistically significant increase in locomotor activity on postnatal day 6, but not on postnatal days 3 or 9, was noted for rat pups that had been treated with either 1 or 2 mg/kg oxytocin (n=18/group) (FIG. 7a);

No meaningful differences in locomotor activity were noted between treatment groups at postnatal day 30 (FIG. 7b).

Example 8: Neonatal Oxytocin Treatment Dose-Dependently Reduces Anxiety-Like Behavior and Improves Learning and Memory Function in Adolescent Rats Chronically Exposed to Morphine Prenatally This example demonstrates a dose-dependent effect of oxytocin treatment during neonate development to decrease adolescent anxiety-like behavior and improve adolescent learning and memory function in rats chronically exposed to an opioid analgesic agent prenatally.

Between postnatal days 31 and 35, surviving animals that were chronically exposed to morphine prenatally and treated with subcutaneous injections of 0.3, 1, 2 mg/kg oxytocin or 0.9% saline for the first 10 postnatal days underwent testing for anxiety-like behavior as measured by the Light-Dark Box and learning and memory function as measured by the Passive Avoidance Test.

Figure 8A:
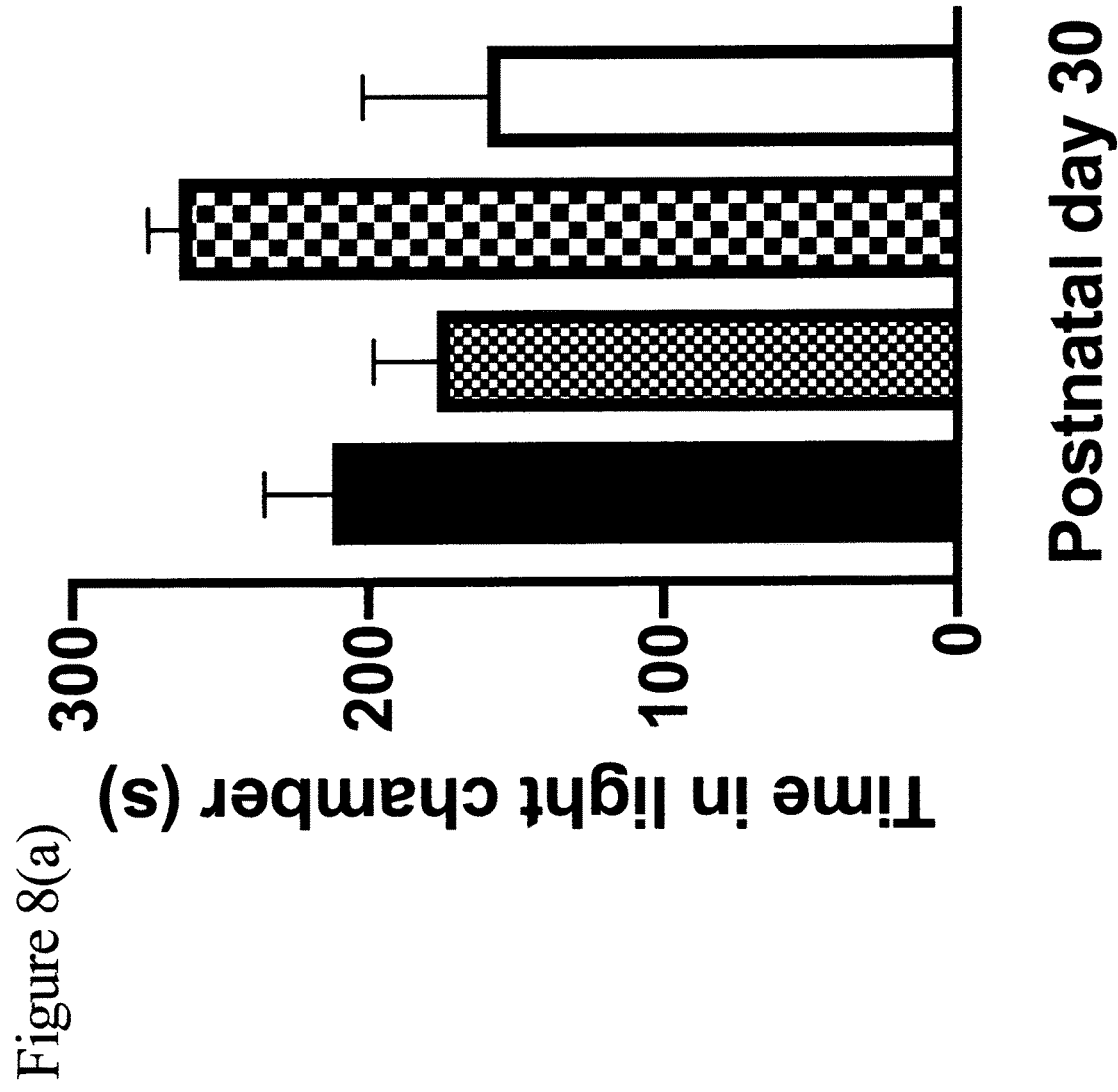
FIGS. 8a and 8b: Neonatal oxytocin treatment dose-dependently reduces anxiety-like behavior and improves learning and memory function in adolescent rats chronically exposed to morphine prenatally.

Compared to the saline treated animals (n=9), a clear statistically significant decrease in anxiety-like behavior was noted for animals treated with daily injections of 0.3 mg/kg oxytocin (n=16) (FIG. 8a) for the first 10 postnatal days; That is, animals treated with 0.3 mg/kg oxytocin spent more time in the light chamber, than did animals treated with saline.

Figure 8B:
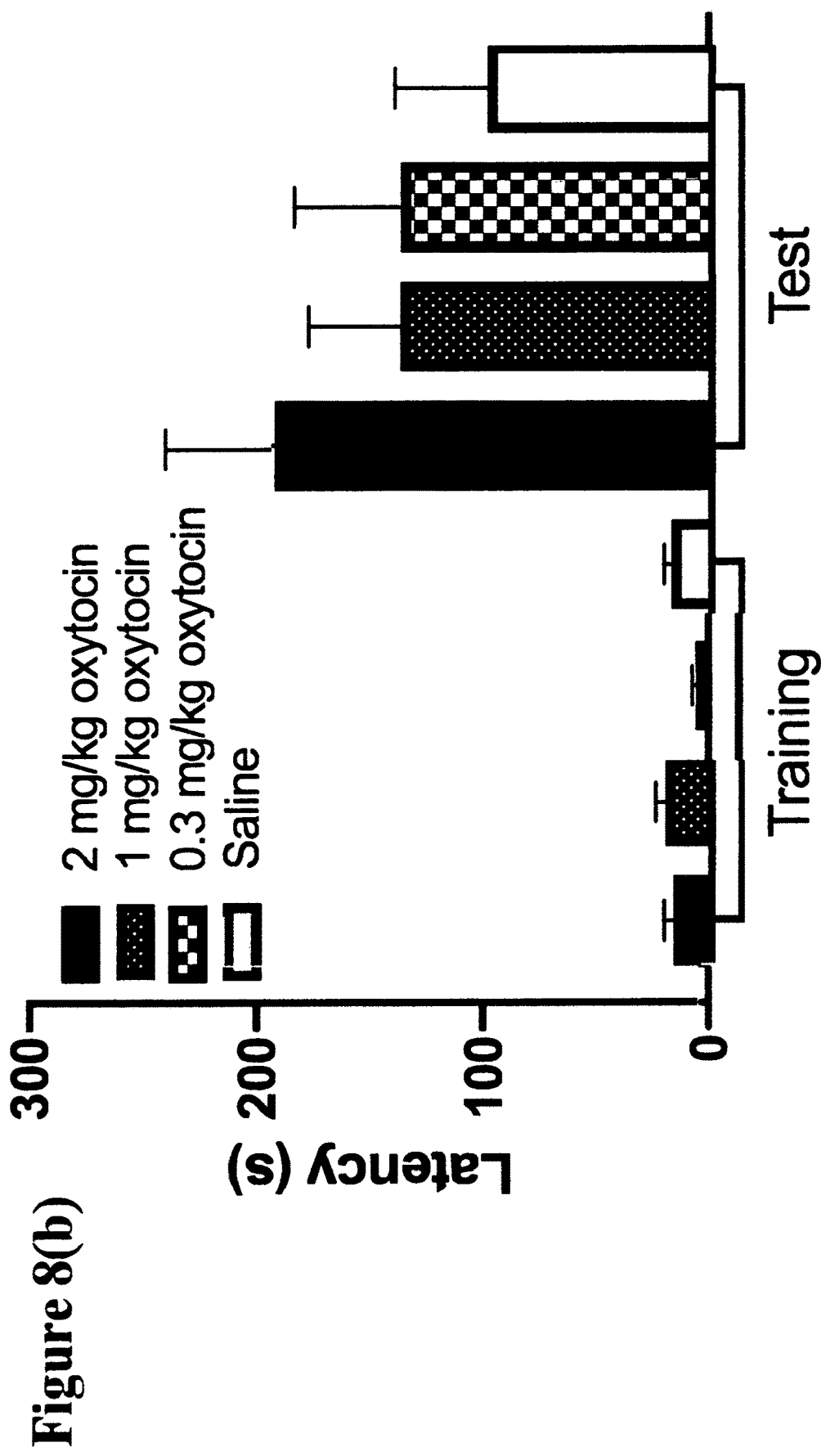

Compared to saline treated animals, a numerical improvement in learning and memory function was noted for animals that had been treated with daily injections of 2 mg/kg oxytocin (FIG. 8b; n=8/group) for the first 10 postnatal days; That is, compared to the saline treated animals, animals that had been treated with 2 mg/kg oxytocin showed a numerical increase in latency to enter a chamber that had previously been paired with a mild foot shock.

Importantly, all animals were drug free during training and testing and had 21-25 days of wash-out from last exposure to oxytocin or saline.

Example 9: Neonatal Treatment with Oxytocin Improves Sociability and Social Memory in Adolescent Rats Chronically Exposed to Morphine Prenatally This example demonstrates the ability of oxytocin treatment during neonate development to increase adolescent social novelty behavior and social memory in rats chronically exposed to an opioid analgesic agent prenatally.

Between postnatal days 31 and 35, surviving animals that were chronically exposed to morphine prenatally and treated with 0.3, 1, or 2 mg/kg oxytocin or 0.9% saline (n=8/group) by subcutaneous injection for the first 10 postnatal days underwent testing for social novelty behavior as measured and social memory function as measured by the Automated Three-Chamber Test.

Briefly, the Three-Chamber Test assesses cognition in the form of social novelty and social memory; Social novelty occurs in three sessions within a three-chambered box with openings between the chambers. After habituation to the empty box, the test animal encounters a novel conspecific under one pencil cup and an empty pencil cup. The test animal then encounters the familiar conspecific and a second novel conspecific under the previously empty pencil cup; Animals that show intact social novelty behavior will show a preference to investigate the novel conspecific; Twenty-four hours later, social memory is tested by placing the test animal back in to the chamber with the two familiar conspecifics; Animals with intact social memory will spend an equal amount of time investigating the two familiar conspecifics. Duration of time spent investigating conspecifics is measured automatically using a SmartCage™.

Figure 9A:
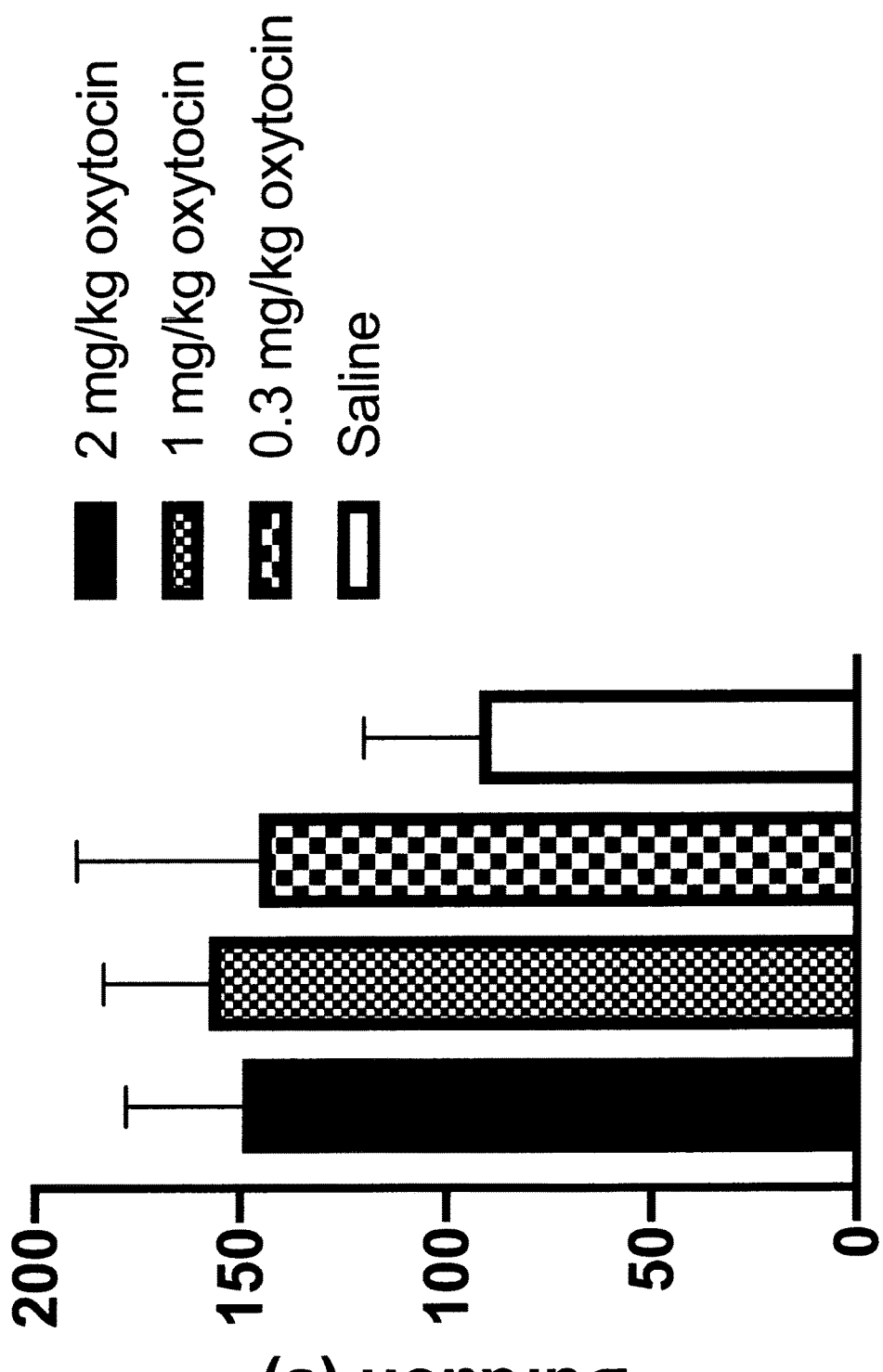
FIGS. 9a and 9b: Neonatal treatment with oxytocin improves sociability and social memory in adolescent rats chronically exposed to morphine prenatally.

Compared to saline treated animals, a trend towards increased social novelty behavior was noted for animals treated with daily injections of all doses of oxytocin (FIG. 9a) for the first 10 postnatal days; That is, animals that had been treated with all doses of oxytocin showed a numerically greater duration of time spent investigating a novel conspecific, than did animals treated with saline.

Figure 9B:
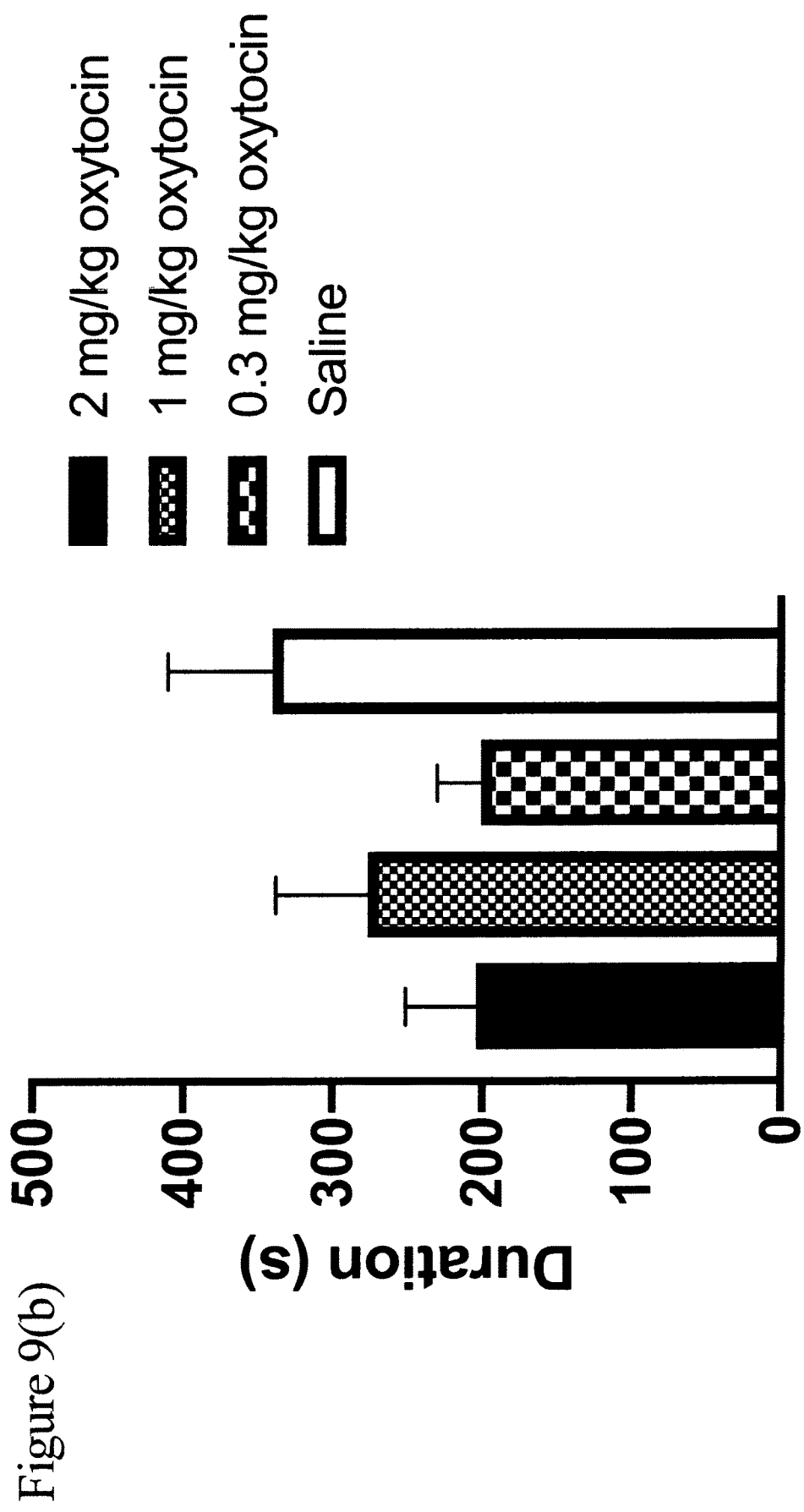

Compared to saline treated animals, a statistical trend towards improved social memory function was noted for animals that had been treated with daily injections of 2 mg/kg oxytocin (FIG. 9b) for the first 10 postnatal days; That is, animals that had been treated with daily injections of saline spent a longer duration of time investigating a familiar conspecific than did animals treated with daily injections of 2 mg/kg doses of oxytocin during the first 10 postnatal days.

Importantly, all animals were drug free during training and testing and had 21-25 days of wash-out from last exposure to oxytocin or saline.

Example 10: High-Dose Neonatal Oxytocin Treatment Reduces Mortality in Rat Pups Chronically Exposed to Diazepam Prenatally This example demonstrates the ability of high-dose oxytocin treatment to improve survival in rat pups chronically exposed to a benzodiazepine sedating agent prenatally.

Beginning on the second day of gestation, timed-pregnant Sprague-Dawley rats (n=8) were treated with daily escalating doses (2-15 mg/kg/day) of diazepam administered by subcutaneous injection for the entire period of gestation (approximately 21 days); Upon birth, rat pups were fostered by drug-naïve surrogate Sprague-Dawley rats (n=8) that had recently given birth to their own litter; Rat pups having been exposed to morphine prenatally, were dosed daily with either 0.3, 1, or 2 mg/kg oxytocin or 0.9% saline (n=16/group) by subcutaneous injection for the first 10 postnatal days; Survival rates and body weight were measured daily for the first 30 postnatal days.

Figure 10A:
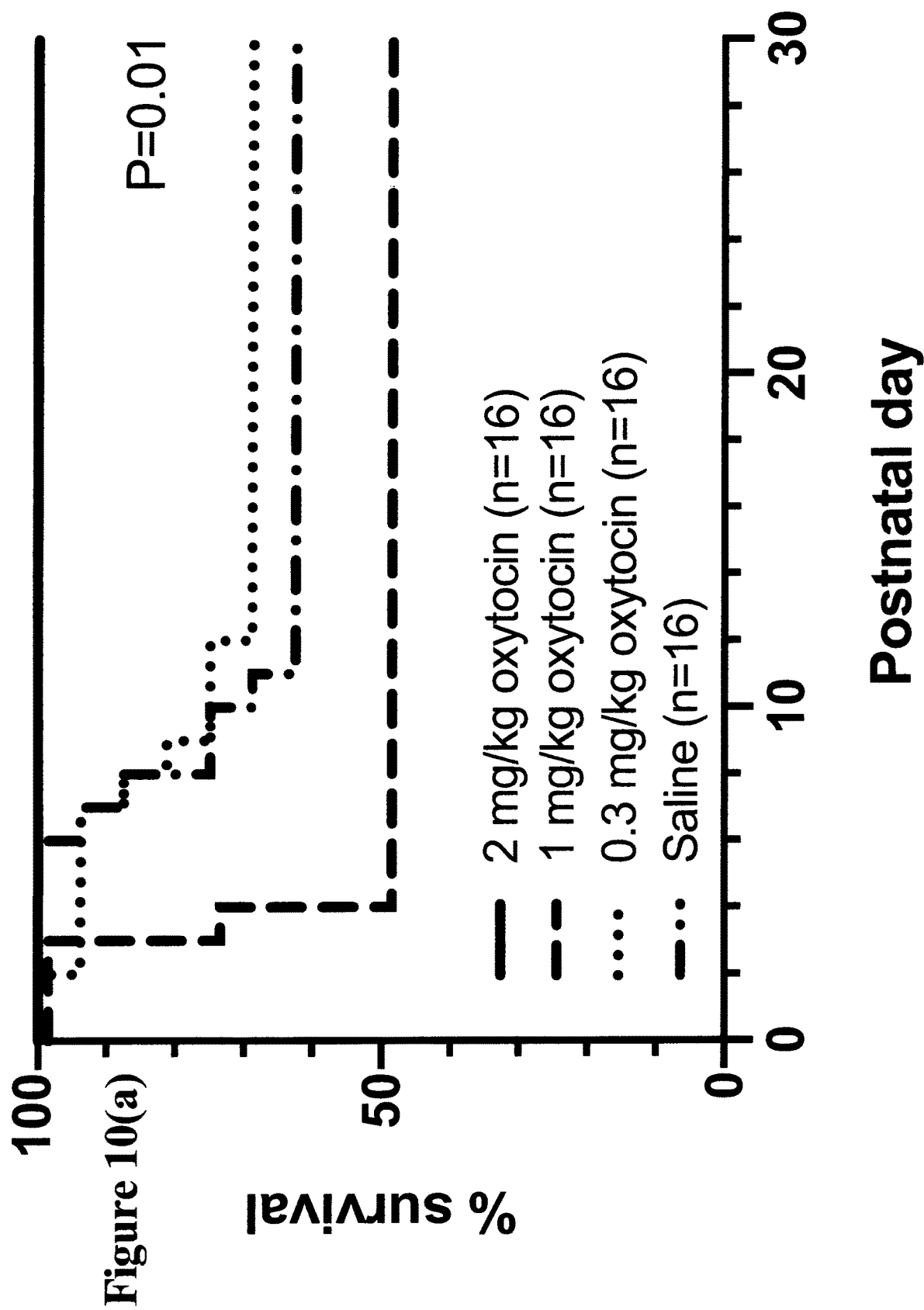
FIGS. 10a and 10b: High dose neonatal oxytocin treatment reduces mortality in rat pups chronically exposed to diazepam prenatally.

Compared to the saline treated animals, a clear statistically significant improvement in percentage survival rates for the first 30 postnatal days was noted for animals that had been treated with daily injections of 2 mg/kg, but not 0.3 or 1 mg/kg, oxytocin (FIG. 10a) for the first 10 postnatal days.

Figure 10B:
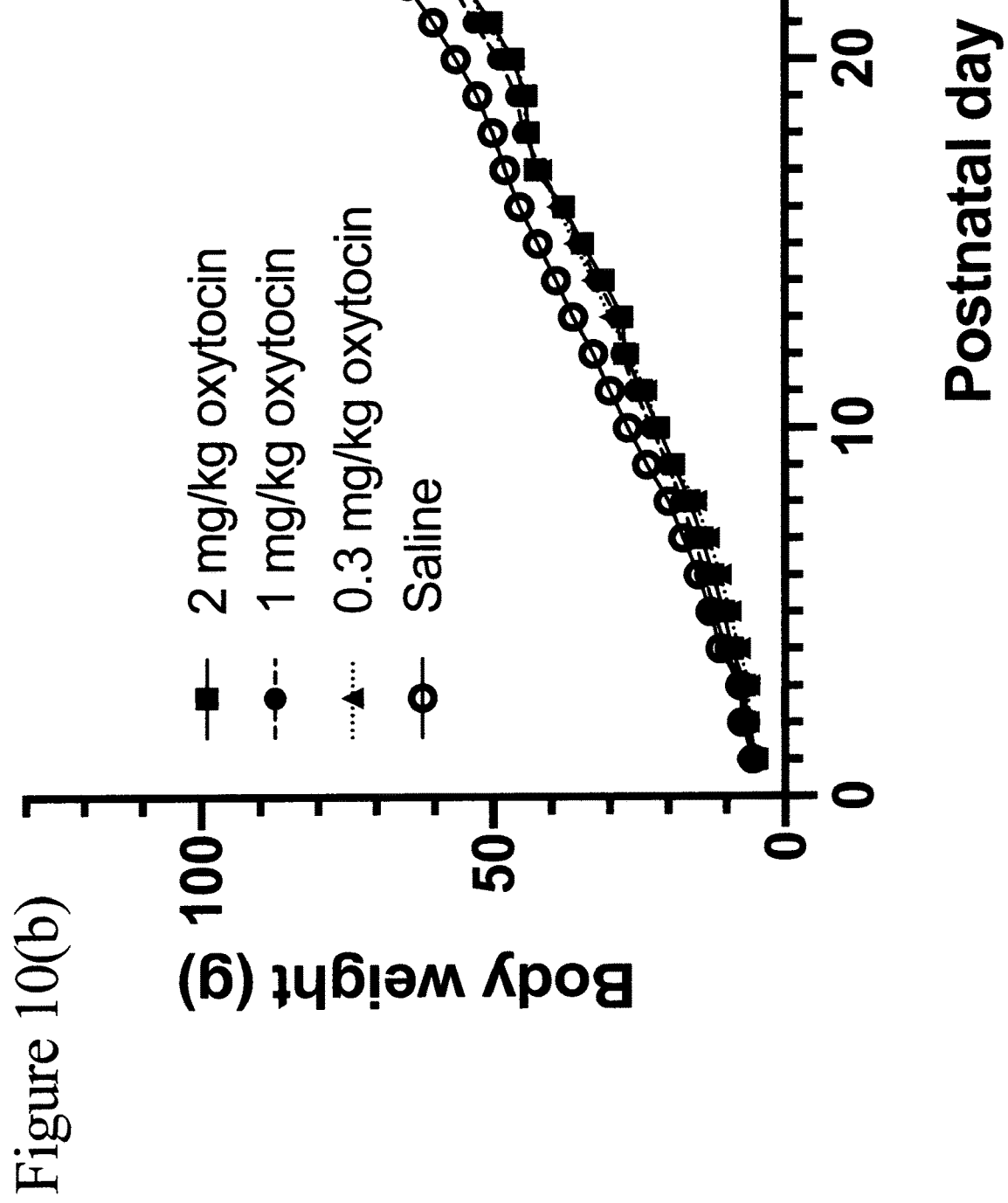

Compared to saline treated animals, a clear statistically significant decrease in body weight throughout the first 30 postnatal days was noted for animals that had been treated with daily injections of all three doses of oxytocin (FIG. 10b) for the first 10 postnatal days.

Example 11: Neonatal Oxytocin Treatment Decreases Locomotor Activity During Acute Stages of Withdrawal in Rat Pups Chronically Exposed to Diazepam Prenatally This example demonstrates the ability of different doses of oxytocin to decrease locomotor activity during the acute stages of withdrawal in rat pups chronically exposed to a benzodiazepine sedating agent prenatally.

Locomotor activity was measured for 5 minutes on postnatal days 3, 6, 9, and 30 in rats that had been chronically exposed to diazepam prenatally and treated with either daily 0.3, 1, or 2 mg/kg oxytocin or 0.9% saline by subcutaneous injection for the first 10 postnatal days.

Compared to saline treated animals (n=16), a clear statistically significant decrease in locomotor activity on postnatal days 3 and 6 was noted for animals that had been treated with injections of all three doses of oxytocin (0.3 mg/kg, n=15; 1 mg/kg, n=12; 2 mg/kg, n=16).

Figure 11A:
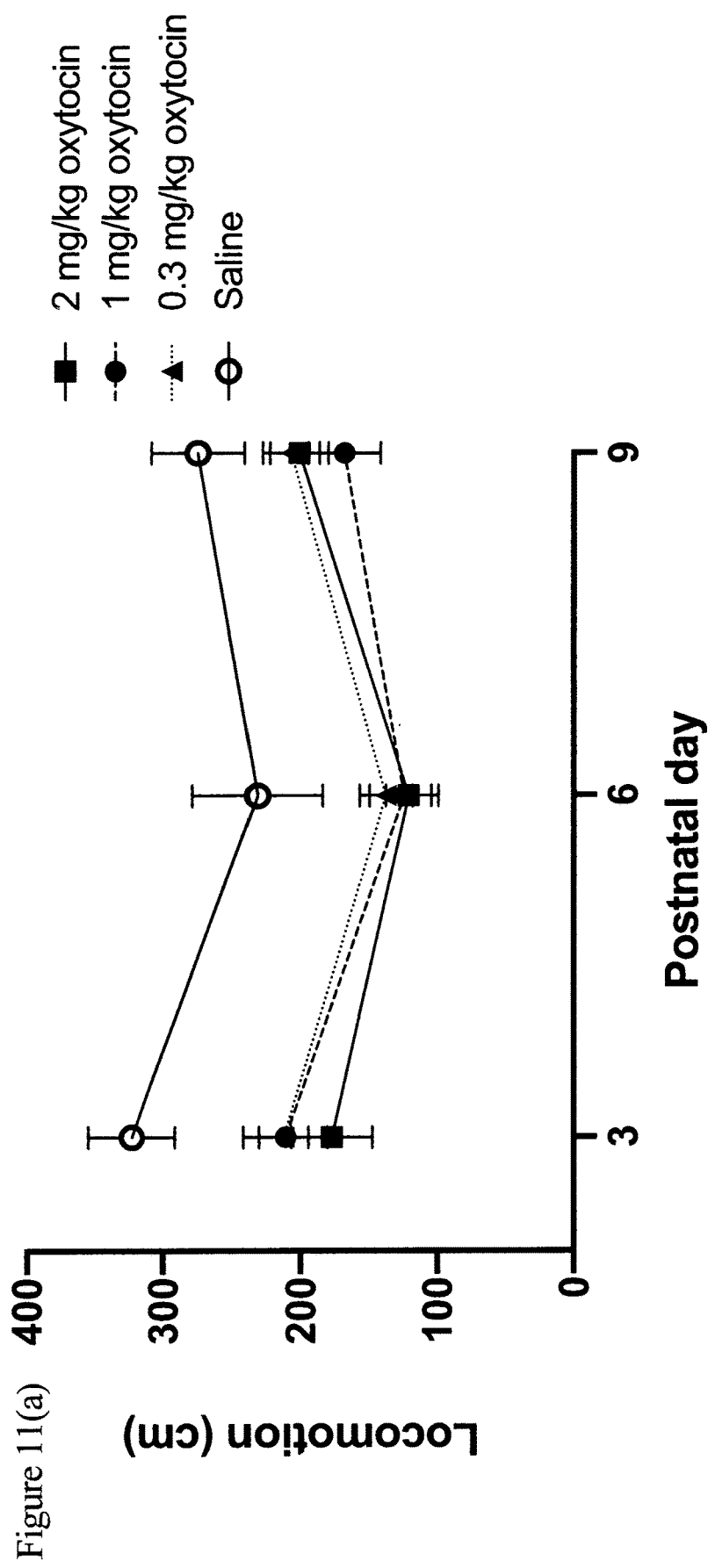
FIGS. 11a and 11b: Neonatal oxytocin treatment decreases locomotor activity during acute stages of withdrawal in rat pups chronically exposed to diazepam prenatally.

Compared to the saline treated animals, a clear statistically significant decrease in locomotor activity on postnatal day 6 was noted for animals that had been treated with daily injections of 0.3 mg/kg (n=15) and 2 mg/kg (n=16)oxytocin (FIG. 11a).

Compared to the saline treated animals (n=12), a clear statistically significant decrease in locomotor activity on postnatal day 9 was noted for animals that had been treated with daily injections of 2 mg/kg oxytocin (n=16) (FIG. 11a) for the first 10 postnatal days.

Figure 11B:
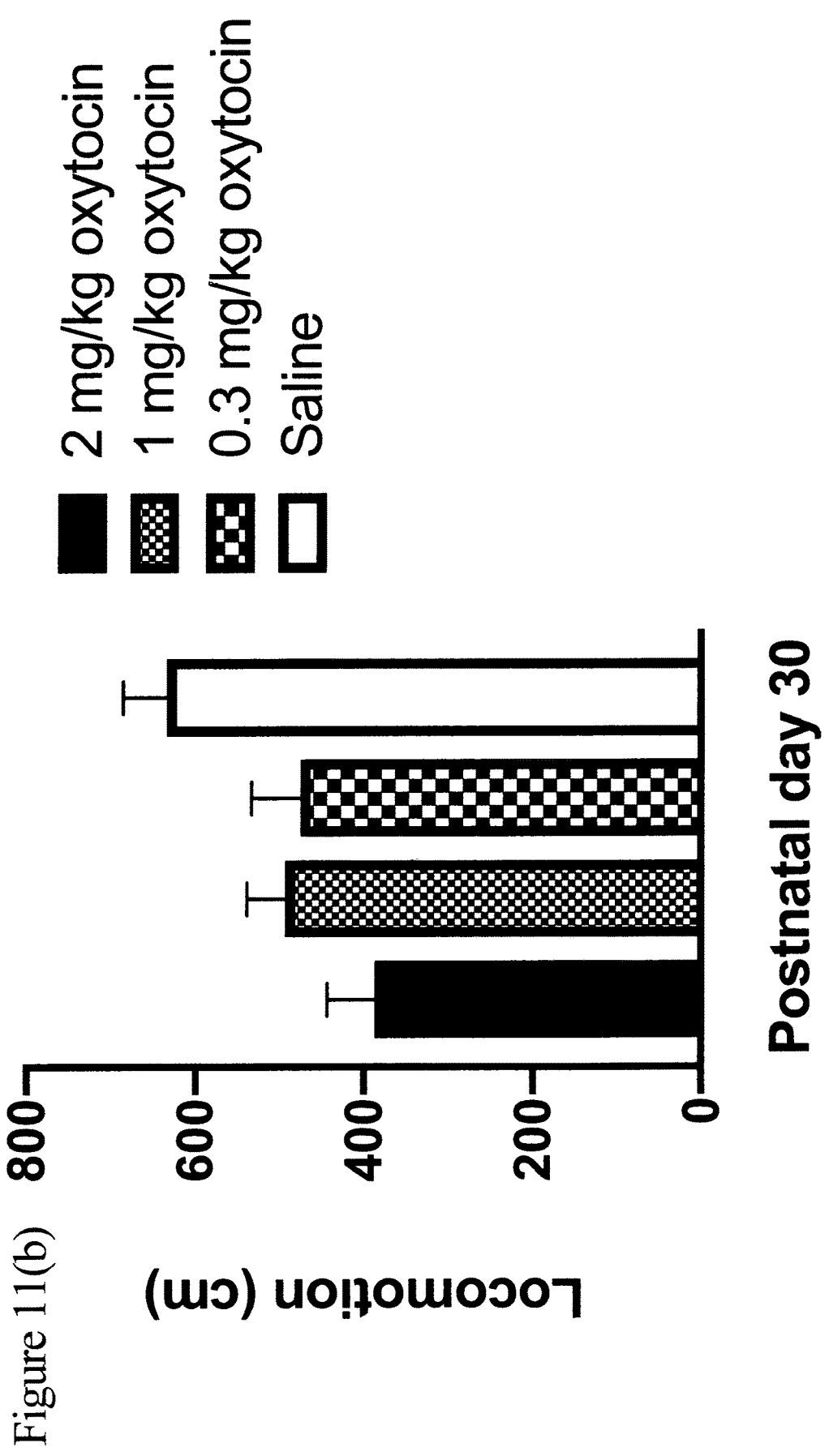

Compared to the saline treated animals (n=11), a clear statistically significant decrease in locomotor activity on postnatal day 30 was noted for animals that had been treated with daily injections of 2 mg/kg oxytocin (n=16) (FIG. 11b) for the first 10 postnatal days.

Example 12: Neonatal Oxytocin Treatment Decreases Anxiety-Like Behavior and Improves Learning and Memory Function in Adolescent Rats Chronically Exposed to Diazepam Prenatally This example demonstrates the ability of specific doses of oxytocin treatment during neonate development to decrease adolescent anxiety-like behavior and improve adolescent learning and memory function in rats chronically exposed to a benzodiazepine sedating agent prenatally.

Between postnatal days 31 and 35, surviving animals that were chronically exposed to diazepam prenatally and treated with 0.3, 1, or 2 mg/kg oxytocin or 0.9% saline by subcutaneous injection for the first 10 postnatal days underwent testing for anxiety-like behavior as measured by the Light-Dark Box and learning and memory function as measured by the Passive Avoidance Test.

Figure 12A:
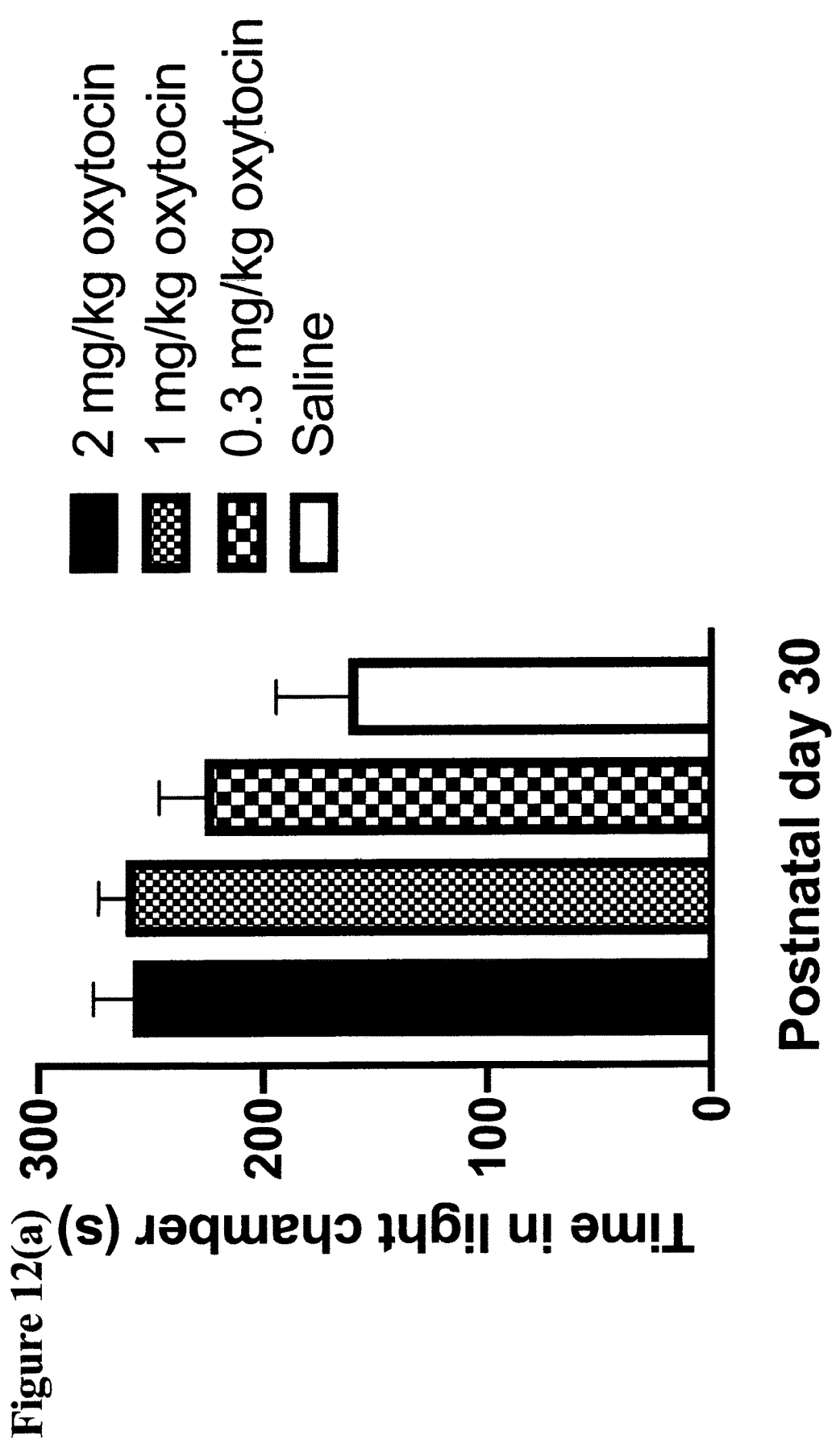
FIGS. 12a and 12b: Neonatal oxytocin treatment decreases anxiety-like behavior and improves learning and memory function in adolescent rats chronically exposed to diazepam prenatally.

Compared to animals treated with subcutaneous injections of saline (n=11), a clear statistically significant reduction in anxiety-like behavior was noted for animals treated with subcutaneous injections of 1 mg/kg (n=8) and 2 mg/kg (n=16)oxytocin (FIG. 12a) for the first 10 postnatal days; That is, compared to saline treated animals, animals that had been treated with subcutaneous injections of oxytocin during the first 10 postnatal days spent more time in the light chamber.

Figure 12B:
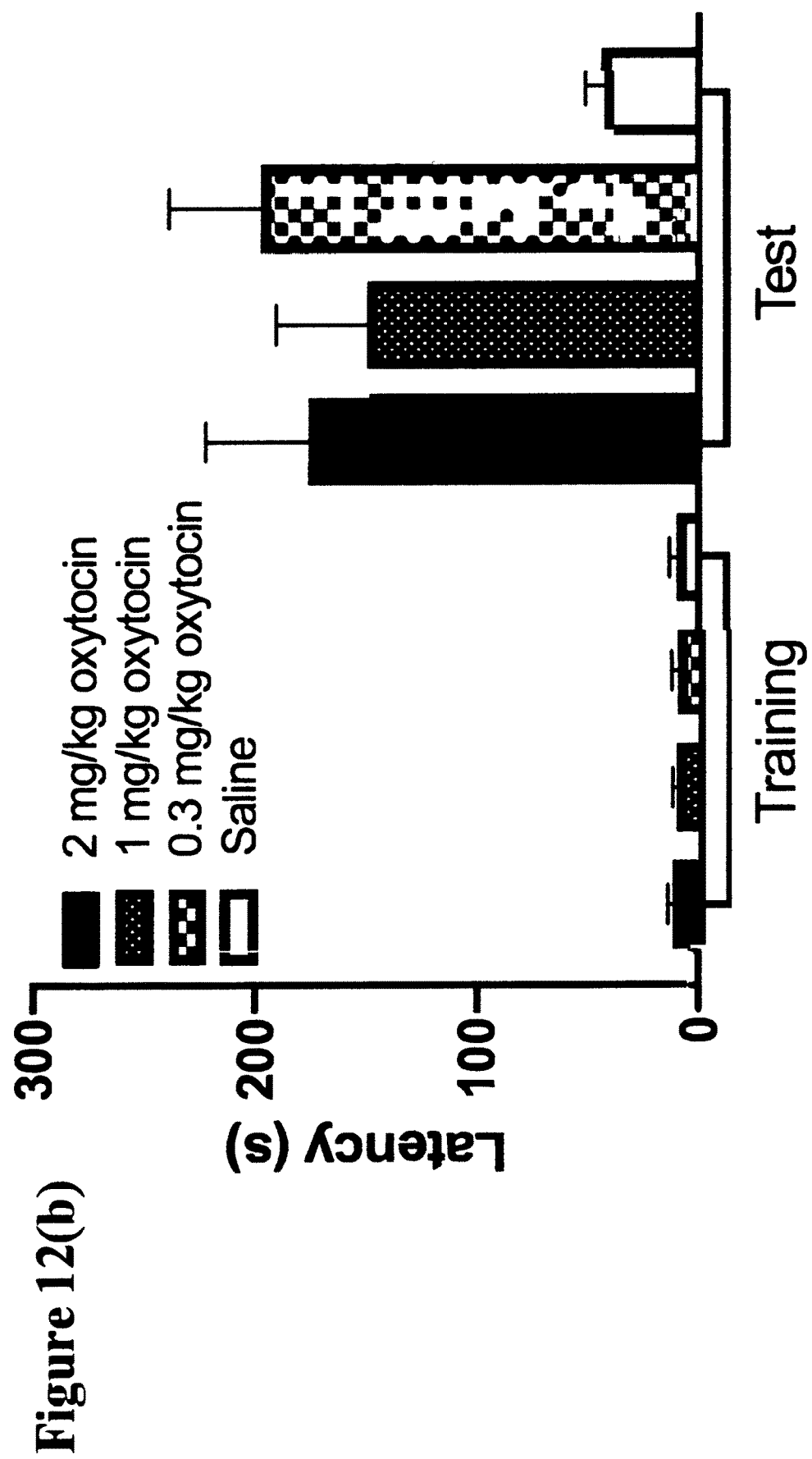

Compared to animals treated with subcutaneous injections of saline (n=8) for the first 10 postnatal days, a clear statistically significant improvement in learning and memory function was noted for animals that had been treated with subcutaneous injections of all doses of oxytocin (n=8/group; FIG. 12b); That is, animals that had been treated with daily subcutaneous injections of all doses of oxytocin during the first 10 postnatal days showed a greater latency to enter a chamber that had previously been paired with a mild foot shock, compared to saline treated animals.

Importantly, all animals were drug free during training and testing and had 21-25 days of wash-out from last exposure to oxytocin or saline.

Example 13: Neonatal Treatment with Oxytocin Improves Sociability and Social Memory in Adolescent Rats Chronically Exposed to Diazepam Prenatally This example demonstrates the ability of oxytocin treatment during neonate development to increase adolescent social novelty behavior and social memory in rats chronically exposed to a benzodiazepine sedating agent prenatally.

Between postnatal days 31 and 35, surviving animals that were chronically exposed to diazepam prenatally and treated with subcutaneous injections of 0.3, 1, 2 mg/kg oxytocin or 0.9% saline (n=8/group) during the first 10 postnatal days underwent testing for social novelty behavior and social memory function as measured by the Automated Three-Chamber Test.

Figure 13A:
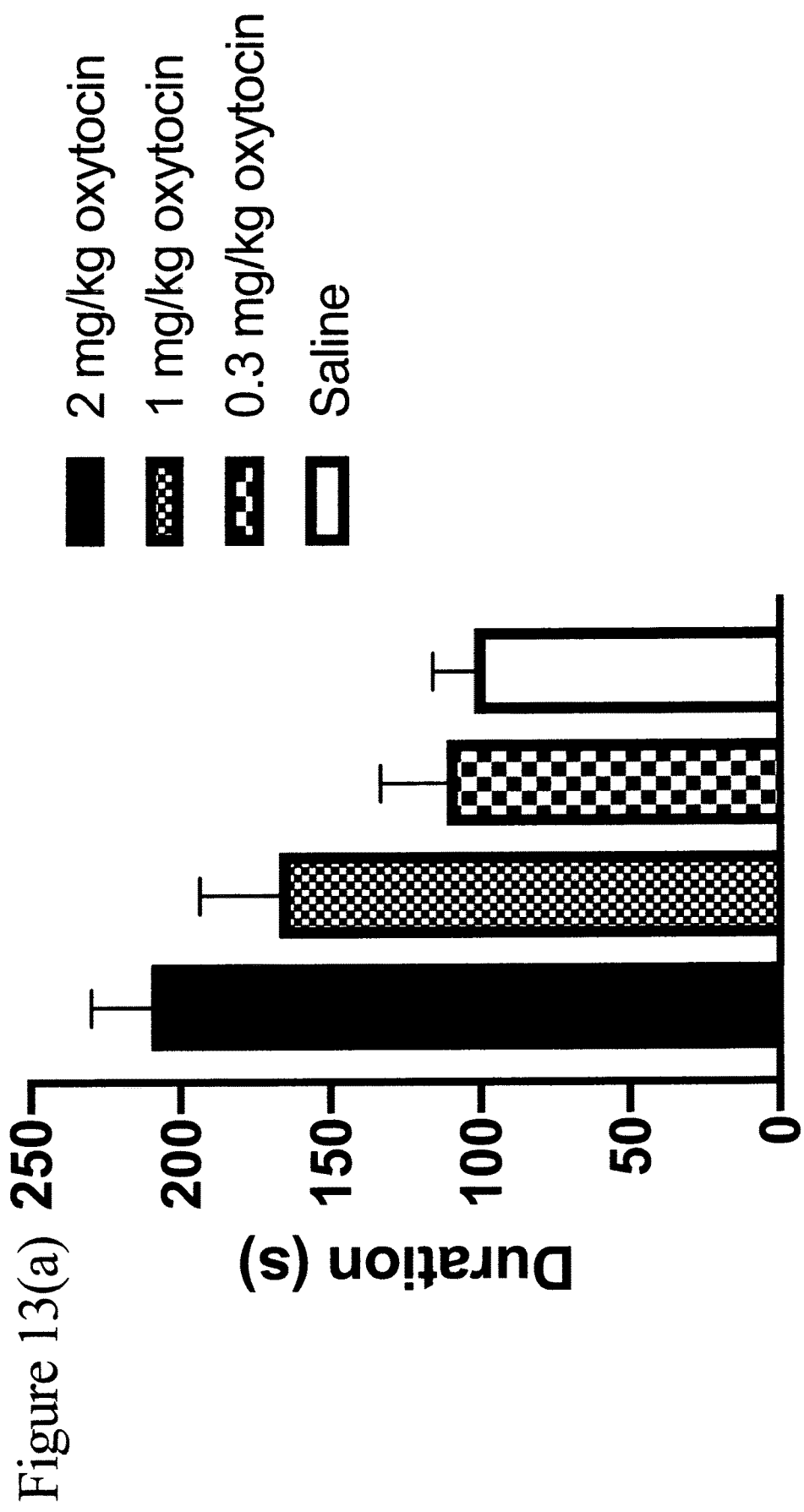
FIGS. 13a and 13b: Neonatal treatment with oxytocin improves sociability and social memory in adolescent rats chronically exposed to diazepam prenatally.

Compared to saline treated animals, a clear statistically significant increase in social novelty behavior was noted for animals treated with daily injections of 1 and 2 mg/kg oxytocin for the first 10 postnatal days; That is, animals that had been treated with 1 or 2 mg/kg oxytocin spent a greater duration of time investigating a novel animal, than did animals treated with saline (FIG. 13a).

Figure 13B:
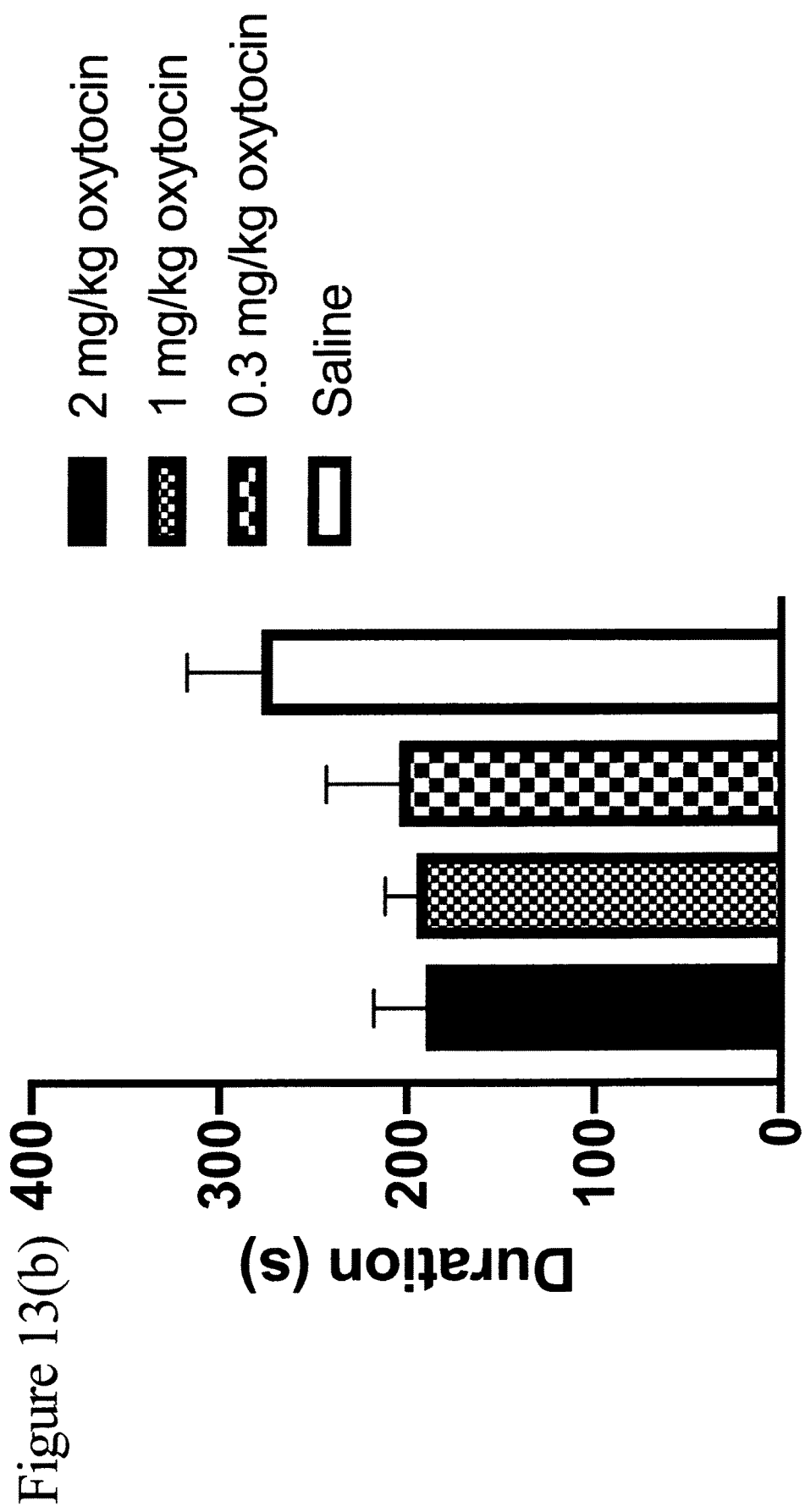

Compared to saline treated animals, a statistical trend toward improved social memory function was noted for animals that had been treated with daily injections 2 mg/kg oxytocin for the first 10 postnatal days; That is, animals that had been treated with daily injections of saline spent a greater duration of time investigating a familiar conspecific than did animals treated with daily injections of 2 mg/kg doses of oxytocin during the first 10 postnatal days (FIG. 13b).

Importantly, all animals were drug free during training and testing and had 21-25 days of wash-out from last exposure to oxytocin or saline.

Example 14: Neonatal Treatment with Oxytocin Reduces Body Weight During Development in Healthy Rats This example demonstrates the ability of different doses of oxytocin to reduce body weight throughout development in healthy rats.

Beginning immediately after birth, drug naïve Sprague-Dawley rat pups were fostered by drug naïve Sprague-Dawley surrogates that had recently given birth to their own litter; Rat pup were dosed daily with 0.3, 1, or 2 mg/kg oxytocin or saline by for the first 10 postnatal days; Survival rates and body weight were measured for the first 30 postnatal days.

Animals from all treatment groups survived for the first 30 postnatal days.

Figure 14:
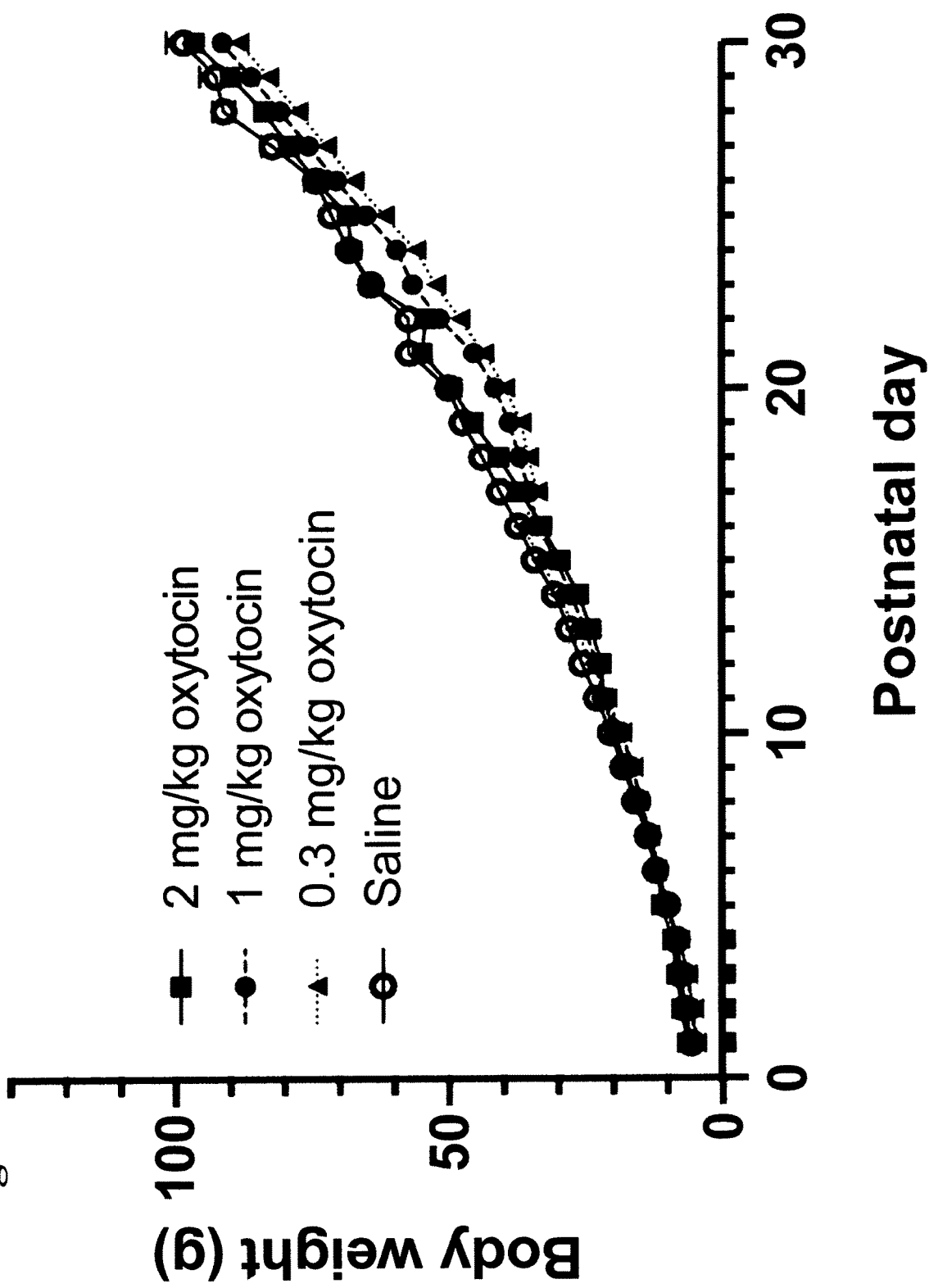
FIG. 14: Effects of neonatal oxytocin treatment on body weight during development in healthy rats.
Figure 15:
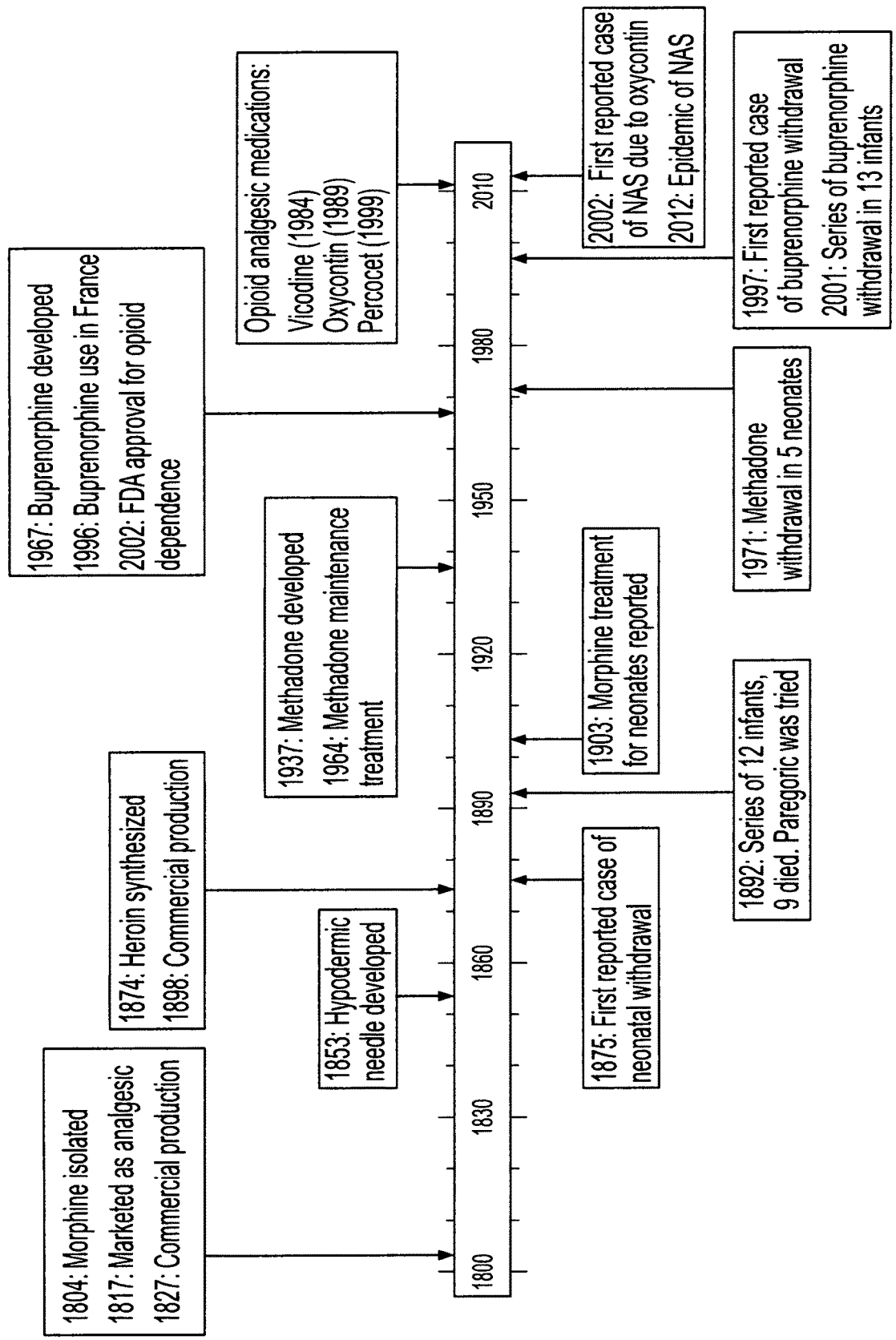
FIG. 15. Time line of NAS; Food and Drug Administration.

Compared to the saline treated animals, there was a clear statistically significant reduction in body weight throughout the first 30 postnatal days for animals treated with all doses of oxytocin for the first 10 postnatal days; However, at postnatal day 30 there was no difference in body weight between animals treated with saline and animals treated with 2 mg/kg oxytocin (FIG. 14) for the first 10 postnatal days.

Example 15: Clinical Trial of Intranasal Oxytocin for the Treatment of Neonatal Abstinence Syndrome This example outlines the study design for a prospective clinical trial aimed at determining the efficacy of intranasal oxytocin for the treatment of neonatal abstinence syndrome.

In a phase 1b/2a dose-finding, safety and efficacy study, a total of 60 term human neonates (≥37 weeks of gestation) with a diagnosis of neonatal abstinence syndrome who are known to be exposed to opioids prenatally and receive a diagnosis of neonatal abstinence syndrome will receive one of three open-label doses of oxytocin: 4 IU, 8 IU, 16 IU twice daily for up to 30 days; Blocks of 20 babies will be treated with each dose starting at the lowest dose and increasing only upon completion of satisfactory interim safety analyses; The co-primary efficacy endpoint measures are: 1. duration of standard of care pharmacological (opioid and non-opioid) treatment for neonatal abstinence syndrome and 2. length of stay from hospital admission to hospital discharge for treatment of neonatal abstinence syndrome; The decision to treat a baby with standard of care pharmacological treatment is made using the Finnegan scoring instrument which is administered to babies every 4 hours; On completion of the open-label portion of the study, a power-analysis will be performed to determine the number of babies needed to conduct a double-blind, randomized, controlled treatment trial to determine the efficacy of one dose of oxytocin compared to placebo; Again, the co-primary efficacy endpoint measures are: 1. duration of standard of care pharmacological (opioid and non-opioid) treatment for neonatal abstinence syndrome and 2. length of stay from hospital admission to hospital discharge for treatment of neonatal abstinence syndrome.

Although the foregoing invention has been described in some detail by way of illustration and example for purposes of clarity of understanding, it will be apparent to those skilled in the art that certain changes and modifications may be practiced without departing from the invention. Therefore, the descriptions and examples should not be construed as limiting the scope of the invention.

All patents, patent applications, documents and articles cited herein are incorporated by reference in their entireties.

---

The invention claimed is:

1. A method for treating Neonatal Abstinence Syndrome (NAS), in a mammalian subject in need thereof, wherein the method comprises administering to the subject a therapeutically effective amount of oxytocin peptide SEQ ID. NQ. 1 in an amount sufficient to reduce, ameliorate and/or eliminate symptoms of the syndrome in the subject.

2. The method of claim 1, wherein the mammalian subject has been exposed to an opioid or an opiate drug agent.

3. The method of claim 1, wherein the mammalian subject is a human.

4. The method of claim 3, wherein the human is a neonate.

5. The method of claim 2, wherein the subject has been biologically exposed to the opioid or the opiate drug agent prenatally.

6. The method of claim 2, wherein the subject exhibits symptoms of NAS, has been diagnosed with NAS, or is suspected of having NAS due to a biological exposure to an opioid or opiate drug agent.

7. The method of claim 1, wherein the subject exhibits symptoms of an iatrogenic disorder, has been diagnosed with an iatrogenic disorder, or is suspected of having an iatrogenic disorder due to a biological exposure to an opioid or opiate drug agent.

8. The method of claim 1, wherein the composition comprises oxytocin in an amount between about 1IU to about 100IU.

9. The method of claim 1, wherein the composition is formulated for intranasal administration.

* * * * *